(12) United States Patent
Küstner et al.

(10) Patent No.: US 8,854,617 B2
(45) Date of Patent: Oct. 7, 2014

(54) COMPOUNDS AND MARKERS FOR SURFACE-ENHANCED RAMAN SCATTERING

(75) Inventors: Bernd Küstner, Muhltal (DE); Sebastian Schlücker, Lotte-Halen (DE); Carsten Schmuck, Oberhausen (DE)

(73) Assignee: Julius-Maximilians-Universitat Wurzburg, Wurzburg (DE)

( * ) Notice: Subject to any disclaimer, the term of this patent is extended or adjusted under 35 U.S.C. 154(b) by 1082 days.

(21) Appl. No.: 12/679,571

(22) PCT Filed: Sep. 24, 2008

(86) PCT No.: PCT/EP2008/008098
§ 371 (c)(1),
(2), (4) Date: May 13, 2010

(87) PCT Pub. No.: WO2009/040114
PCT Pub. Date: Apr. 2, 2009

(65) Prior Publication Data
US 2010/0284917 A1 Nov. 11, 2010

(30) Foreign Application Priority Data
Sep. 24, 2007 (EP) .................................... 07018757

(51) Int. Cl.
| | | |
|---|---|---|
| G01J 3/44 | (2006.01) | |
| A61B 5/00 | (2006.01) | |
| A61K 9/14 | (2006.01) | |
| B32B 5/16 | (2006.01) | |
| G01N 33/532 | (2006.01) | |
| G01N 21/65 | (2006.01) | |
| B82Y 15/00 | (2011.01) | |

(52) U.S. Cl.
CPC ............ *G01N 21/658* (2013.01); *G01N 33/532* (2013.01); *B82Y 15/00* (2013.01)
USPC ............ 356/301; 424/9.6; 424/489; 428/403; 428/406; 428/407

(58) Field of Classification Search
USPC .................... 424/9.1, 489, 9.6; 356/952, 301; 428/403, 406, 407
See application file for complete search history.

(56) References Cited

U.S. PATENT DOCUMENTS

| 7,588,827 B2 * | 9/2009 | Nie et al. ...................... 428/403 |
| 2005/0089901 A1 | 4/2005 | Porter et al. |
| 2007/0048797 A1 | 3/2007 | Su |

FOREIGN PATENT DOCUMENTS

| DE | 10 2006 000 775 A1 | 7/2007 |
| ZA | 8502022 | * 11/1985 |

OTHER PUBLICATIONS

Office Action received in the related European Patent Application No. EP 08802574.7 dated Oct. 11, 2010.
Doering, et al., "Spectroscopic Tags Using Dye-Embedded Nanoparticles and Surface-Enhanced Raman Scattering"., Analytical Chemistry, 2003, vol. 75, No. 22, pp. 6171-6716.
Mulvaney, et al., "Glass-Coated, Analyte-Tagges Nanoparticles: A New Tagging System Based in Detection with Surface-Enhanced Raman Scattering", American Chemical Society, 2003, pp. 4784-4790.
Kim, et al, "Nanoparticle Probes with Surface Enhanced Raman Spectroscopic Tags for Cellular Cancer Targeting", *Anal. Chem.*, 2006, vol. 78, pp. 6967-6973.
Kriegisch, et al., "Self-Assembled Monolayers of Chromophores on Gold Surfaces" *Top Curr Chem*, 2005, vol. 258, pp. 257-313.
McCabe, et al., "SERRS labelled beads for multiplex detection", *The Royal Society of Chemistry*, 2005, vol. 132, pp. 303-308.
Schlucker, et al., "Immuno-Raman microspectroscopy: In situ detection of antigens in tissue specimens by surface-enhanced Raman scatterin", *Journal of Raman Spectroscopy*, 2006, vol. 37, pp. 719-721.
Simard, et al., "Formation and pH-controlled assembly of amphiphilic gold nanoparticles", *Chem Commun*, 2000, pp. 1943-1944.
Sung, et al., "Synthesis of Monofunctionalized Gold Nanoparticles by Fmoc Solid-Phase Reactions", *J. Am. Chem. Soc.*, 2004, vol. 126, pp. 5064-5065.
Yu, et al., "Multiplex Targeting, Tracking, and Imaging of Apoptosis by Fluorscent Surface Enhanced Raman Spectroscopic Dots", *Bioconjugate Chem.*, 2007, vol. 18, pp. 1155-1162.
The Partial International Search Report received in the correspondence International Application PCT/EP2008/008098.
Boal, et al., "Fabricationa and Self-Optimization of Multivalent Receptors on Nanoparticle Scaffolds", *J. Am. Chem. Soc.*, 2000, vol. 122, pp. 734-735.
Grubisha, et al., "Femtomolar Detection of Prostate-Specific Antigen: An Immunoassay Based on Surface-Enhanced Raman Scattering and Immunogold Labels", *Anal Chem.*, 2003, vol. 75, pp. 5936-5943.
Jun, et al., "Surface-Enhanced Raman Spectroscopic-Encoded Beads for Multiplex Immunoassay", *J. Comb. Chem.*, 2007, vol. 9, pp. 237-244.
Boal et al., "Fabrication and Self-Optimization of Multivalent Receptors on Nanoparticle Scaffolds," J. Am. Chem. Soc., 2000, pp. 734-735, vol. 122, No. 4.
Grubisha et al., "Femtomolar Detection of Prostate-Specific Antigen: An Immunoassay Based on Surface-Enhanced Raman Scattering and Immunogold Labels," Anal. Chem., Nov. 2003, pp. 5936-5943, vol. 75, No. 21.

(Continued)

*Primary Examiner* — Michael G Hartley
*Assistant Examiner* — Leah Schlientz
(74) *Attorney, Agent, or Firm* — Foley & Lardner LLP

(57) ABSTRACT

The present invention relates to compounds and markers for surface-enhanced Raman scattering (SERS), and methods for the preparation of the SERS markers. The present invention further relates to compositions, methods and uses, wherein the present SERS markers are employed.

38 Claims, 19 Drawing Sheets

(56) References Cited

OTHER PUBLICATIONS

Figure 1:
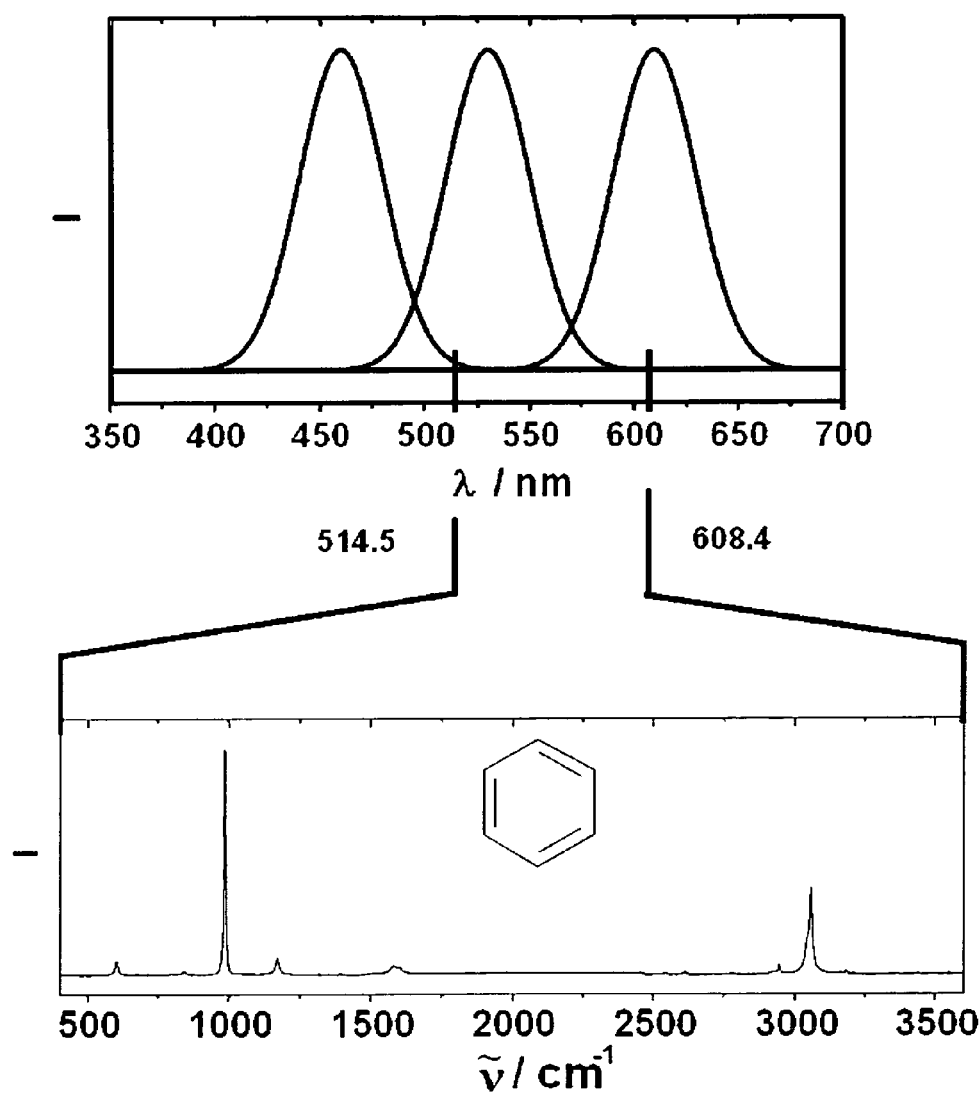

Jun et al., "Surface-Enhanced Raman Spectroscopic-Encoded Beads for Multiplex," J. Comb. Chem., 2007, pp. 237-244, vol. 9, No. 2.
Kim et al., "Nanoparticle Probes with Surface Enhanced Raman Spectroscopic Tags for Cellular Cancer Targeting," Anal. Chem., Oct. 2006, pp. 6967-6973, vol. 78, No. 19.
Kriegisch et al., "Self-Assembled Monolayers of Chromophores on Gold Surfaces," Top Curr. Chem., 2005, pp. 257-313, vol. 258.
McCabe et al., "Serrs labeled beads for multiplex detection," Faraday Discuss., 2006, pp. 303-319, vol. 132.
Schlücker et al., "Immuno-Raman microspectroscopy: *In situ* detection of antigens in tissue specimens by surface-enhanced Raman scattering," J Raman Spectroscopy, 2006, pp. 719-721, vol. 37.
Simard et al., "Formation and pH-controlled assembly of amphiphilic gold nanoparticles," Chem. Commun., 2000, pp. 1943-1944.
Sung et al., "Synthesis of Monofunctionalized Gold Nanoparticles by Fmoc Solid-Phase Reactions," JACS, 2004, pp. 5064-5065, vol. 126, No. 16.
Yu et al., "Multiplex Targeting, Tracking, and Imaging of Apoptosis by Fluorescent Surface Enhanced Raman Spectroscopic Dots," Bioconjugate Chem., 2007, pp. 1155-1162, vol. 18, No. 4.

* cited by examiner

COMPOUNDS AND MARKERS FOR SURFACE-ENHANCED RAMAN SCATTERING

The present invention relates to compounds and markers for surface-enhanced Raman scattering (SERS), and methods for the preparation of the SERS markers. The present invention further relates to compositions, methods and uses, wherein the present SERS markers are employed.

Fluorescence microscopy and fluorescence spectroscopy are among the most widely used optical techniques for the detection of labelled (bio)molecules. The use of fluorophores as external markers has been known for a long time. More recently, quantum dots (QDs)—semiconductor nanocrystals with intense and controlled fluorescence emission—are among the most promising nanostructures for applications not only in the life sciences. Diagnostic applications of QDs include the multiplexed, i.e. parallel, detection of a variety of target molecules. Important areas are the detection of proteins in immunoassays, the detection of neurotransmitters and cellular imaging, see Azzazy (2006) Clinical Chemistry 52, 1238; Jain (2005) Clinica Chimica Acta 358, 37; Rosi (2005) Chemical Reviews 105, 1547. A disadvantage of QDs is the toxicity of the semiconductor material, because compounds such as CdSe, InP/InAs or PbS/PbSe are employed. Quantum dots are well suited as labels in multiplexed applications, i.e. the parallel detection of several target molecules. The number of simultaneously detectable QDs is approximately 3 to 10, which is a significant improvement compared with conventional (organic) fluorophores. Additionally, QDs also possess a much higher photostability compared with conventional fluorophores.

In the life sciences, Raman spectroscopy is currently much less employed in comparison with fluorescence spectroscopy. Recent technological developments (UV/NIR lasers, high-throughput spectrometers, notch filters, CCD cameras) have contributed to an increased use of Raman spectroscopy and microscopy; however, the small differential Raman scattering cross sections of most biological materials—resulting in weak Raman signals—is in many cases disadvantageous. By placing molecules close to metallic nanostructures, the Raman scattering signal can be enhanced by up to 14 orders of magnitude. This type of Raman scattering, which is called surface-enhanced Raman scattering (SERS), has therefore a very high sensitivity. In contrast to fluorescence spectroscopy, photo bleaching of the illuminated substrate is generally not a problem in Raman spectroscopy, because the laser light is inelastically scattered (and, in the absence of electronic resonances, not absorbed). The occurrence of tissue autofluorescence as a competing process, for example, can be minimized by near-infrared (NIR) excitation; autofluorescence can significantly contribute to a decrease in the optical image contrast in fluorescence microscopy, in which excitation in the visible spectral region (Vis) is usually employed.

The most fundamental difference between Raman (vibrational transitions) and fluorescence (electronic transitions) based detection schemes is their intrinsic potential for a multiplexed detection. Raman/SERS approaches have a significantly higher capacity for multiplexing because the line width of Raman bands is approximately 100 times or more smaller as compared to fluorescence emission bands. FIG. 1 shows this effect for three spectrally distinguishable fluorophores in comparison with the conventional Raman spectrum of a single Raman marker, using benzene as an example. The fluorescence emission bands (top spectrum) have a full width at half maximum of about 20 to 50 nm, whereas the Raman bands (bottom spectrum) have a full width at half maximum of typically only about 2 to 20 cm$^{-1}$.

The spectral signature of each Raman marker can be presented as a barcode: wavenumbers of Raman bands are encoded in horizontal line positions, whereas the corresponding intensities are encoded in the width of the line. Multiplexing with Raman/SERS marker implies that many different barcodes are detectable within the same spectral window without or only minimal spectral interferences. Each spectrum or barcode must unambiguously be assigned to the corresponding Raman/SERS marker. If the spectral contributions of different markers start to spectrally overlap, mathematical techniques for signal decomposition have to be applied. Besides simple decomposition approaches, also more elaborate methods such as multivariate analysis and chemometric techniques can or must be used.

Figure 2:
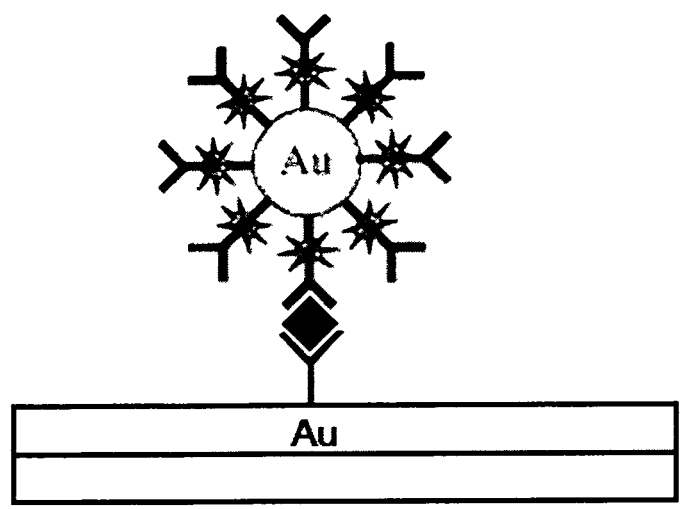

By conjugating Raman markers to antibodies and metallic nanoparticles for SERS, proteins can be detected at very low concentrations, for example, at the femtomolar level; see Rohr (1989) Anal Biochem 182, 388; Dou (1997) Anal Chem 69, 1492; Ni (1999) Anal Chem 71, 4903; Grubisha (2003) Anal Chem 75, 5936; Xu (2004) Analyst 129, 63. The concept of this SERS-immunoassay is depicted in FIG. 2: antigens are detected by the characteristic Raman scattering signal of Raman markers which are covalently attached to an antibody (for biological specificity) and to a nanoparticle (for SERS). The specific interaction between antigen and antibody is used both for immobilizing antigens on the gold coated surface and for capturing the antigen from the solution. Because of the distance dependence of SERS, only Raman bands of the Raman marker, which is close to the gold surface, are selectively enhanced; Raman bands of groups which are further distant from the nanoparticle surface, such as the amide bands of the antibody, are not observed. In addition to immunoassays, imaging of target molecules is a further important application. For example, the first demonstration of this Raman technique has been shown by localizing prostate-specific antigen in the epithelium of prostate tissue section (DE 10 2006 000 775; Schlücker (2006) Journal Raman Spectroscopy, 37, 719). These experiments are the proof of principle of SERS microscopy, μSERS, or Immuno-Raman microspectroscopy.

Various types of SERS markers are known.

In WO 2004/007767 a SERRS active bead for use in identification of a target molecule is described, wherein the SERRS active bead comprises aggregated metal colloid and at least one SERRS active dye, encapsulated within a polymer shell (see also McCabe (2006) Faraday Discussion 132, 303). Employing dye molecules with a strong electronic absorption in the visible spectral region leads to surface-enhanced resonance Raman scattering (SERRS). The detection limit for SERRS is usually lower as compared to SERS, i.e. the sensitivity for SERRS is higher. Due to the presence or absence of electronic resonance conditions, a different enhancement pattern for Raman bands in SERRS and SERS is usually observed. Generally, a larger number of (intense) Raman bands is unfavorable with respect to multiplexing because it can lead to an increased overlap in the corresponding spectral window. Further, the above SERRS beads have a diameter of about 1.0 to 1.5 μm, which is quite large for Raman microspectroscopic experiments with high spatial resolution. Another aspect is the weight of the marker. For specific applications, for example, in tissue diagnostics, an antibody labelled with a Raman/SERS marker has to bind selectively to the corresponding immobilized antigen. This process should not be inhibited or hampered because of the high weight/mass of the SERS marker (=Raman marker plus nanoparticle); for example, a stable antigen-antibody bond has to be formed.

C. A. Mirkin et al. (US 2003/0211488, US 2004/0086897) reported two specific marker types wherein oligonucleotides modified with an alkanethiol moiety and a Raman marker are employed (see also Cao (2002) Science 297, 1536; Cao (2003)eJ Am Chem Soc 125, 14676).

Natan et al. (US 2003/0166297, US 2006/0054506) describe surface-enhanced spectroscopy active composite nanoparticles (SACN) (see also Mulvaney (2003) Langmuir 19, 4784). According to US 2003/0166297, the SACN contains a surface-enhanced spectroscopy active metal nanoparticle, a layer of spectroscopy-active species associated with or in close proximity to the metal surface, and an encapsulating shell made of a polymer, glass or any other dielectric material. According to US 2006/0054506, the SACN comprises a nanoparticle core, a Raman-active reporter molecule, an $SiO_2$ encapsulant, and a reactive group selected from —SH, —$NH_2$ and —$COO^-$. A protein or nucleic acid can be coupled to the reactive group.

Porter et al. (US 2005/0089901) describe a Raman-active reagent comprising a Raman-active reporter molecule, a binding molecule and a surface enhancing particle (for SERS). The Raman-active reporter molecule is chemically linked to the surface enhancing particle. The reactive group is operably linked to the binding molecule, which is capable of specifically binding to a target analyte (see also Ni (1999) Anal Chem 71, 4903; Grubisha (2003) Anal Chem 75, 5936).

Yu et al. (Yu (2007) Bioconjugate Chem 18, 1155) describe fluorescent surface-enhanced Raman spectroscopic dots (F-SERS dots), comprising silver nanoparticle-embedded silica spheres, fluorescent dyes and Raman labels, and a silica-coating that is built upon 3-mercaptopropyltrimethoxysilane (MPTS) which is bound to the silver surface of the nanoparticles together with the Raman labels. F-SERS dots are amino-functionalized and coupled to antibodies for specific targeting.

Kim et al. (Kim (2006) Anal Chem 78, 6967) describe surface-enhanced Raman scattering dots (SERS dots), composed of a silver nanoparticle-embedded silica sphere and a self-assembled monolayer of a Raman label compound and MPTS upon which a silica shell is grown. The SERS dots are functionalized and conjugated to antibodies for cellular targeting.

Jun et al. (Jun (2007) J Comb Chem 9, 237) describe surface-enhanced Raman spectroscopic (SERS)-encoded beads, comprising silver nanoparticle-embedded sulfonated polystyrene beads (5 μm diameter), a Raman label compound and MPTS adsorbed onto the silver nanoparticles, and a silica shell grown upon the MPTS. Antibodies can be conjugated to the SERS-encoded beads.

Each of the previously described SERS markers suffers from one or more of the following disadvantages. Firstly, due to intermolecular interactions and inhomogeneities a large number of enhanced Raman bands can be present in the SERS spectrum leading to overlap of Raman bands which is particularly problematic in case of multiplexing applications. This is true for silica-encapsulated SERS markers in particular, comprising Raman reporter molecules and silica precursor molecules (such as, for example, MPTS) which are co-adsorbed onto the nanoparticle surface in order to allow silica encapsulation of the particle. At the same time, however, said co-adsorption excludes the formation of a self-assembled monolayer consisting essentially of moieties comprising a Raman-active reporter group. As a result, a uniform orientation of the moieties comprising a Raman-active reporter group relative to the nanoparticle surface normal may be difficult to achieve. This may result in an increased number of surface-enhanced Raman signals from different normal modes, making the spectra harder to interpret and less reproducible. Furthermore, the intensity of each Raman band can be relatively low. Secondly, SERS markers having relatively large size and/or weight are inferior in terms of spatial resolution in imaging applications. Further, binding to target molecules can be weak and/or non-selective. Thirdly, in some SERS markers the core particle is densely covered by Raman-active reporter groups in order to attain strong Raman signals. However, in such SERS markers active surface groups for binding to biomolecules are often hardly accessible due to steric hindrance. The binding of biomolecules to the particle surface can thereby be inhibited.

Thus, it is an object of the present invention to provide SERS marker which can overcome one or more of the prior art problems summarized above.

In particular, a problem underlying the present invention is the provision of compounds and SERS markers that allow for a sensitive and highly resolved detection of target structures, both in terms of sensitivity and resolution of the Raman spectrum as well as sensitivity and resolution in the mapping or imaging of target structures. Ideally, the number of Raman bands associated with each Raman-active reporter group should be as low as possible. Thus, the SERS marker should be suitable for multiplexing applications. Further, the SERS marker should preferably exhibit excellent stability in solvents, in particular water, but also be relatively inert against air oxygen. Thus, the SERS marker ideally has a high storage stability.

It has now surprisingly been found that the above identified problems and objects can be solved by the provision of the embodiments characterized in the claims.

Accordingly, the present invention relates in one aspect to a SERS marker comprising a metal particle;
a self-assembled monolayer on the metal particle, the self-assembled monolayer consisting essentially of moieties comprising a Raman-active reporter group Ra and a group X which couples the moiety to the metal particle, wherein X can be comprised in Ra;
an encapsulant surrounding the self-assembled monolayer; and
a group Y which allows coupling of the SERS marker to a binding molecule.

In a preferred embodiment, the SERS markers according to the invention having an encapsulant further comprise a spacer group $Sp^E$ which comprises a linear chain of at least three atoms separating the encapsulant and Y, wherein one terminal end of $Sp^E$ is bound to the outer surface of the encapsulant and the other terminal end of $Sp^E$ is bound to the group Y.

Furthermore, it is preferred that, the self-assembled monolayer of the SERS markers according to the invention having an encapsulant consists essentially of moieties comprising the structure (IIIa)

X~Ra                                (IIIa)

which is particularly preferably a linear structure.

The present invention relates in a further aspect to a SERS marker comprising a metal particle; and
a self-assembled monolayer on the metal particle, the self-assembled monolayer consisting essentially of
moieties comprising the linear structure (Ia)

X~Ra~Sp~Y                           (Ia)

wherein
X is a group coupling the moiety comprising structure (Ia) to the metal particle, wherein X can be comprised in Ra;
Ra is a Raman-active reporter group;
Sp is a spacer group comprising a linear chain of at least three atoms separating Ra and Y, and Y is a group which allows coupling of the moiety comprising structure (Ia) to a binding molecule, and moieties comprising the linear structure (IIa)

$$X\sim Ra\sim Sp^*\sim Y \quad \text{(IIa)}$$

wherein

X is a group coupling the moiety comprising structure (IIa) to the metal particle, wherein X can be comprised in Ra;

Ra is a Raman-active reporter group;

Sp* is a spacer group which can be absent, and

Y is a group which allows coupling of the moiety comprising structure (IIa) to a binding molecule and wherein Y can be absent, provided that the linear chain of atoms in Sp which separates Ra and Y in the moiety comprising structure (Ia) is at least three atoms longer than the linear chain of atoms in Sp* which separates Ra and Y in the moiety comprising structure (IIa).

Further, in a herein disclosed embodiment the present invention relates to a SERS marker comprising a metal particle;

a self-assembled monolayer on the metal particle, the self-assembled monolayer comprising moieties comprising a Raman-active reporter group Ra and a group X which couples the moiety to the metal particle, wherein X can be comprised in Ra;

an encapsulant surrounding the self-assembled monolayer, the encapsulant comprising one or more polymer layers and an additional encapsulant layer comprising silica, wherein the one or more polymer layers are present on the outer surface of the self-assembled monolayer, and further wherein the additional encapsulant layer comprising silica is present on the outer surface of the outermost of the one or more polymer layers; and a group Y which allows coupling of the SERS marker to a binding molecule.

In a preferred embodiment, the SERS markers according to the invention having an encapsulant further comprise a spacer group $Sp^E$ which comprises a linear chain of at least three atoms separating the encapsulant and Y, wherein one terminal end of $Sp^E$ is bound to the outer surface of the encapsulant and the other terminal end of $Sp^E$ is bound to the group Y.

In a preferred embodiment, the SERS markers according to the invention having an encapsulant surrounding the self-assembled monolayer, the encapsulant comprising one or more polymer layers on the outer surface of the self-assembled monolayer and an additional encapsulant layer comprising silica on the outer surface of the outermost of the one or more polymer layers, the outermost of the one or more polymer layers comprises poly(vinylpyrrolidone).

It has further surprisingly been found that the SERS markers disclosed herein can have additional advantageous features as compared to markers known in the prior art. For example, the formation of a self-assembled monolayer (SAM) from the moieties comprising a Raman-active reporter group Ra, wherein the self-assembled monolayer covers the whole surface of the metal particle, is advantageous since the uniform molecular orientation of the moieties, specifically the orientation relative to the metal particle surface normal, results in a maximum SERS enhancement of only few Raman bands observed in the SERS spectrum. This will lead to particularly narrow and reproducible Raman bands from only a small number of normal modes. Accordingly, the SERS markers of the invention exhibit a very high multiplexing capacity. Moreover, a self-assembled monolayer which covers the whole surface of the metal particle and consists essentially of moieties comprising a Raman-active reporter group may allow a constantly high SERS (or SERRS) sensitivity between separate SERS markers of the same composition. This is particularly advantageous in terms of reproducibility. In addition to reducing the number of Raman bands and the corresponding increase in signal intensity, which are properties that are very important in terms of multiplexing, the SAM covering the complete surface of the metal particle provides further advantages. Accordingly, the SERS markers may have a reduced tendency to aggregate, since binding molecules should be prevented from binding or adsorbing directly to the surface of the metal particle. This is particularly advantageous in those embodiments that do not comprise an encapsulant.

Further, the spacer groups employed in some embodiments of the SERS markers disclosed herein can prevent or minimize steric hindrance when binding molecules are to be bound to a moiety comprised in the SERS marker. Thus, a defined amount and number of binding molecules may bind to said moieties. Binding of a defined amount of binding molecules per surface unit of a SERS marker is advantageous in several ways:

Firstly, results obtained using SERS markers uniformly covered with binding molecules are more reproducible since a given amount of SERS markers comprises a corresponding, constant amount of binding molecules which may be used in the detection of target molecules. Thus, the use of SERS markers of the invention can facilitate the standardization of laboratory protocols and the comparability of results obtained. Accordingly, the SERS markers of the present invention are particularly advantageous when a standardized quantification of target molecules is desired.

Secondly, the spacer groups comprised in the SERS markers disclosed herein may prevent the undesired aggregation of several SERS markers. Such an aggregation can lower the quality of data obtained when SERS markers are used in the detection of target molecules.

Thirdly, the spacer groups may prevent the SERS markers from unspecific binding to other molecules than the target molecules.

The use of spacer groups having different lengths can provide further advantages. For example, varying the length of spacer groups or varying the percentage of spacer groups bound to a group Y (allowing coupling of the SERS marker to a binding molecule) can minimize or prevent sterical hindrance of binding molecules. For example, shorter moieties comprised in the SERS marker may not comprise said group Y whereas longer moieties may comprise said group Y. The binding of a defined number of binding molecules may be controlled by varying the molar ratio of shorter and longer moieties comprised in a SERS marker. By varying the above-mentioned parameters, the Y group of the moiety comprised in the SERS marker may be easier accessible to binding molecules. Thus, moieties comprised in a SERS marker which comprise spacer groups of different lengths can allow for a controlled binding of a defined number of binding molecules to the Y group. Of course, varying the ratio of spacers of different lengths comprised in the SAM or on the encapsulant surface may also minimize or prevent sterical hindrance of binding molecules.

In those embodiments, wherein the SERS marker comprises an encapsulant, further advantages may be observed. Accordingly, encapsulation may minimize or even eliminate particle aggregation of SERS markers and desorption of moieties comprising Raman-active reporter groups from the metal surface, providing both chemical and mechanical stability. Further advantageous properties imparted by the encapsulant can be an increased water solubility and long-term storage stability of the SERS marker. In the invention, these advantages of encapsulation are integrated with the above mentioned advantages of a complete self-assembled monolayer of moieties comprising a Raman-active reporter group in a single functional unit, i.e. an encapsulated SERS marker comprising a complete self-assembled monolayer of moieties comprising a Raman-active reporter group.

The metal particle in the present SERS markers may be a single particle or may comprise a plurality of particles, i.e. an assembly of particles. Preferably, the single particle and the plurality of particles constitute a nanoparticle. The term "nanoparticle" in the context of the present invention means a particle which preferably has a size (spherical particles: diameter; otherwise: length) of about 1 nm to about 400 nm, more preferably of about 5 nm to about 200 nm, even more preferably of about 10 nm to about 120 nm, and most preferably from about 20 nm to about 100 nm. The assembly of nanoparticles may, for example, comprise at least 2, 3, 5, 10, 15 or 20 nanoparticles. The use of single nanoparticles can be preferred in the case of imaging applications since single nanoparticles may be advantageous in terms of high spatial resolution and multiplexing due to their smaller size as compared to large assemblies of nanoparticles. The nanoparticle of a SERS marker for use in imaging applications preferably has a size of about 1 nm to about 200 nm, more preferably of about 1 nm to about 100 nm, even more preferably of about 5 nm to about 60 nm, and most preferably of about 10 nm to about 40 nm. An assembly of nanoparticles, on the other hand, may exhibit enormous SERS or SERRS enhancements (e.g. for molecules at the junctions of the nanoparticles) upon plasmon excitation. Thus, the use of assemblies of nanoparticles can be preferred when high sensitivities are desired. An assembly of nanoparticles can, for example, be prepared chemically. Examples are micro/nanoemulsions, solid-phase supported chemistry, and template-based approaches. Alternatively, the assemblies can be prepared mechanically, for example by nanomanipulation. Such methods are known to persons skilled in the art and are described, for example, in Baur, Nanotechnology (1998) 9, 360; Worden, Chemistry of Materials (2004) 16, 3746; Zoldesi, Advanced Materials (2005) 17, 924; and Kim, Analytical Chemistry (2006) 78, 6967.

It is preferred that the particles and nanoparticles have a uniform (relatively monodisperse) size distribution. In the context of this invention, the term "uniform size distribution" means that the relative standard deviation with respect to the average size of (nano)particles employed herein is less than 50%, 20% or 10%. Most preferably the relative standard deviation is less than 5%. A person skilled in the art knows how to determine the average size of (nano)particles and the respective relative standard deviation.

In another preferred embodiment, the metal particle comprises only one (nano)particle. This embodiment allows for a particularly rigid quantification. Preferably the size of said one nanoparticle ranges from about 1 nm to about 200 nm. More preferably the size of said one nanoparticle ranges about 5 nm to about 120 nm, and even more preferably about 10 nm to about 100 nm. Most preferably, the size of said one nanoparticle ranges about 30 nm to about 80 nm. Methods for the preparation of such metal nanoparticles are known in the art and are described, for example, in Aroca, Surface-enhanced Vibrational Spectroscopy, Wiley, 2006.

Coinage metals such as silver (Ag), gold (Au), or copper (Cu) or alloys thereof are known for their large SERS enhancement. Thus, in a preferred embodiment the metal particle comprises a metal selected from Ag, Au and Cu or alloys thereof. Generally, the metal particle employed herein may comprise any metal, alloys thereof and/or any other material which exhibits a (large) SERS enhancement. For example, Na, K, Cr, Al, Li, alloys thereof and alloys thereof with any of the above coinage metals may be used. Further, it is preferred that the plasmon resonance of the metal particle occurs between 300 nm and 1500 nm. In particular, the visible (400 nm to 750 nm) to near-infrared (750 nm to 1 μm) spectral region is preferred. The region 620 nm to 1500 nm is most preferred. Here, autofluorescence of biological specimen, which decreases the image/signal contrast, can be minimized. Also, tissue is relatively transparent in this spectral region ("biological window", for example, for in vivo applications).

Figure 12:
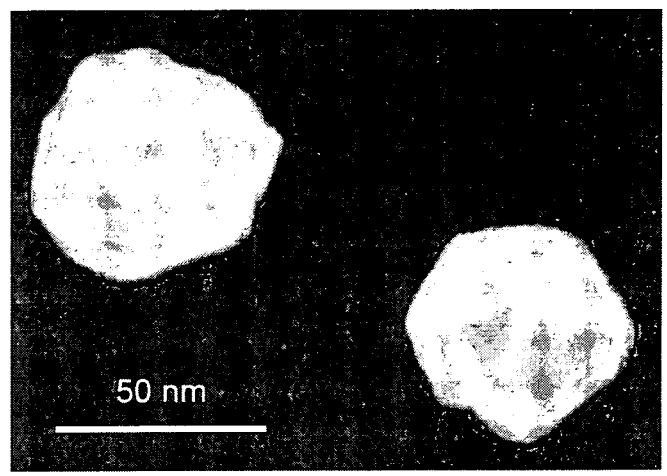

Single particles may be spherical or non-spherical. Examples for spherical particles are solid spheres, core-shell particles and hollow spheres. Hollow nanoparticles are also referred to as nanoshells. Such hollow nanoshells are shown in FIG. 12 and have been used in appended Examples 2 and 5. Nanoshells can be preferable in terms of SERS sensitivity as compared to solid spheres as shown in Example 9. Further, nanoshells may be preferable when laser excitation in the red to near-infrared (NIR) spectral region is employed. Non-spherical particles may be, inter alia, rods/ellipsoids, toroids, triangles, cubes, stars and fractal geometries. The use of said non-spherical particles may be preferred over spherical particles since non-spherical geometries lead to large electromagnetic field enhancements because of the high curvature radius. Thus, non-spherical particles can achieve particularly high sensitivity. Spherical particles provide the advantage of a high symmetry, i.e. all molecules in the SAM experience can experience the same enhancement, i.e. the same increased local electromagnetic field. Thus, spherical particles can be preferred when the application at hand focuses on a rigid quantification.

Moreover, the particles may be composite particles formed from combinations of different materials including a metal. Examples thereof are particles of the core-shell type wherein a metal shell, preferably a shell of Ag, Au or Cu, is present on a non-metallic core, e.g. a core of a metal oxide or a non-metal oxide, such as alumina, titanium dioxide or silica.

The term "self-assembled monolayer" (SAM) is known in the art (cf. for example Kriegisch (2005) Top Curr Chem 258, 257; Love, Chemical Reviews (2005) 105, 1103; Daniel, Chemical Reviews (2004) 104, 293; Li, Journal of Materials Chemistry (2004) 14, 2954; Weisbecker, Langmuir (1996) 12, 3763). Herein, the term "self-assembled monolayer" (SAM) is used to denote a layer which forms spontaneously when the metal particle or metal surface and compounds forming the SAM are mixed under suitable conditions. SAMs typically provide a single layer of molecules on the surface of substrates, such as metal particles. They can often be prepared simply by adding a solution of the desired molecule onto the substrate and washing off the excess. The formation of SAMs has been previously described. For example, Kriegisch (2005) Top Curr Chem 258, 257 describes the spontaneous formation of a SAM of alkyl or aryl thioles and disulfides (as precursors) on gold (and other metal) surfaces. SAMs can provide a uniform coverage of the complete surface of the metal particle. Exemplary well-defined and uniform SAMs are shown in Examples 2, 4 and 5 and in FIGS. 3, 5 and 6. A uniform coverage of the metal particle may be advantageous with respect to quantification of Raman intensities. Quantification may, for example, be achieved by spectrally resolved detection and direct labelling (in the case of proteins: labelling of the primary antibody) in combination with reference experiments (for example, using known target molecule concentrations in immunoassays). The similar or even same molecular orientation of molecules within the SAM is very advantageous for multiplexed applications, because only selected Raman bands are observed in the spectrum (SERS selection rules, see for example Creighton in: Clark, Hester (Eds.) Advances in spectroscopy: spectroscopy of surfaces, Vol. 6, pp. 37, Wiley, 1988; Smith, Modern Raman Spectroscopy, Wiley, 2005) and an unwanted overlap of spectral contributions by a distinct moiety comprised in the SERS marker is minimized. Because the Raman intensity is proportional to the number of molecules, the formation of a SAM is also advantageous in terms of the detection limit (high sensitivity): a SAM has a large number of Raman-active reporter groups comprised in the SERS marker per unit surface area. In addition, complete coverage of the metal particle by a SAM inhibits a direct adsorption of (bio)molecules to the particle surface.

As set out above, the term "self-assembled monolayer" as used herein typically denotes a layer formed by molecules which assemble in the form of a monolayer on a metal particle and adhere to its surface, generally due to adsorption phenomena. The term "moiety", as used in the same context herein, refers to a sub-unit of the self-assembled monolayer formed by one molecule adhering to the surface of the metal particle.

Figure 3:
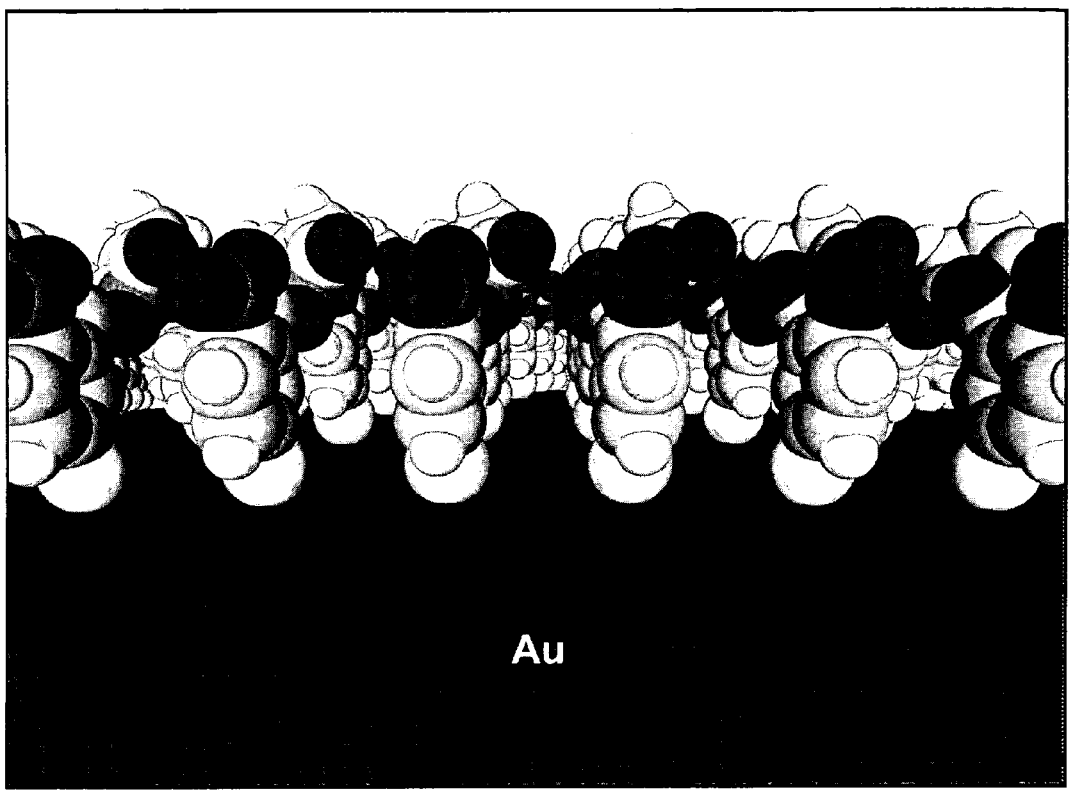
Figure 6:
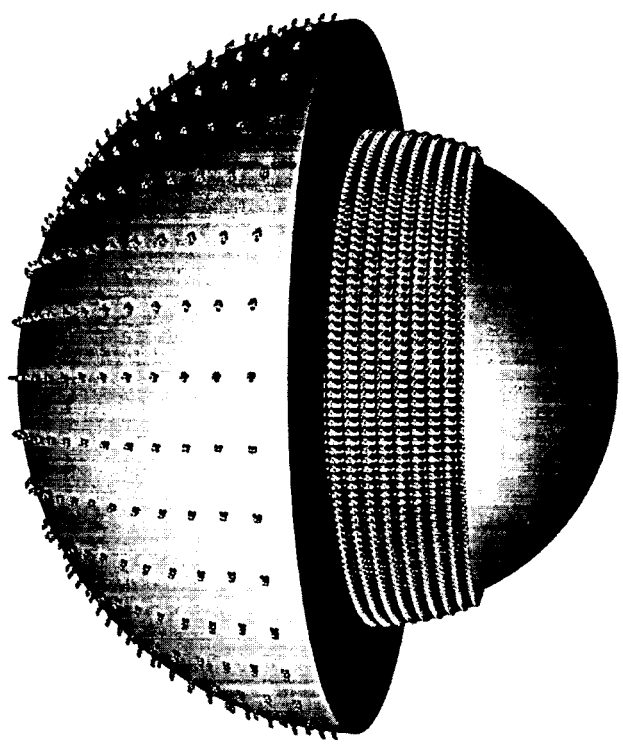

It has been found advantageous for the SERS markers according to the invention to comprise a self-assembled monolayer on a metal particle, the self-assembled monolayer consisting essentially of moieties comprising a Raman-active reporter group Ra and a metal-binding group X which can be comprised in Ra. Exemplary self-assembled monolayers consisting essentially of moieties comprising a Raman-active reporter group Ra and a metal-binding group X are shown in FIGS. 3 and 6.

The term "self-assembled monolayer consisting essentially of moieties comprising a Raman-active reporter group Ra" generally denotes a coverage of the metal particle with the respective moietie(s) of at least 85%, preferably at least 90%, more preferably at least 95%, even more preferably at least 99%, and most preferably 100%, relative to the maximum coverage which is obtained when a SAM is formed solely of the respective moietie(s). The maximum coverage can be determined, e.g., by monitoring the development of the SERS signal of metal particles over time during the adsorption process of the molecules forming the moieties under consideration. A constant SERS signal level in a SERS intensity (y) vs. time (x) diagram, i.e. a plateau in the SERS signal, corresponds to a maximum coverage of the metal particle with the respective moieties and forms the reference signal. A particle yielding a certain percentage of this maximum SERS signal is considered herein to be covered by the respective moieties at this percentage level, as described in more detail below. It is to be noted that this definition of a surface coverage relative to the maximum surface coverage has been chosen herein due to the convenient accessibility of the analytical data required for its determination. Thus, the requirement that the self-assembled monolayer consists essentially of moieties comprising a Raman-active reporter group Ra is also fulfilled if at least 85%, preferably at least 90%, more preferably at least 95%, even more preferably at least 99%, and most preferably 100% of all moieties forming the SAM (in terms of numbers of these moieties) comprise a Raman-active reporter group. This can be verified by conventional methods of chemical analysis of the composition of the SAM as they are known in the art.

Herein, the term "self-assembled monolayer consisting essentially of moieties comprising a Raman-active reporter group Ra" is used interchangeably with "complete self-assembled monolayer of moieties comprising a Raman-active reporter group Ra". Thus, the term "complete self-assembled monolayer of moieties comprising a Raman-active reporter group Ra" denotes a coverage of the metal particle with the respective moietie(s) of at least 85%, preferably at least 90%, more preferably at least 95%, even more preferably at least 99%, and most preferably 100%, relative to the maximum coverage which is obtained when a SAM is formed solely of the respective moietie(s).

As noted above, various methods can be used to determine the content of moieties comprising a Raman-active reporter group Ra in a self-assembled monolayer. For example, a simple SERS experiment can be used. In this type of experiment, a colloidal solution of blank (unfunctionalized) metal nanoparticles is incubated solely with molecules comprising a Raman-active reporter group Ra and a metal-binding group X', leading to the formation of the corresponding SERS marker. The Raman signal of the formed SERS marker (y-axis) is then measured as a function of the incubation time (x-axis), i.e. the reaction time between the metal nanoparticle and the molecules containing a Raman-active reporter group Ra and a metal-binding group X'. It will be understood that this measurement is usually carried out at a single characteristic frequency where the Raman spectrum of the Raman-active reporter group under consideration provides a peak. Generally, the SERS signal increases with an increasing number of Raman-active reporter groups on the metal surface. The exact shape of the SERS intensity (y) vs. time (x) diagram may vary, depending on the individual reaction conditions. Usually, a rapid increase of the SERS intensity for short times is observed, while for longer times the slope decreases. Often, the slope converges to zero. This constant SERS level, i.e. a plateau in the SERS intensity ($I_{max}$), indicates that a self-assembled monolayer consisting solely of moieties comprising a Raman-active reporter group Ra has been formed. The constant SERS level thus corresponds to a maximum coverage of the metal nanoparticle with moieties comprising a Raman-active reporter group. An exemplary description of this type of SERS experiment is given in Example 6. For any given moiety containing a Raman-active reporter group, its content in a SERS marker according to the invention may thus be conveniently determined by obtaining the relationship $I_{ex}/I_{max}$ between the actual intensity $I_{ex}$ of the Raman signal measured for the SERS marker under consideration and the reference value $I_{max}$ obtained as set out above for SERS markers covered with a SAM consisting of the Raman-active reporter group under consideration.

If the Raman signal ($I_{ex}$) thus measured is 85%, preferably 90%, more preferably 95%, even more preferably 99%, most preferably 100% of the maximum level of SERS intensity determined above, i.e. if the quotient $(I_{ex})/(I_{max})$ is 0.85 or more, preferably 0.9 or more, more preferably 0.95 or more, even more preferably 0.99 or more, and most preferably 1, a self-assembled monolayer consisting essentially of moieties comprising the respective Raman-active reporter group Ra is present on the metal particle. It will be understood that the signal $I_{ex}$ and the signal $I_{max}$ would have to be obtained under comparable conditions e.g. with respect to the average size and the amount of adsorbing particles. In cases where a SAM contains two or more different Raman active reporter groups contained in different moieties, their contents can be determined individually, each one in relationship to the maximum coverage that would be obtainable for the given moiety. The overall (relative) content of moieties containing a Raman-active reporter group can be calculated as the sum of the relative contents.

Alternatively, the presence of a complete self-assembled monolayer on the metal surface, and also the presence of a self-assembled monolayer consisting essentially of moieties comprising a Raman-active reporter group Ra, can be determined by determining first the required space of a single moiety comprised in a SAM, then the maximum possible number of moieties comprising Ra on the surface of a nanoparticle, and subsequently the amount of molecules that constitute the SAM of a single nanoparticle. In order to determine the required space of a single moiety comprised in the SAM, a SAM of a specific moiety comprising a Raman-active reporter group Ra and a metal-binding group X is formed on a flat metal surface and this sample is analyzed by surface-selective methods such as scanning tunneling microscopy (STM) or atomic force microscopy (AFM). With high-resolution STM/AFM experiments the intermolecular spacing between the moieties in a SAM can be visualized. Thus, the required space of this specific moiety in a SAM can be determined. Then, the maximum possible number of moieties comprising Ra bound to the surface of a nanoparticle with known surface area can be calculated. A person skilled in the art knows how to determine the surface of a nanoparticle. Having determined the required space of a single moiety comprised in a SAM and the maximum possible number of moieties on the surface of a nanoparticle, the amount of moieties in the SAM on a single nanoparticle can be determined via thermogravimetric analysis (TGA). The principle of this method is to measure the temperature-dependent change in mass of the sample. A sample of SAM-functionalized nanoparticles is heated on a high-precision balance, ideally under inert gas atmosphere. Organic molecules vaporize at much lower temperature than metals. Approximately at their boiling point or point of thermal degradation, the organic molecules vaporize off the nanoparticle surface leading to a measurable loss of mass. For an identification and quantification of the composition of the SAM, the vapor can be further analyzed. Mass spectrometry or Fourier transform infrared spectroscopy can be applied. Coupled gas chromatographic and mass spectrometric techniques may also be employed for a separate analysis of a mixture of different compounds constituting a SAM. With the known mass of a single nanoparticle the number of compounds constituting a SAM can be calculated per particle. Typically, the number of molecules constituting a SAM is in the range of 15 000 to 67 000 (or up to 68 000) for a 50 nm nanoparticle. Further, an elementary analysis based on high-resolution x-ray photoelectron spectroscopy (HRXPS) may be used.

The approaches disclosed by Natan et al. (US 2003/0166297, US 2006/0054506, U.S. Pat. No. 6,514,767) and Mirkin et al. (US 2003/0211488, US 2004/0086897) do not yield a complete self-assembled monolayer (SAM) consisting essentially of moieties comprising Raman marker molecules, in which the Raman marker molecules are uniformly oriented on the surface. Due to the lack of a well-defined orientation, Raman marker molecules can assume different orientations with respect to the nanoparticle surface: for example tangentially or parallel to the surface normal. Different geometrical orientations can be detected by the Raman intensities of certain bands in the SERS spectrum. The non-uniform orientation of surface molecules leads to the detection of a larger number of enhanced Raman bands in the SERS spectrum compared with the presence of a uniform SAM. In Example 8, the SERS spectra of both a SERS marker comprising a complete self-assembled monolayer of moieties comprising Raman marker molecules and a SERS marker comprising a submonolayer as regards the moieties comprising Raman marker molecules—i.e. a monolayer wherein moieties comprising Raman marker molecules cover less than 85% of the metal particle, relative to the maximum coverage which is obtained when a SAM is formed solely of said moieties comprising Raman marker molecules—are shown, depicting the effects described above. The low/minimal number of selectively enhanced Raman bands in the case of a uniform SAM is very favorable for a multiplexed detection; for excessive multiplexing, i.e. the parallel detection of a large number of target molecules by Raman/SERS markers, it is considered to be essential. Further, in the case of a SAM the surface coverage and therefore the corresponding SERS signal should be maximal.

The symbol "~" denotes the order of subgroups in a given moiety. For example, in structure (Ia), Ra is connected to Y via Sp. Likewise, in the structure (IIa), Ra is connected to Y (if present) via Sp* (if present). "~" can be equal to a covalent bond. "~" can also represent a bivalent or multivalent chemical group. It will further be understood, that the moieties and compounds comprising structures (Ia), (IIa), (IIIa), (I), (II) and (III) can contain further subgroups in addition to those shown in structures (Ia), (IIa), (IIIa), (I), (II) and (III), respectively. In particular, moieties and compounds are envisioned which comprise two or more Raman-active reporter groups, two or more spacers and/or two or more groups which allow binding of the SERS marker to a binding molecule. For example, the present invention includes embodiments wherein the self-assembled monolayer comprises moieties comprising the following structure:

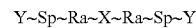

wherein the two groups Y, the two groups Sp, and the two groups Ra, respectively, can be different or, preferably, identical; or moieties comprising the following structure:

wherein the two groups Ra can be different or, preferably, identical.

X comprises preferably a sulfur atom or a nitrogen atom. X can be comprised in the group Ra, for example Ra can be a nitrogen containing heteroaryl group with the nitrogen being X.

The variable X denotes herein a group that couples moieties comprising a Raman-active reporter group Ra to the metal particle and is comprised in moieties constituting the self-assembled monolayer on the metal surface, see structures (Ia), (IIa) and (IIIa). The group X', in contrast, is comprised in the molecules that are adsorbed to the metal particle in the process of forming the SERS markers disclosed herein, see structures (I), (II) and (III). The fact that the group X' may undergo a change during the adsorption process is reflected in the use of two different variables for the respective position of the free and the adsorbed molecules/moieties. Thus, X is a group resulting from X' when a compound comprising structure (I), (II) or (III) is coupled to the metal particle.

X' allows coupling of the compounds comprising structures (I), (II) and (III), respectively, to the metal particle and can be comprised in Ra. In a preferred embodiment of the invention said coupling may be achieved via a chemisorption type interaction, i.e. the bonding strength between X and the metal particle is larger than about 50 kJ/mol. Weaker physisorption type interactions are, however, also envisioned. The coupling between X' and the metal particle can result in a covalent bond, a non-covalent bond, for example by van der Waals forces, or a bond which has properties therebetween. Binding of the compounds comprising structures (I), (II) and (III) to the metal particle may be performed as shown in Examples 2, 4 and 5.

Preferably, X' is a thiol group, a disulfide group, an amino group or a nitrogen atom. When X' is a disulfide group the compound comprising structure (I) can be a dimer of two identical subgroups each comprising structure (I). When X' is a thiol group, it can be part of a cyclic 1,2-dithiolane group, such as a six-membered ring 1,2-dithiolane group. In this embodiment, Ra can be bound to one or more methylene units of the 1,2-dithiolane group. Alternatively, two or more groups Ra can be present in the compound comprising structure (I), each being attached to one or more methylene units of the 1,2-dithiolane group. When X' is a nitrogen atom, it can be part of a heteroaryl group, the heteroaryl group being comprised in the Raman-active reporter group Ra.

The Raman-active reporter group Ra preferably has a unique Raman spectral signature. Most preferably, Ra shows at least one Raman band at a spectral position, at which other Raman-active reporter groups comprised in the SERS marker have no signal contributions. It is preferred that the signals are SERS (surface enhanced Raman scattering) or SERRS (surface enhanced resonance Raman scattering) amplified. Without being bound by theory one main condition for the SERS/SERRS amplification of the signal is the close vicinity of the Raman-active reporter group to the metal particle. The rapid decrease of the SERS signal with distance to the metal surface is also known as the SERS distance dependence (Aroca, Surface-enhanced Vibrational Spectroscopy, Wiley, 2006). Usually, SERS signals within a distance of about 10 nm from the metal surface are observed.

Generally, it is preferred that Raman signals exhibit large intensities. Preferably, the Raman-active reporter group (Ra) has a large differential Raman scattering cross section. One criterion for this is, for example, the polarizability $\alpha$ of Ra. In Raman scattering, the incoming electrical field of the laser E induces, via the polarizability $\alpha$ of Ra, a dipole moment $\mu$: $\mu = \alpha E$. Both $\mu$ and E are vectors, whereas $\alpha$ is a tensor of rank 2. For the observation of SERRS, the molecules should additionally possess a strong electronic absorption (same condition as for the resonance Raman effect) at or nearby the laser excitation wavelength. In addition to a purely electromagnetic mechanism, also chemical effects can contribute to the enhancement of the SERS/SERRS signal.

Furthermore, the self-assembled monolayers of the SERS markers disclosed herein can comprise one single type of Raman-active reporter group Ra or two or more different types of Raman-active reporter groups. This embodiment can be particularly useful for multiplexing applications wherein a large number of diverse SERS markers are required.

In a preferred embodiment, Ra comprises a $C_{2-80}$, preferably $C_{3-60}$, more preferably $C_{4-30}$, even more preferably $C_{6-20}$, and even more preferably $C_{8-15}$ hydrocarbon group, wherein one or more carbon atoms can be replaced by oxygen, nitrogen or sulphur. This group preferably comprises an aromatic group, a carbon-carbon double bond and/or a carbon-carbon triple bond. More preferably, Ra comprises an optionally substituted polyene, polydiacetylene, polyyne, aryl or heterocyclic group. Ra may comprise at least one isolated (carbon-carbon) double and/or at least one isolated (carbon-carbon) triple bond. Accordingly, Ra may comprise, for example, an alkene group or an alkyne group. Ra may also comprise groups containing conjugated (carbon-carbon) double and/or (carbon-carbon) triple bonds. Non-limiting examples of groups containing conjugated (carbon-carbon) double and/or (carbon-carbon) triple bonds are polyenes, polydiacetylenes, polyynes and aromatic groups, such as aryl groups and heteroaryl groups. In the heteroaryl groups one or more, preferably one to three, carbon atoms are replaced by N, O or S, Non-limiting examples of aryl groups are phenyl, naphthyl, anthracenyl and phenantrenyl and their derivatives. Non-limiting examples of heteroaryl groups are pyrrolidinyl, tetrahydrofuranyl, tetrahydrothiophenyl, piperidinyl, pyrrolyl, furanyl, thiophenyl, pyridinyl, pyridazinyl, pyrimidinyl, pyrazinyl, triazinyl, tetrazinyl, quinolinyl and indenyl. Ra may also comprise biological systems with $\pi$-electrons. Accordingly, Ra may comprise a terpene, a terpenoid, a carotenoid or a derivative thereof. A further non-limiting example of such biological systems are porphyrins and derivatives thereof. In a particularly preferred embodiment, Ra has an internal (local) symmetry leading to a reduction in the number of Raman bands (for example, a local center of inversion for a conjugated polyene, in which the terminal substituents at the carbon chain are neglected for symmetry considerations). In particular conjugated polyenes such as carotenoids (or other terpenes) or polydiacetylenes have only very few but very intense Raman bands. A siloxane group or a thiol group does not qualifiy as a Raman-active reporter group according to the invention.

In a very preferred embodiment, Ra has an electronic absorption in the visible (VIS) to near-infrared spectral region (about 400 nm to about 1300 nm). This leads to surface-enhanced resonance Raman scattering (SERRS), in which the electronic resonance condition for both Ra (electronic absorption) and the nanoparticle (plasmon resonance) is fulfilled. Signal levels in SERRS are generally higher than those observed in electronically off-resonant SERS (Aroca, Surface-enhanced vibrational spectroscopy, Wiley, 2006). The above-mentioned conjugated $\pi$-electron systems exhibit electronic transitions from the ultraviolet (UV) to the near-infrared (NIR) region of the electromagnetic spectrum, depending on various parameters such as chain/conjugation length, number and type of substituents, etc. (Hesse/Meier/Zeh, Spektroskopische Methoden in der organischen Chemie, Thieme, 1991). The electronic absorption maximum of a Raman reporter molecule can be taken from the literature, be determined experimentally, or be estimated with the help of tabulated values and known increments for different units (e.g. increments for each conjugated double bond, for each auxochromic group, etc.). Details can, for example, be found in Hesse/Meier/Zeh, Spektroskopische Methoden in der organischen Chemie, Thieme, 1991.

Figure 4:
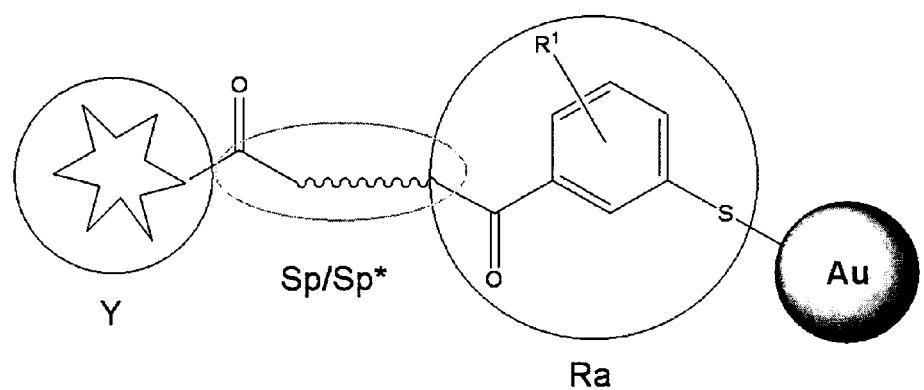

The selection rules for SERS (Creighton, In: Clark, Hester (Eds.) Advances in spectroscopy: spectroscopy of surfaces. Vol 6, pp 37, Wiley, 1988) predict that vibrations scattering via $\alpha_{zz}$, i.e. via the zz-component of the polarizability tensor $\alpha$, experience a very strong enhancement. Therefore, when Ra comprises, for example, an aromatic group bound to the metal particle via group X, substituents in para position with regard to X with a high polarizability in z direction are well suited for obtaining high SERS intensities. Thus, in one preferred embodiment Ra comprises an aromatic group, preferably a phenyl group, having a substituent in the para-position with respect to X, wherein X comprises a sulfur atom, preferably wherein X is a sulfide group. For example, the nitro moiety (for example, in thio-para-nitrobenzene) exhibits a strong SERS band due to the symmetric stretching vibration. Accordingly, aromatic groups with substituents $R^1$ in para position (as shown in FIG. 4) to the sulfur atom are preferred, while, in a less preferred embodiment of the present invention, substituents in ortho and meta position may also be used.

The possibilities for different Raman-active reporter groups arising from the use of different substituents and various substitution patterns are enormous. For example, Ra may comprise one or more substituents selected from halogen, $NO_2$, CN, NC, $OC(O)$—$C_{1-4}$ alkyl, $NHC(O)$—$C_{1-4}$ alkyl, $NR^1_2$ ($R^1$=$C_{1-4}$ alkyl or $C_{6-10}$ aryl), $BF_3^-$, $SiR^2_3$ ($R^2$=$C_{1-4}$ alkyl, $C_{6-10}$ aryl or F), $PR^3_3$ ($R^3=C_{1-4}$ alkyl, $C_{6-10}$ aryl or $C_{1-4}$ alkoxy), $C_{1-4}$ perfluoroalkyl, $C_{1-4}$ alkyl, $C_{6-10}$ aryl, $C_{1-4}$ alkoxy, $C_{1-4}$ alkenyl, and $C_{1-4}$ alkynyl.

It is particularly envisaged that Ra may comprise in addition to a first substituent as described herein above at least one further substituent selected from halogen, $NO_2$, CN, NC, OC(O)—$C_{1-4}$ alkyl, NHC(O)—$C_{1-4}$ alkyl, $NR^1_2$ ($R^1=C_{1-4}$ alkyl or $C_{6-10}$ aryl), $BF_3^-$, $SiR^2_3$ ($R^2=C_{1-4}$ alkyl, $C_{6-10}$ aryl or F), $PR^3_3$ ($R^3=C_{1-4}$ alkyl, $C_{6-10}$ aryl or $C_{1-4}$ alkoxy), $C_{1-4}$ perfluoroalkyl, $C_{1-4}$ alkyl, $C_{6-10}$ aryl, $C_{1-4}$ alkoxy, $C_{1-4}$ alkenyl, and $C_{1-4}$ alkynyl.

As described herein above, Ra may comprise, for example, an aromatic group. By variation of the aromatic skeleton of Ra and/or the introduction of at least one additional substituent in addition to a first substituent, a large variety of bifunctional (or higher functional) Raman-active reporter groups can be obtained. The additional substituent shifts the wavenumber position of a characteristic Raman band of the first substituent, for example by influencing the electronic structure of the marker unit. For example, various substitution patterns with a substituent in ortho or meta position to the sulfur atom as shown in FIG. 4 may result in a variety of Raman-active reporter groups. These may be used in combination, for example in multiplexing applications.

Preferably, a Raman-active reporter group Ra has a Raman spectrum at a wavelength of 514.5 nm wherein the most intense Raman band has a differential Raman cross section β of at least $6·10^{30}$ cm$^2$ sr$^{-1}$ molecule$^{-1}$, more preferably at least $8·10^{30}$ cm$^2$ sr$^{-1}$ molecule$^{-1}$ and most preferably at least $45·10^{30}$ cm$^2$ sr$^{-1}$ molecule$^{-1}$, as defined in Raman Spectroscopy for Chemical Analysis, R. L. McCreery, Wiley Chemical Analysis Series, Vol. 157, J. Winefordner, ed., 420+xxiv pages, John Wiley, NY, 2000, ISBN 0-471-25287-5.

Figure 5:
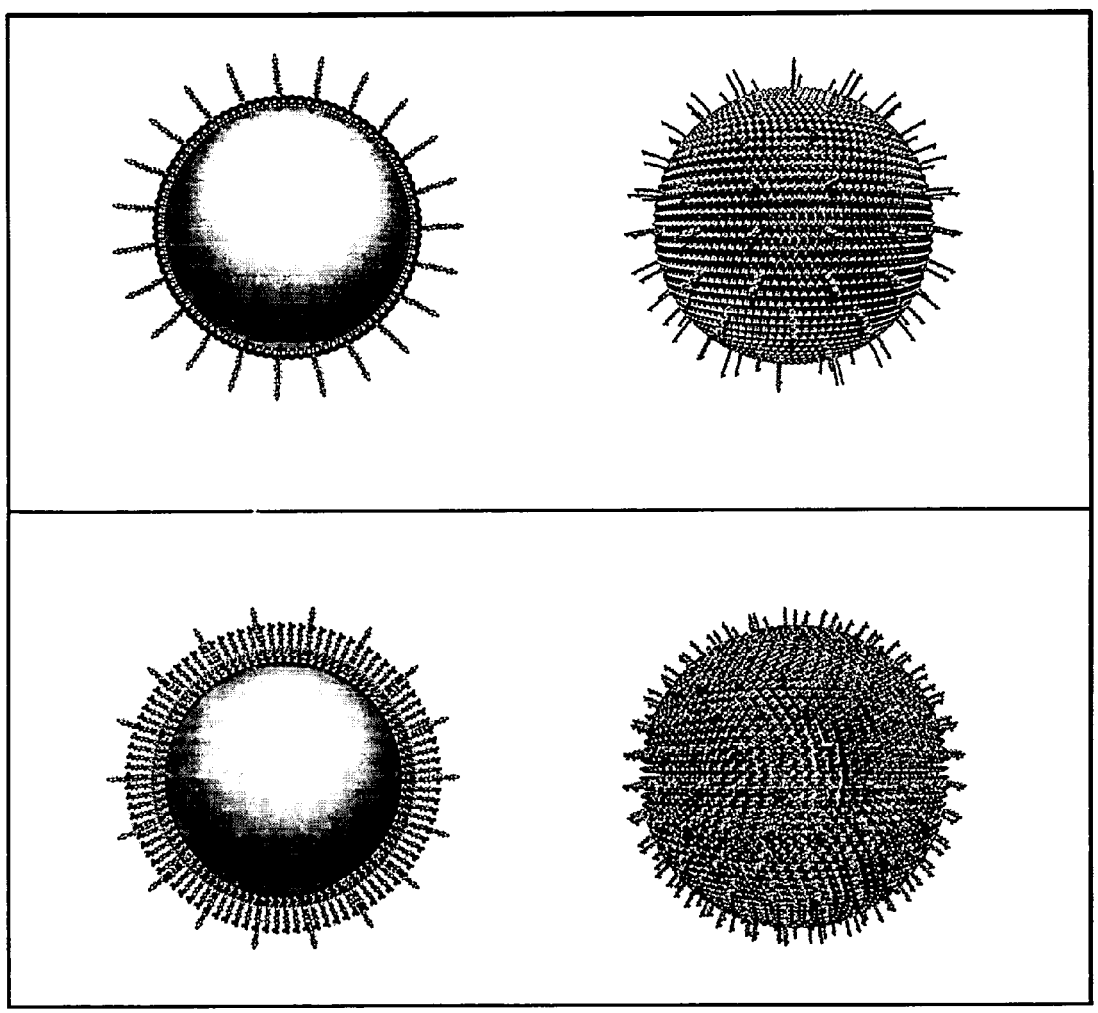

In one embodiment, the SERS marker comprises moieties comprising structure (Ia) and moieties comprising structure (IIa). Corresponding exemplary SERS markers are shown in FIG. 5 and Example 5. In a preferred embodiment, the SERS marker comprises moieties comprising structures (Ia) and (IIa), wherein structure (Ia) comprises a group Y and structure (IIa) does not comprise a group Y.

The spacer group (Sp) controls the spatial distance between the metal particle and a binding molecule for the selective target detection described herein below. One terminal end of Sp is bound to a group Y which allows coupling of the SERS marker to the binding molecule. In the absence of the spacer group, the dense packing of Raman-active reporter groups in the self-assembled monolayer on the metal particle can make the steric attack of binding molecules difficult. The advantage of a spacer group is that it introduces a spatial distance between the densely packed Raman-active reporter groups on the metal surface and the terminal group Y (see FIG. 5). As described above, a SERS marker may comprise a self-assembled monolayer consisting essentially of moieties that comprise spacer groups (i.e. moieties comprising structure (Ia)) and moieties that do not comprise spacer groups or comprise different (shorter) spacer groups (i.e. moieties comprising structure (IIa)), the moieties thus forming a so-called mixed self-assembled monolayer. The moieties comprising structure (Ia) are longer than the moieties comprising structure (IIa). Thus, the respective group Y of the moieties comprising structure (Ia) is sterically more easily accessible for binding molecules.

In a preferred embodiment, the moieties comprising structure (Ia) are distinguished from the moieties comprising structure (IIa) only in the nature of the spacer group (Sp vs. Sp*), i.e. all other structural features, including X, Ra and Y, are identical. However, it is also preferred, when at least the groups X and Ra in the moieties comprising structures (Ia) and (IIa) are identical.

Because of steric reasons, active surface groups in a densely packed "lawn" of a complete SAM composed of only one type of moiety are hardly accessible for active groups of (bio)molecules as shown in FIG. 3. FIG. 3 shows how the Raman marker molecules of the SAM are densely packed inside the uniform "lawn" of the SAM; because of this dense packing, (bio)conjugation is significantly (sterically) hampered or even impossible. This is considered to be the main and fundamental disadvantage of these markers. For example, following the approach and employing the methods of Porter (US 2005/0089901), it was not possible to reproduce the results described therein. In particular with regard to the conjugation to the antibody a sufficient result could not be obtained. In principle this could be circumnavigated by the formation of an incomplete SAM; this however would not only allow the SAM constituting molecules to assume a non-uniform geometry on the surface, but would also allow the direct adsorption of (bio)molecules to the gold surface; this also implies the danger of unspecific binding. Both effects lead to additional, undesired Raman bands in the SERS spectrum.

Spacer groups can differ in length. While Sp* can have a minimum length of 1 atom, or can even be absent (e.g. can be equal to a chemical bond), Sp has a minimum length of at least three atoms, in other words, Sp separates Ra and Y by at least three atoms. Thus, a minimal Sp can consist, for example, of the unit —O—$CH_2$—$CH_2$— or of an alpha amino acid moiety. Preferably, the atoms in the linear chain are carbon atoms. One or more of the carbon atoms can be replaced by S, N or O. For example, Sp* may comprise a linear chain of from 1 to about 500, preferably from about 3 to about 300, more preferably from about 5 to about 100 atoms, while Sp may preferably comprises a linear chain of from about 4 to about 503, more preferably from about 6 to about 303, even more preferably from about 8 to about 103 atoms. In particular, the linear chain of atoms in Sp which separates Ra and Y in the moiety of structure (Ia) is at least 3 atoms, preferably at least 5 atoms, more preferably at least 10 atoms and most preferably at least 20 atoms, longer than the linear chain of atoms in Sp* which separates Ra and Y, if present, in the moiety comprising structure (IIa). This also means that when Y is absent in structure (Ia), the linear chain of atoms in Sp which separates Ra and Y in the moiety of structure (Ia) is at least three atoms, preferably at least 5 atoms, more preferably at least 10 atoms and most preferably at least 20 atoms, longer than the longest linear chain of atoms in Sp*. While the length of the linear chain separating Ra and Y has been described, it is to be understood that the spacer groups can comprise branches in addition to this linear chain of atoms.

Sterical hindrance of binding molecules can be prevented or minimized by a different length of moieties comprising structures (Ia) and (IIa). For example, the moiety comprising structure (Ia) may be at least 0.1 nm, 0.2 nm, 0.5 nm, 1 nm, 5 nm or even at least 10 nm longer than the moiety comprising structure (IIa). The length of the spacer groups Sp and Sp* can, for example, be estimated by molecular models using tabulated values for the length of chemical bonds.

Additionally or alternatively, the sterical hindrance mentioned above may be minimized by choosing an appropriate molar ratio of moieties comprising structures (Ia) and (IIa) as discussed herein below. Preferably, the self-assembled monolayer comprises moieties comprising structure (Ia) and moieties comprising structure (IIa) in a molar ratio (Ia):(IIa) of from about 1:1 to about 1:10⁶, more preferably in a ratio of from about 1:1 to about 1:10⁵.

Optionally, the spacer groups may comprise monomer units which are arranged in linear chains and/or in branched, preferably linear, chains. Thus, Sp and Sp* can be an oligomer or a polymer comprising 2 to 100, preferably 3 to 50, more preferably up to 40, 30, 20 or 10, monomer units, wherein the monomer units are preferably selected from optionally protected natural or non-natural amino acids, saccharides, bivalent alcohols, and oxo carboxylic acids.

Non-limiting examples of amino acids are optionally protected natural amino acids (e.g. N-acetyl-lysine) and optionally protected non-natural amino acids (e.g. 11-aminoundecane carboxylic acid). When the spacer group is a peptide, it comprises preferably from 2 to 100, more preferably from 3 to 50, amino acid units. Preferably, free amino groups or thiol groups comprised in a monomer unit are protected, for example, by acetylation. Preferably, the peptide is water-soluble. In one preferred embodiment, peptides are employed which contain only one type of amino acid monomer, such as polyglycine, preferably having from 3 to 50 glycine units.

Non-limiting examples of saccharides are pentoses and hexoses, in particular aldopentoses (such as ribose and xylose) and aldohexoses (such as glucose, mannose and galactose) as well as ketopentoses (such as fructose). When the spacer group is an oligosaccharide, it comprises preferably from 2 to 100, more preferably from 3 to 50, saccharide units.

Non-limiting examples of bivalent alcohols include $C_{2-10}$ glycols, in particular ethylene and propylene glycol, most preferably ethylene glycol. When the spacer group is a polyether, it comprises preferably from 2 to 100, preferably from 3 to 50, monomer units.

Using oligo/poly(ethylene glycol) or oligo/poly(propylene glycol) as a spacer group may also reduce immunogenicity of the overall SERS marker which is advantageous especially for in vivo applications of said SERS markers.

Non-limiting examples of oxo carboxylic acids include $C_{2-6}$ ω-hydroxy carboxylic acids, such as β-hydroxy acetic acid and γ-hydroxy propionic acid. When the spacer group is a polyketide, it comprises preferably from 2 to 100, preferably from 3 to 50, monomer units.

In addition to oligomers and polymers, monomeric moieties can be employed as Sp and Sp*. For example, any of the above amino acids, saccharides, glycols and ω-hydroxy carboxylic acids can be used as Sp and Sp*. Further examples of Sp and Sp* include $C_{2-30}$, preferably $C_{2-20}$, more preferably $C_{2-10}$, aminoalcohols (such as 2-aminoethanol), $C_{2-30}$, preferably $C_{2-20}$, more preferably $C_{2-10}$, alkylene moieties having functional groups at the terminal ends such as amino, carboxylic acid and thio groups, and $C_{2-100}$, preferably $C_{2-20}$, more preferably $C_{2-10}$, polyalcohols (e.g. glycerol). While the minimal moiety comprised in Sp is a linear chain of 3 atoms, it is to be understood that Sp and Sp* can comprise longer linear or branched chains of atoms. Sp and Sp* can be covalently bound to the Raman-active reporter group Ra. An exemplary formation of the covalent bond is shown in Example 3. Functional groups of the spacer group, such as leaving groups or electrophilic groups, can be used for the conjugation to Ra. Non-limiting examples for such functional groups are hydroxyl groups, amino groups, vinyl groups, acrylic groups and halogens. For example, a spacer group may be covalently bound to Ra via an amino group. Before covalent binding a spacer group might have the following formula wherein one amino group is involved in covalent binding of the Raman-active reporter group and the second amino group is Y:

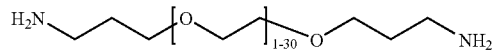

Preferably, Ra is coupled to the spacer group via an amide group, an ester group or a carbon-carbon bond.

In a preferred embodiment, the spacer groups are highly flexible, in particular highly conformationally flexible. For example, polyethylene glycol can be employed as spacer groups in this context. The use of flexible rather than rigid spacer groups can, for example, facilitate nucleophilic attack of binding molecules onto the groups Y of the SERS marker.

Further, spacer groups are preferably hydrophilic monomers, oligomers or polymers, such as (oligo/poly)peptides and (oligo/poly)saccharides as described above (see also Kumar (2005+2006), Ed., Nanotechnologies for the Life Sciences Book Series, Wiley). Such spacer groups may be highly water soluble and thus increase the water solubility of the whole SERS marker. This is advantageous if biological target molecules are to be detected since the use of organic solvents which often denaturate biological samples or biological molecules can be avoided.

In one embodiment of the present invention, the SERS marker comprises an encapsulant which surrounds the self-assembled monolayer.

For example, organic and inorganic polymers or biopolymers, typically hydrophilic ones, can be used as encapsulant. In one preferred embodiment, the encapsulant comprises silica $(SiO_2)_x$, thus yielding a three-dimensional silica network as shown in Examples 2 and 4.

Exemplary embodiments of a SERS marker comprising an encapsulant are shown in FIG. 6 as well as in Examples 2 and 4. The encapsulant can, for example, fulfil a protective function. It can increase the stability of the SAM and inhibit the aggregation of the metal (nano)particles as well as unspecific binding of individual SERS markers. Preferably, the shell has hydrophilic properties, thereby increasing the water solublity and/or swellablity and/or at least wettablity of the SERS marker. The shell can also link the functionalized metal (nano)particles to the surrounding medium, for example, an aqueous medium in the case of biological samples/targets. The encapsulant comprised in a SERS marker preferably confers a higher water solubility and/or higher storage stability, in particular at room temperature, to the SERS marker as compared to a SERS marker not comprising the encapsulant.

The storage stability can be determined by measuring the SERS signal intensities of the markers as a function of storage time at room temperature or at 4° C. Preferably, the signal decrease at 4° C. is less than 20% in a week, more preferably less than 10% and most preferably less than 5%. More preferably, the signal decrease at room temperature is less than 20% in a week, more preferably less than 10% and most preferably less than 5%. The water solubility can be expressed in relative terms by determining the maximum amount of the encapsulated marker which can be dissolved in water and the maximum amount of the non-encapsulated marker which can be dissolved in water (without particle aggregation). The ratio "encapsulated to non-encapsulated" then reflects the increase in water solubility due to encapsulation.

In one embodiment, an anchor group A which allows the encapsulant to adhere to the SAM, e.g. via a covalent bond, is covalently bound to the moiety comprising Ra. The encapsulant is covalently bound to A. In those embodiments wherein the encapsulant comprises silica, the anchor group A can be provided by an alkoxysilane containing compound. For example, a compound having a functional group at one terminal end and an alkoxysilane group at another terminal end can be coupled to the moiety comprising Ra via the functional group. The anchor group A can be part of the molecule comprising Ra as it is used for the formation of the SAM. Alternatively, moieties of the SAM may be post-functionalized after they have been adhered to the metal particles. Starting from the anchor group A, the encapsulant can then be grown. 3-Amino-n-propyltrimethoxysilane is an example of a suitable compound.

An examplary, simple silica-encapsulated SERS marker may comprise a metal nanoparticle, a self-assembled monolayer consisting essentially of moieties comprising a Raman-active reporter group Ra and a metal-binding group X, and an anchor group A attached to the moieties comprising a Raman-active reporter group Ra and a metal-binding group X, the anchor group A comprising a terminal trialkyloxysilane moiety. By the addition of TEOS (tetraethylorthosilicate) or other silicates in combination with a pH change, the SAM is covered by a cross-linked silica shell. Functional groups for the subsequent (bio)conjugation can be introduced via spacers having a terminal alkoxysilane moiety, such as a mono-, di- or trialkoxysilane moiety.

Alternatively, the encapsulant can be bound to the moiety comprising Ra without the use of an intermediary anchoring group. For example, a silica encapsulant can be directly grown on carboxylic acid groups which may be provided, e.g. when the SAM is obtained from para-thiol-benzoic acid.

In a preferred embodiment, the encapsulant comprises or consists of one or more, polymer layers, typically of one or more organic polymer(s) on the outer surface of the self-assembled monolayer. The encapsulant may consist solely of the one or more polymer layers, such as 2 or more, specifically 5 or more, and preferably 7 or even 10 or more. Alternatively, it may comprise one or more polymer layer(s) and one or more additional encapsulant layer(s) of different materials, such as, for example, a silica layer, further covering the outer surface of the polymer layer(s). Such a polymer encapsulant can, for example, be coupled to the outer surface of the SAM via assembled ultrathin films (see, for example, Quinn, Chem. Soc. Rev. (2007) 36, 707). The so-called layer-by-layer (LbL) deposition technique is a quite versatile method for surface modification in the present invention. Polyelectrolytes that can be used in this context include poly(diallyldimethylammonium chloride) (PDDA), poly(allylamine hydrochloride) (PAH), poly(styrenesulfonate) (PSS) and poly(acrylic acid) (PAA). In addition to electrostatic interactions, a number of additional driving forces for multilayer build-up can be exploited, such as hydrogen bonding. This is, for example, possible because many polymers incorporate moieties which can act as both hydrogen bonding donors and acceptors. Examples include polyaniline (PAni), poly(vinyl pyrrolidone) (PVPON or PVP), poly(vinyl alcohol) (PVA), poly(ethylen oxide) (PEO), polyacrylamide (PAAm), poly(4-vinyl pyridine) (P4VP), poly(methacrylic acid) (PMAA), poly(acrylic acid) (PAA), poly(4-vinyl phenol), and poly(styrene-alt-maleic acid).

Polyelectrolytes are especially well suited for surface modification in the context of the present invention (polyelectrolyte method, see for example Niemeyer, Nanobiotechnology, Wiley, 2004), in particular if the moiety comprising Ra provides a charge suitable for the adherence of a polyelectrolyte. Particle aggregation is or can be prevented by the inherent charge of the polymers, and overcompensation of this charge at each consecutive polyelectrolyte deposition, in addition to steric and electrosteric effects (Quinn, Chem. Soc. Rev. (2007) 36, 707; Podgornik, Current Opinion in Colloid and Interface Science (2006) 11, 273). Using an electrostatic interaction for surface modification is described in detail in appended Example 4. In this embodiment, one or more polymer layers are present on the outer surface of the self-assembled monolayer, and one or more additional encapsulant layers may be present on the outer surface of the outermost of the one or more polymer layers. For example, a first polymer layer carrying a charge opposite the charge of the moiety comprising Ra can be present on the outer surface of the self-assembled monolayer. A second polymer layer carrying a charge opposite the charge of the first polymer layer can then be present on the outer surface of the first polymer layer. The second polymer layer may be followed by further polymer layers of alternating charges. Finally, one or more additional encapsulant layers can be present on the outer surface of the outermost of the one or more polymer layers, in the case of overall two polymer layers on the outer surface of the second polymer layer.

Examples of charged groups which may be present in the Raman-active reporter groups Ra or in the moieties comprising the reporter groups include (optionally deprotonated) carboxylic acid groups and quarternary or protonated amino groups as well as suitable substituents from the list of substituents of Ra given above. Examples of polymers that can be present in the polymer layers include those indicated above in the context of LbL deposition. Examples of polymers that are particularly suitable for the outermost polymer layer include poly(vinylpyrrolidone) which is known to be vitreophilic (Chou, Microporous and mesoporous materials (2007) 98, 208), i.e. it provides a particular suitable basis for silica-encapsulation. The assembly of multi-layered particles has been described, for example, in Pastoriza-Santos, Chem Mater (2006) 18, 2465.

In one preferred embodiment, the encapsulant consists of 2 or more, such as 5 or more, specifically 7 or more and preferably 10 or more layers of polyelectrolytes of alternating charge that are present on the outer surface of the self-assembled monolayer.

In another, particularly preferred embodiment, the encapsulant comprises one or more, such as 2 or more, polyelectrolyte layers on the outer surface of the self-assembled monolayer and of an additional encapsulant layer comprising silica on the outer surface of the outermost of the one or more polyelectrolyte layers. The additional encapsulant layer comprising silica has a thickness of preferably less than 40 nm, more preferably less than 20 nm, even more preferably less than 10 nm and most preferably less than 5 nm. In this embodiment, it is particularly preferred that the polyelectrolyte layer which is applied last to the SERS marker comprises a polyelectrolyte which allows silica to stably adhere to the polyelectrolyte surface, such as poly(vinylpyrrolidone). In this case, the use of an additional primer layer or the use of coupling agents is not necessary. Siloxanes, such as tetraethylorthosilicate (TEOS) can be directly applied to such polymers to form a silica layer.

In those embodiments, wherein the encapsulant consists of one or more polyelectrolyte layers that are present on the outer surface of the self-assembled monolayer, the one or more polyelectrolyte layers may protect and stabilize the self-assembled monolayer and, in addition, may allow for thin encapsulation, resulting in a SERS marker of an overall small size. This is particularly preferable if the SERS marker is used for imaging applications.

The above mentioned advantages also apply to those embodiments, wherein the encapsulant comprises one or more polyelectrolyte layer(s) on the outer surface of the self-assembled monolayer and an additional encapsulant layer comprising silica on the outermost of the one or more polyelectrolyte layer(s). Furthermore, it has been surprisingly found that a silica shell of a higher quality can be obtained if the encapsulant comprises one or more polyelectrolyte layers on the outer surface of the self-assembled monolayer and an additional encapsulant layer comprising silica on the outermost of the one or more polyelectrolyte layers. The encapsulant layer comprising silica that is formed on the outermost of the one or more polyelectrolyte layers, will be much more uniform as compared to an encapsulant comprising silica that is formed on the outer surface of the self-assembled monolayer. Accordingly, the encapsulant layer comprising silica that is formed on the outermost of the one or more polyelectrolyte layers can be thinner than the encapsulant comprising silica that is formed on the outer surface of the self-assembled monolayer which is particularly preferable if an overall small SERS marker is desirable.

The minimal shell thickness of the encapsulant is on the order of a monolayer, i.e. about 0.1 nm to about 0.3 nm. Preferably, the encapsulant has a shell thickness of from about 0.1 nm to about 200 nm. More preferably, the encapsulant has a thickness of from about 0.2 nm to 100 nm, 0.3 nm to 50 nm or 0.4 nm to 40 nm. Most preferably, the encapsulant has a thickness of from about 1 nm to about 20 nm.

The SERS markers of those embodiments wherein the encapsulant comprises polymer layers may be conjugated to a binding molecule without the use of a spacer coupled to the encapsulant, as it is shown in Example 7 for a polyelectrolyte-coated SERS marker conjugated to bovine serum albumin (BSA).

Nevertheless, it is generally advantageous also for the SERS markers according to the invention, to contain a spacer group which binds the group Y to the surface of the encapsulant. This spacer group is referred to herein as $Sp^E$. The spacer group $Sp^E$, which can be present on the outer surface of the encapsulant, comprises a linear chain of at least three atoms separating the encapsulant and Y. Preferably, the linear chain of atoms separating the encapsulant and Y comprises from about 4 to about 503, more preferably from about 6 to about 303, even more preferably from about 8 to about 103 atoms, or up to about 80, 60, 40, 20 or 10 atoms. If the outermost encapsulant layer comprises silica, $Sp^E$ can be bound to the encapsulant by reaction of a alkoxysilane group (such as a mono-, di- or trialkoxysilane group) at one terminal end of the $Sp^E$ precursor. For example, 3-amino-n-propyltrimethoxysilane can be used as a $Sp^E$ precursor. If the outermost encapsulant layer is a polymer layer, $Sp^E$ can be can be bound to the encapsulant, for example, via an amide group, an ester group or a carbon-carbon bond. A person skilled in the art knows how to perform the respective coupling reactions.

As discussed herein above, sterical hindrance of binding molecules binding to the Y group can be prevented or minimized by using two types of spacer groups having different lengths, wherein the lengths of the two types of spacer groups can be adjusted, the percentage of spacer groups bound to a group Y can be adjusted, and the molar ratio of the two types of spacer groups having different lengths can be adjusted. These concepts are also applicable to the spacer group $Sp^E$ which can be present in the SERS marker comprising an encapsulant. Accordingly, any of the above described spacer groups Sp can also be employed as the spacer group $Sp^E$. An encapsulated SERS marker may comprise spacer groups $Sp^E$ and different, shorter spacer groups $Sp^{E*}$. Typically, the linear chain of atoms in $Sp^E$ is at least three atoms longer than the linear chain of atoms in $Sp^{E*}$. By adjusting the lengths of the spacer groups $Sp^E$ and $Sp^{E*}$ and, additionally or alternatively, the molar ratio of $Sp^E$ and $Sp^{E*}$, the respective group Y is sterically more easily accessible for binding molecules. The percentage of spacer groups bound to a group Y can also be adjusted, e.g., by varying the molar ratio of $Sp^E$ and $Sp^{E*}$, wherein the group Y can be absent in the moieties comprising $Sp^{E*}$.

$Sp^{E*}$ has a minimum length of one atom. $Sp^E$ has a minimum length of at least three atoms, in other words, $Sp^E$ separates the encapsulant and Y by at least three atoms. Thus, a minimal $Sp^E$ can consist, for example, of the unit —O—CH$_2$—CH$_2$— or of an alpha amino acid moiety. Preferably, the atoms in the linear chain are carbon atoms. One or more of the carbon atoms can be replaced by S, N or O. For example, $Sp^{E*}$ may comprise a linear chain of from 1 to about 500, preferably from about 3 to about 300, more preferably from about 5 to about 100 atoms, while $Sp^E$ preferably comprises a linear chain of from about 4 to about 503, more preferably from about 6 to about 303, even more preferably from about 8 to about 103 atoms, or up to about 80, 60, 40, 20 or 10 atoms. In particular, the linear chain of atoms in $Sp^E$ which separates the encapsulant and Y is at least 3 atoms, preferably at least 5 atoms, more preferably at least 10 atoms and most preferably at least 20 atoms, longer than the linear chain of atoms in $Sp^{E*}$ which separates the encapsulant and Y, if present. This also means that when Y is absent in the moiety comprising $Sp^{E*}$, the linear chain of atoms in $Sp^E$ which separates the encapsulant and Y is at least three atoms, preferably at least 5 atoms, more preferably at least 10 atoms and most preferably at least 20 atoms, longer than the longest linear chain of atoms in $Sp^{E*}$. While the length of the linear chain separating the encapsulant and Y has been described, it is to be understood that the spacer groups can comprise branches in addition to this linear chain of atoms.

Optionally, the spacer groups may comprise monomer units which are arranged in linear chains and/or in branched, preferably linear, chains. Thus, $Sp^E$ and $Sp^{E*}$ can be an oligomer or a polymer comprising 2 to 100, preferably 3 to 50, more preferably up to 40, 30, 20 or 10, monomer units, wherein the monomer units are preferably selected from optionally protected natural or non-natural amino acids, saccharides, bivalent alcohols, and oxo carboxylic acids.

Non-limiting examples of amino acids are optionally protected natural amino acids (e.g. N-acetyl-lysine) and optionally protected non-natural amino acids (e.g. 11-aminoundecane carboxylic acid). When the spacer group is a peptide, it comprises preferably from 2 to 100, more preferably from 3 to 50, amino acid units. Preferably, free amino groups or thiol groups comprised in a monomer unit are protected, for example, by acetylation. Preferably, the peptide is water-soluble. In one preferred embodiment, peptides are employed which contain only one type of amino acid monomer, such as polyglycine, preferably having from 3 to 50 glycine units.

Non-limiting examples of saccharides are pentoses and hexoses, in particular aldopentoses (such as ribose and xylose) and aldohexoses (such as glucose, mannose and galactose) as well as ketopentoses (such as fructose). When the spacer group is an oligosaccharide, it comprises preferably from 2 to 100, more preferably from 3 to 50, saccharide units.

Non-limiting examples of bivalent alcohols include $C_{2-10}$ glycols, in particular ethylene and propylene glycol, most preferably ethylene glycol. When the spacer group is a polyether, it comprises preferably from 2 to 100, preferably from 3 to 50, monomer units.

Using oligo/poly(ethylene glycol) or oligo/poly(propylene glycol) as a spacer group may also reduce immunogenicity of the overall SERS marker which is advantageous especially for in vivo applications of said SERS markers.

Non-limiting examples of oxo carboxylic acids include $C_{2-6}$ co-hydroxy carboxylic acids, such as β-hydroxy acetic acid and γ-hydroxy propionic acid. When the spacer group is a polyketide, it comprises preferably from 2 to 100, preferably from 3 to 50, monomer units.

In addition to oligomers and polymers, monomeric moieties can be employed as $Sp^E$ and $Sp^{E*}$. For example, any of the above amino acids, saccharides, glycols and co-hydroxy carboxylic acids can be used as $Sp^E$ and $Sp^{E*}$. Further examples of $Sp^E$ and $Sp^{E*}$ include $C_{2-30}$, preferably $C_{2-20}$, more preferably $C_{2-10}$, aminoalcohols (such as 2-aminoethanol), $C_{2-30}$, preferably $C_{2-20}$, more preferably $C_{2-10}$, alkylene moieties having functional groups at the terminal ends such as amino, carboxylic acid and thio groups, and $C_{2-100}$, preferably $C_{2-20}$, more preferably $C_{2-10}$, polyalcohols (e.g. glycerol). While the minimal moiety comprised in $Sp^E$ is a linear chain of 3 atoms, it is to be understood that $Sp^E$ and $Sp^{E*}$ can comprise longer linear or branched chains of atoms.

In a preferred embodiment, the spacer groups are highly flexible, in particular highly conformationally flexible. For example, polyethylene glycol can be employed as spacer groups in this context. The use of flexible rather than rigid spacer groups can, for example, facilitate nucleophilic attack of binding molecules onto the groups Y of the SERS marker.

Further, spacer groups are preferably hydrophilic monomers, oligomers or polymers, such as (oligo/poly)peptides and (oligo/poly)saccharides as described above (see also Kumar (2005+2006), Ed., Nanotechnologies for the Life Sciences Book Series, Wiley). Such spacer groups may be highly water soluble and thus increase the water solubility of the whole SERS marker. This is advantageous if biological target molecules are to be detected since the use of organic solvents which often denaturate biological samples or biological molecules can be avoided.

In all embodiments according to the invention, Y is a group which allows coupling of the SERS marker to a binding molecule. Y can, for example, be a carboxylic acid group, an amino group, an aldehyde, a hydroxyl group or a thiol group. Alternatively, Y can be an activated derivative of any of the these groups, such as esters, carbodiimides, N-hydroxysuccinimide (NHS), sulfo-NHS, haloacetyl, pyridyl disulfide, hydrazide, imidoester, isocyanate, aryl azides (in particular phenyl azide), benzophenone, glyoxal, maleimide and vinylsulfones. For example, Y can be a carboxylic acid group which has been activated by NHS or sulfo-NHS; for details on bioconjugation techniques see Hermanson, Bioconjugate Techniques, Academic Press, 1996. The activation can be carried out in situ, i.e. simultaneously with the coupling to the binding molecule, or in a separate preceding step.

Y can be a group bound to one terminal end of a spacer group. In those embodiments wherein the outermost encapsulant layer is a polymer layer, Y can also be provided by the functional groups of the polymer, preferably an organic polymer, comprised in the encapsulant layer.

It is preferred that the Y group is accessible for a binding molecule employed herein, i.e. no or only minimal sterical hindrance for the binding of a binding molecule preferably occurs. As discussed herein above, sterical hindrance of binding molecules binding to the group Y of the SERS marker may be prevented or minimized by adjusting the lengths of the spacer groups, the relative amounts of spacer groups present, and the molar ratio of spacer groups having different lengths. The prevention or minimization of sterical hindrance of binding molecules is particularly advantageous with respect to the loading capacity of the SERS marker regarding binding molecules, e.g. antibodies. By a preferably very low or absent sterical hindrance said loading capacity can be controlled and is accordingly not as arbitrary as in the SERS markers described in the prior art. Thus, a person skilled in the art may be able to load a defined number of binding molecules to the SERS marker.

A binding molecule can be bound to Y as illustrated in appended Examples 4 and 5. Said binding molecules may, for example, be used in order to determine the uptake of target molecules bound to said binding molecules into a cell and their fate inside the cell as well as their degradation or release in or out of cell. Suitable methods for binding a binding molecule to Y are well known to the person skilled in the art. Binding can in particular be facilitated by any of the abovementioned activated derivatives of Y. For details on bioconjugation techniques see Hermanson, Bioconjugate Techniques, Academic Press, 1996.

Based on prior art literature, the person skilled in the art is familiar with obtaining specific binding molecules that may be useful in the context of the present invention. These molecules are directed and bind specifically to or specifically label the target molecules described below. Exemplary binding pairs comprising (a) binding molecule(s) and (a) target molecule(s) may be antigen and antibody-specific binding pairs, biotin and avidin binding pairs, carbohydrate and lectin binding pairs, complementary nucleotide sequences, complementary peptide sequences, effector and receptor molecules, enzyme cofactor and enzymes, and enzyme inhibitors and enzymes. Non-limiting examples of suitable binding molecules may be selected from nucleic acids, DNA, RNA, PNA, oligonucleotides, aptamers (Gold, Ann. Rev. Biochem. 64 (1995), 763-797)), aptazymes, RNAzymes, ribozymes (see e.g., EP-B1 0 291 533, EP-A1 0 321 201, EP-B1 0 360 257), antisense DNA, antisense oligonucleotides, antisense RNA, siRNA, RNAi, shRNA, amino acids, peptides, peptides comprising a tumor specific epitope, polypeptides, proteins, glycoproteins, lipoproteins, nucleoproteins, albumins, hemoglobin, coagulation factors, antibodies (Harlow and Lane "Antibodies, A Laboratory Manual", CSH Press, Cold Spring Harbor, 1988), monocloncal antibodies, polyclonal antibodies, immunoglobulins, affibodies (Hansson, Immunotechnology 4 (1999), 237-252; Henning, Hum Gene Ther. 13 (2000), 1427-1439), immunoreactive fragments, immunoreactive derivatives, antigens, epitopes, haptens, cell-surface molecules, receptors, cofactors, ligands, small organic molecules, lectins or derivatives thereof, lectin fragments, trinectins (Phylos Inc., Lexington, Mass., USA; Xu, Chem. Biol. 9 (2002), 933), anticalins (EPB1 1 017 814), hormones, peptide and protein hormones, non-peptide hormones, steroids, interleukins, interferons, cytokines, neurotransmitters, toxins, enzymes, polysaccharides, carbohydrates, lipids, lipopolysaccharides, vitamins, crown ethers, cyclodextrins, cryptands, calixarenes, aldehydes, thiols, amines, drugs, drugs of abuse, therapeutic agents, medicaments, pharmaceuticals, explosives, environmental pollutants, substrates, fragments, portions, components or products of microorganisms, metabolites of or antibodies to any of the above substances and the like.

The term "specifically binding" is meant to refer to the high affinity antibodies or other binding molecules known in the prior art typically have for the target molecule against which they were prepared. Advantageously, the term "specifically binding" refers to a specificity of the binding molecule that allows a distinction between the below described target molecules and molecules not targeted by the binding molecule(s) in the sense that the binding molecule does not show a significant cross-reactivity with the latter molecules. The person skilled in the art is able to prepare such distinctive binding molecules.

Binding molecules can, inter alia, be used for detecting the presence, absence or amount of the target molecule described below in a biological sample. The binding molecules may furthermore be used for isolating the target molecules from a biological source material. Said binding molecules may also be used in order to determine the uptake of target molecules bound to said binding molecules into a cell and their fate inside the cell as well as their degradation or release in or out of the cell.

The binding molecule may be a "nucleotide sequence". The term "nucleotide sequence" is well known in the art. For example, "nucleotide sequence" as used herein refers to all forms of naturally occurring or recombinantly generated types of nucleic acids and/or nucleotide sequences as well as to chemically synthesized nucleic acids/nucleotide sequences. This term also encompasses nucleic acid analogs and nucleic acid derivatives such as locked DNA, PNA, oligonucleotide thiophosphates and substituted ribo-oligonucleotides. Furthermore, the term "nucleotide sequence" also refers to any molecule that comprises nucleotides or nucleotide analogs.

Preferably, the term "nucleotide sequence" refers to deoxyribonucleic acid (DNA) and ribonucleic acid (RNA). The "nucleotide sequence" in the context of the present invention may be made by synthetic chemical methodology known to one of ordinary skill in the art, or by the use of recombinant technology, or may be isolated from natural sources, or by a combination thereof. The DNA and RNA may optionally comprise unnatural nucleotides and may be single or double stranded. "Nucleotide sequence" also refers to sense and antisense DNA and RNA, that is, a nucleotide sequence which is complementary to a specific sequence of nucleotides in DNA and/or RNA.

In the context of the present invention, a nucleotide sequence that "corresponds" to another nucleotide sequence is a nucleotide sequence (basically) representing the same length and sequence information as the other nucleotide sequence, but, for example, using different kind of nucleotides, like, e.g., U (uridine) instead of T (thymidine). Particularly, this refers to an RNA (e.g. a mRNA or hnRNA) that "corresponds" to a DNA (e.g. gDNA or cDNA) representing the same sequence information or, vice versa, to a DNA that "corresponds" to an RNA representing the same sequence information.

Non-limiting examples of nucleotide sequences are genes, viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids.

As mentioned above, one particular binding molecule in the context of the present invention is envisaged to be an antisense nucleotide sequence, i.e. a nucleotide sequence complementary to those target molecules defined herein being nucleotide sequences. Preferably, the antisense nucleotide sequence is an antisense RNA sequence. In a particular embodiment, the antisense nucleotide sequence comprises or is an antisense nucleotide sequence corresponding to a specific nucleotide sequence.

The antisense nucleotide sequences may have a length of at least 15, preferably of more than 50, more preferably of more than 100, even more preferably of more than 200 and most preferably of more than 500 nucleotides. However, antisense nucleotide sequences that usually are employed in the art are shorter than 5000 nucleotides or even shorter than 2500 nucleotides, and so the antisense nucleotide sequences as provided herein are intended to be.

In accordance with the present invention, the term "aptamer" means nucleic acid molecules that can specifically bind to target molecules. Aptamers commonly comprise RNA, single stranded DNA, modified RNA or modified DNA molecules. The preparation of aptamers is well known in the art and may involve, inter alia, the use of combinatorial RNA libraries to identify binding sites (Gold (1995), Ann. Rev. Biochem 64, 763-797).

The meaning of the terms "proteins", "peptides", "antibodies", "epitopes" and "haptenes" is well known in the art, and are, if not otherwise defined herein, used accordingly in the context of the present invention.

As mentioned above, one particular binding molecule in the context of the present invention is an antibody specific for/specifically binding the target molecules as defined herein, for example mRNA of a specific gene, or a variant or a fragment thereof, or a protein or truncated variant encoded by a specific nucleic sequence. The antibody can be, for example, polyclonal or monoclonal. The term "antibody" also comprises derivatives or fragments thereof which still retain the binding specificity.

In the context of the present invention, the term "antibody" relates to full immunoglobulin molecules as well as to parts of such immunoglobulin molecules substantially retaining binding specificity. Furthermore, the term relates to modified and/or altered antibody molecules, like chimeric and humanized antibodies. The term also relates to recombinantly or synthetically generated/synthesized antibodies. The term also relates to intact antibodies as well as to antibody fragments thereof, such as separated light and heavy chains, Fab, Fab/c, Fv, Fab', F(ab')$_2$. The term "antibody" also comprises bifunctional antibodies, trifunctional antibodies and antibody constructs, such as single chain Fvs (scFv) or antibody-fusion proteins.

Techniques for the production of antibodies are well known in the art and described, e.g. in Harlow and Lane "Antibodies, A Laboratory Manual", CSH Press, Cold Spring Harbor, 1988. Antibodies directed against a polypeptide can be obtained, e.g., by direct injection of the target molecule into an animal or by administering the target molecule to an animal, preferably a non-human animal. The antibody so obtained will then bind the target molecule itself. In this manner, even a fragment of the target molecule can be used to generate antibodies binding the whole target molecule, as long as said binding is "specific" as defined above.

Particularly preferred in the context of the present invention are monoclonal antibodies. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Various procedures are known in the art and may be used for the production of such antibodies and/or fragments. Thus, the antibody derivatives can also be produced by peptidomimetics. Further, techniques described for the production of single chain antibodies (see, inter alia, U.S. Pat. No. 4,946,778) can be adapted to produce single chain antibodies specifically recognizing the polypeptide of the invention. Also, transgenic animals may be used to express humanized antibodies to a polypeptide.

An epitope employed herein is a part of an antigen that combines with the antigen-binding site on an antibody molecule or on a lymphcyte receptor. In contrast thereto a hapten is a small organic molecule of simple structure (e.g. arsonate and nitrophenyl) which does not provoke antibodies by themselves. However, if a hapten is attached to an appropriate carrier it may become immunogenic even if the carrier also does not elicit an immune response by itself. Appropriate carriers are well known in the art.

Another particular binding molecule is a ribozyme, particularly such a ribozyme that specifically recognizes and cleaves a specific target nucleotide sequence. The ribozyme technology is also well known in the art. Generally, ribozymes are known to be catalytically active RNA molecules capable of cleaving RNA molecules and specific target sequences. By means of recombinant DNA techniques it is possible to alter the specificity of ribozymes. There are various classes of ribozymes. For practical applications aiming at the specific cleavage of the transcript of a certain gene, use is preferably made of representatives of two different groups of ribozymes. The first group is made up of ribozymes which belong to the group I intron ribozyme type. The second group consists of ribozymes which, as a characteristic structural feature, exhibit the so-called "hammerhead" motif. The specific recognition of the target RNA molecule may be modified by altering the sequences flanking this motif. By base pairing with sequences in the target molecule these sequences determine the position at which the catalytic reaction and therefore the cleavage of the target molecule takes place. Since the sequence requirements for an efficient cleavage are low, it is in principle possible to develop specific ribozymes for practically each desired RNA molecule.

The meaning of the term "hormone" is well known in the art and may be deduced, for example, from Pschyrembel (1994, Walter de Gruyter, $257^{th}$ edition). Hormones can be classified in steroid hormones (e.g. estrogen, gestagen, androgen, glucocorticoid, mineralocorticoid, colecalciferol and derivatives thereof), polypeptide hormones or proteohormones, respectively (e.g. releasing hormones, oxytocin, vasopressin, insulin, glucagon, parathormone, calcitonin), hormones derived from amino acids (e.g. catecholamine, acetylcholine) and hormones derived from unsaturated fatty acids (e.g. prostaglandine). Hormones may also be classified according to the tissue/organ which produces said hormones. For example, gastro-intestinal hormones are, produced by the gastrointestinal tract and include but are not limited to gastrin, cholecystokinin, secretin, motilin, enteroglucagon, serotonin and the like. Similarly, renal hormones are produced by the kidney. Non-limiting examples of renal hormones are erythropoetin, renin, prostaglandine, vitamin D3 and kinine.

The meaning of the term "carbohydrates" is also well known in the art and may be deduced, for example, from Stryer "Biochemie" (1996, Spektrum Akademischer Verlag, $4^{th}$ edition). Carbohydrates comprise at least one monosaccharide unit (e.g. glucose, galactose, fructose). The coupling of two monosaccharide units leads to the generation of disccharides (e.g. sucrose, lactose and the like), whereas carbohydrates comprising 3 to 6 monosaccharide units are defined as oligosaccharides. Carbohydrates comprising more than 6 monosaccharide units are known as polysaccharides. Non-limiting examples of polysaccharides are glycogen in animals or starch and cellulose in plants. Carbohydrates may also be linked to proteins (called glycoproteins) or lipids (called glycolipids).

The meaning of the term "medicament" is well known in the art and may be deduced, for example, from Pschyrembel (1994, Walter de Gruyter, $257^{th}$ edition). A person skilled in the art is aware of the fact that a medicament can comprise "drug substances" as active agents and excipients. The term "drug substance" as used herein refers in particular to compounds/substances of natural (e.g. biogenic origin, plant origin, animal origin or bacterial origin), semi-synthetic (e.g. genetically engineered) and synthetic origin used in diagnosis, prophylaxis and therapy in human and veterinary medicine. The term "drug substance" means in the context of the present invention a pharmaceutically active agent which exerts a desirable or undesirable effect on the functions of living material such as cells, cell suspensions, tissues, organs, organisms and the like in a differentiated manner.

Non-limiting examples of drug substances are: analgesics, anti-inflammatory agents, anthelmintics, antibacterial agents, antidepressants, antidiabetic agents, antiepileptics, antifungal agents, antigout agents, antihistamines, antimigraine agents, antimuscarinic agents, antineoplastic agents, immunosuppressants, antiprotozoal agents, antiviral agents, anxiolytic sedatives hypnotics, antipsychotics, blood products plasma expanders, haemostatics, calcium regulating agents, cardiovascular agents, cough suppressants expectorants, mucolytics, dermatological agents, diagnostic agents, dopaminergic agents, gastro-intestinal agents, anaesthetics, lipid regulating agents, nutritional agents, vitamins, pesticides, prophylactic anti-asthma agents, radiopharmaceuticals, skeletal muscle relaxants, stimulants and thyroid agents. Further examples of drug substances may be found, for example, in Martindale (1996, Royal Pharmaceutical Society of Great Britain, $31^{st}$ edition).

The overall size of the SERS marker (in the case of spherical SERS markers: diameter; otherwise: length) is preferably in the Tange of from about 1 nm to about 800 nm, more preferably from about 10 nm to about 400 nm and most preferably from about 20 nm to about 200 nm. The size of the SERS marker does preferably not exceed 800 nm, since this can restrict its use, such as in Raman imaging experiments, in particular with regard to spatial resolution. Preferably, the marker dimensions are smaller than the diffraction limited resolution of the light microscope. Further, the upper size limits given above can keep the overall weight/mass of the SERS particle low. This can be preferred in order to facilitate selective and stable binding of the SERS marker, for example in tissue diagnostic applications. Ideally, the SERS marker does not affect the binding efficiency to the target molecule, for example, between a target protein and its corresponding antibody. Small SERS markers have the additional advantage that, e.g. for microscopy applications, many different SERS markers can be localized in a given laser spot diameter, which is desired for multiplexing. On the other hand, when the particle size is below the lower limits given above the ratio of Mie absorption to scattering may become unfavourable. In particular, for single particles, for example with a size of smaller than 20 nm, scattering can be small as compared to absorption (see for example Aroca, Surface-enhanced Vibrational Spectroscopy, Wiley, 2006; Bohren, Absorption and Scattering of Light by Small Particles, Wiley, 2004).

Further, it is preferred when the SERS marker is water soluble. SERS markers should also exhibit a sufficient stability in solvents, in particular water. At the same time the SERS marker should also be relatively inert against air oxygen and show a high storage stability. For example, after storage for at least one year preferably less than 10% of the SERS marker given in a specific solvent, such as water, is dissociated or has lost its function. More preferably, less than 5%, 2% or 1% of the SERS marker is dissociated after storage for at least one year. The storage stability can, for example, be determined as described above.

In a preferred embodiment, the SERS markers have the potential for a large multiplexing capacity. Accordingly, the spectral density of normal modes should not be too high in order to avoid or minimize a spectral overlap of the Raman scattering contributions enhanced by the local field. Spectrally overlapping signals result in a decreased multiplexing capacity. The differential cross section and the polarizability, respectively, of the corresponding Raman bands should be high. For this reason, substances with conjugated π electrons such as aromatic compounds, polyenes, or polyynes are well suited as Raman-active reporter groups Ra. Increasing the number of different Raman-active reporter groups for multiplexing can be achieved by various means, for example, by varying the chemical lead structure ("Leitstruktur"; for example, benzene vs. naphthalene etc.), by varying the chain/conjugation length, by varying the substitution pattern (e.g. type of substituent, the number of substituents and their position), and by isotopic labelling (e.g. using single or multiple isotope substitutions, for example, with $^{13}C$ and/or other isotopes). See, for example, Hesse/Meier/Zeh, Spektroskopische Methoden in der organischen Chemie, Thieme, 1991).

Further, the SERS marker disclosed herein may comprise moieties comprising two or more different types of Raman-active reporter groups Ra within the SAM. This embodiment can be useful for multiplexing applications wherein a large number of diverse SERS markers are required. For example, a set of SERS markers can be simultaneously employed, wherein each SERS marker is distinguished from the other SERS markers not only by its specific binding molecule, but also by the ratio of the different Raman-active reporter groups within the SAM. This approach provides a very large number of different ("encoded") SERS markers; the multiplexing capacity has been estimated to be on the order of millions (Su, Nanoletters (2005) 5, 49). This type of multiplexing has also been described in the context of quantum dots (Rosi, Chemical Reviews (2005) 105, 1547; Tansil, NanoToday (2006) 1, 28).

The present invention relates in a further aspect to a compound comprising the linear structure (I)

X'~Ra~Sp~Y      (I)

wherein
X' is a group which allows coupling of the compound comprising structure (I) to a metal particle;
Ra is a Raman-active reporter group, wherein X' can be comprised in Ra;
Sp is a spacer group comprising a linear chain of at least three atoms separating Ra and Y, and
Y is a group which allows coupling of the compound comprising structure (I) to a binding molecule.

Ra, Sp and Y are as defined above. Details and preferred embodiments of the present compound correspond to the details and preferred embodiments described hereinabove in the context of the present SERS markers.

The present invention relates in a further aspect to a first method for the preparation of the SERS marker described herein above, the method comprising the steps of:
(i) providing a suspension of metal particles;
(ii) providing a solution comprising compounds comprising the linear structure (I)

X'~Ra~Sp~Y      (I)

wherein
X' is a group which allows coupling of the compound comprising structure (I) to a metal particle,
Ra is a Raman-active reporter group, wherein X' can be comprised in Ra,
Sp is a spacer group comprising a linear chain of at least three atoms separating Ra and Y, and Y is a group which allows coupling of the compound compounds comprising the linear structure (II)

X'~Ra~Sp*~Y      (II)

wherein
X' is a group which allows coupling of the compound comprising structure (II) to a metal particle,
Ra is a Raman-active reporter group, wherein X' can be comprised in Ra,
Sp* is a spacer group, wherein Sp* is optionally absent, and
Y is a group which allows coupling of the moiety comprising structure (IIa) to a binding molecule and wherein Y is optionally absent,
provided that the linear chain of atoms in Sp which separates Ra and Y in the compound comprising structure (I) is at least three atoms longer than the linear chain of atoms in Sp* which separates Ra and Y in the compound comprising structure (II)
(iii) adding the solution obtained in step (ii) to the suspension obtained in step (i), to provide the self-assembled monolayer on the metal particles.

This method is illustrated in example 5.

Further, the present invention relates to a second method for the preparation of the SERS marker described herein above, the method comprising the step of:
(i) providing a suspension of metal particles;
(ii) providing a solution of compounds comprising the linear structure (III)

X'~Ra      (III)

wherein
X' is a group which allows coupling of the compound comprising structure (III) to a metal particle, and
Ra is a Raman-active reporter group, wherein X' can be comprised in Ra;
(iii) adding the solution obtained in step (ii) to the suspension obtained in step (i), to provide the self-assembled monolayer on the metal particle;
(iv) forming an encapsulant, whereby the encapsulant is covalently bound to a compound comprising the linear structure (III); and
(v) providing a group Y which allows coupling of the SERS marker to a binding molecule.

This method is illustrated in example 2.

In a preferred embodiment of the second method, in the compound comprising the linear structure (III) an anchor group A is present (i.e. X'~Ra~A) and the encapsulant binds to the anchor group.

Further, the present invention relates to a third method for the preparation of the SERS marker described herein above, the method comprising the steps of:
(i) providing a suspension of metal particles;
(ii) providing a solution of compounds comprising the linear structure (III)

X'~Ra      (III)

wherein
X' is a group which allows coupling of the compound comprising structure (III) to a metal particle, and
Ra is a Raman-active reporter group, wherein X' can be comprised in Ra;
(iii) adding the solution obtained in step (ii) to the suspension obtained in step (i), to provide a self-assembled monolayer on the metal particle;

(iv) adding a solution of a polymer to the suspension obtained in step (iii), whereby a polymer layer is formed on the outer surface of the particle obtained in the previous step;
(v) optionally repeating step (iv) one or more (for example two, three, four or five) times; and
(vi) providing a group Y which allows coupling of the SERS marker to a binding molecule.

This method is illustrated in example 4.

The same conditions can be employed in the first three steps ((i) to (iii)) of the first through third method mentioned above.

In step (i), the nanoparticles can be suspended in water, organic solvents, and solvent mixtures. Preferable solvents are water, dimethylsulfoxide, dimethylformamide, ethanol, methanol, isopropanole, ethylene glycole, tetrahydrofuran, dichloromethane, chloroform and acetonitrile. Where appropriate, additional components (e.g. buffer salts, detergents, polymers) for improving solubility and/or stability can be used.

In step (ii), compounds (I) to (III) can be dissolved or suspended in water, organic solvents, and solvent mixtures. Preferable solvents are water, dimethylsulfoxide, dimethylformamide, ethanol, methanol, isopropanole, ethylene glycole, tetrahydrofuran, dichloromethane, chloroform, and acetonitrile. Where appropriate, additional components (e.g. buffer salts, detergents, polymers) for improving solubility and/or stability can be used. In case of reactive compounds (e.g. compounds susceptible to hydrolysis), a protective atmosphere (e.g. under nitrogen or argon gas) should be employed. The solutions or suspensions are typically prepared by stirring at room temperature and atmosphere pressure. Various procedures for increasing the solubility of compounds (I) to (III) in the corresponding solvent can be applied, for example, heating, ultra sonification, and vortexing.

In step (iii), the solutions/suspensions obtained in steps (i) and (ii), respectively, are mixed at a temperature ranging from about −20° C. to 160° C., preferably from about 10° C. to 80° C., and most preferably from about 15° C. to 50° C. Various procedures for mixing exist, such as addition by magnetic stirring (typically between 100 rpm to 5000 rpm), shaking or drop-by-drop addition. In case of reactive compounds (e.g. compounds susceptible to hydrolysis), a protective atmosphere (e.g. under nitrogen or argon gas) should be employed. The incubation time for the formation of the self-assembled monolayer (SAM) on the metal surface may vary from about 1 second to 7 days, preferably from about 30 seconds to 24 h. Purification of the surface-functionalized nanoparticles can be achieved by (repeated) centrifugation with subsequent resuspension in water, organic solvents, or solvent mixtures. Preferable solvents are water, dimethylsulfoxide, dimethylformamide, ethanol, methanol, isopropanole, ethylene glycole, tetrahydrofuran, dichloromethane, chloroform and acetonitrile. Where appropriate, additional components (e.g. buffer salts, detergents, polymers) for improving solubility and/or stability can be used.

In a preferred embodiment, the third method comprises a further step of forming an additional encapsulant layer, preferably a layer comprising silica, on the outer surface of the outermost polymer layer.

In an exemplary procedure for the formation of the encapsulant or an additional encapsulant layer, respectively (step (iv) of the second method, or the above mentioned further step of the third method), a compound capable of forming a silica shell in aqueous or organic solvents under conditions similar to Stöber synthesis can be added, whereby a silica shell can be grown on top of the SAM or on the outer surface of the outermost polymer layer, respectively (see Stöber (1968) Colloid Interface Sci 26, 62). The resulting particles can be centrifuged, if necessary several times, and resuspended in an aqueous or organic solvent or in a mixture of an organic solvent and water.

In a preferred embodiment, the second method and the third method comprise a further step of bonding one terminal end of a spacer group $Sp^E$ comprising a linear chain of at least three atoms to the outer surface of the encapsulant, wherein the other terminal end of $Sp^E$ is bound to the group Y.

The above first through third methods may further comprise the step of binding a binding molecule to group Y. This reaction can be achieved by standard methods, such as activation of COOH groups with NHS (for details on bioconjugation techniques see Hermanson, Bioconjugate Techniques, Academic Press, 1996). For example a binding molecule can be bound to the SERS marker as described in US 2005/0089901 or as described in examples 4 and 5 of US 2006/0054506.

In preferred embodiments of the above first through third methods, the respective step (iii) comprises adding an excess of the compounds comprising the Raman-active reporter group to the suspension obtained in the respective step (i).

In the above mentioned preferred embodiments, an "excess" of the compounds comprising a Raman-active reporter group is present if the ratio $x=(n_{Ra\ added})/(n_{Ra/particle} \cdot n_{particle})$ is a number between 1.1 and 1 000 000, preferably between 10 and 100 000, and more preferably between 100 and 10 000, with $n_{Ra\ added}$ being the number of molecules comprising Ra that was added, $n_{Ra/particle}$ being the quotient of the surface area of the metal particle and the required space of one compound comprising Ra within the self-assembled monolayer, and $n_{particle}$ being the number of metal particles that was added. Typically, the number of compounds constituting a SAM on a 50 nm nanoparticle is in the range of 15 000 to 67 000 (or up to 68 000). The required space of one compound comprising Ra within the self-assembled monolayer can be determined, for example, by forming a SAM of that specific compound comprising Ra on a flat metal surface and analyzing this sample by surface-selective methods, such as scanning tunneling microscopy (STM) or atomic force microscopy (AFM). With high-resolution STM/AFM experiments the intermolecular spacing between the compounds in the SAM can be visualized, whereby the required space of this specific compound in a SAM can be determined. However, as a rule of thumb, it can be assumed that the space required for a single compound in the SAM is in the range of from about 0.215 $nm^2$ for an alkanethiol (see Mitzutani, Motomatsu, Tokumoto (1996) Thin Solid Films, 273, 70) to about 0.5 $nm^2$ for anthracene-based aromatic thiols with rigid, large π-systems (Dou, Ma, Xi, Yip, Wong, Lau, Jia, Xue, Yang, Ma, Jen (2006) Langmuir, 22, 3049).

In a preferred embodiment of the present invention, a polyelectrolyte/silica-encapsulated SERS marker is formed. A standard operating procedure for the formation of a polyelectrolyte/silica-encapsulated SERS marker is given in Example 10.

In a further aspect, the present invention relates to an in vitro method for analyzing a biological sample, the method comprising:
  (a) contacting the biological sample with at least one SERS marker as described herein above;
  (b) allowing binding of the binding molecule of the at least one SERS marker to at least one component of the biological sample;

(c) irradiating the at least one SERS marker bound to the at least one component so as to cause Raman scattering of the SERS marker; and (d) detecting the Raman scattering.

In general, the biological sample employed in accordance with the present invention may be derived from any biological source/organism or any kind of organic matter. Preferably, said organic matter is derived from living organisms. A suitable "biological sample" as employed herein includes, but is not limited to a biological sample comprising cell(s) or tissue(s). For example, the biological sample employed herein may be (a) virus(es), (a) prokaryotic cell(s), (a) plant cell(s) or tissue, (an) animal cell(s) or tissue or a body fluid. Such a biological sample may also comprise biological material of biopsies. The meaning of "biopsies" is known in the art. For instance, biopsies comprise cell(s) or tissue(s) taken, e.g. by the attending physician, from a subject as mentioned herein.

The biological sample may be or may be derived from a virus or a single- or multicellular organism. In the context of the present invention, the term "virus" means a biological infectious particle which can only replicate itself by infecting a host cell. Such a virus may be, for example, herpes simplex virus, human immunodeficiency virus, ebolavirus, papillomavirus, influenza A virus, SARS coronavirus, rhinovirus, borna virus, tobacco mosaic virus and T4 phage. Said single- or multicellular organism may be selected from the group consisting of bacteria, protists, fungi, plants and animals. The meaning of these terms is well known in the art.

In the context of the present invention, the term "procaryotic cell" particularly means prokaryotes comprising the evolutionary domains Bacteria and Archaea. Examples for such bacteria are *Neisseria* sp., *Streptococcus* sp., *Staphylococcus* sp., *Actinobacteria*, and *Escherichia coli*.

The biological sample may also be or be derived from a protist. In the context of the present invention the term "protist" particularly means single- to few-cellular eukaryotes. Particular "protists" are, for example, *Euglena* sp., *Amoeba* sp., *Paramecium* sp., *Toxoplasma* sp., *Ulva* sp., *Porphyra* sp., and *Macrocystis* sp.

The biological sample may also be or be derived from fungi. The meaning of the term "fungi" is known by the skilled person and is used accordingly in the context of the present invention. The term "fungi" means, for example, heterotrophic eucaryotes which digest their food externally, which are not able to perform photosynthesis and which usually have cell walls. Examples for "fungi" are *Penicillium* sp., *Agaricus* sp., *Phytophtora* sp. and *Amanita* sp.

The biological sample may also be or be derived from plants. In the context of the present invention the term "plant" particularly means phototrophic eucaryotes which comprise algae, bryophytes, ferns and higher plants such as gymnosperms and angiosperms. Plants to be used include but are not limited to maize, wheat, potato, tomato, tobacco and thale cress (*Arabidopsis thaliana*).

The biological sample employed herein may also be derived from an animal. More preferably, said sample is derived from a mammal. The meaning of the terms "animal" or "mammal" is well known in the art and can, for example, be deduced from Wehner and Gehring (1995; Thieme Verlag). In the context of this invention, it is particularly envisaged that biological samples are derived from organisms that are economically, agronomically or scientifically important or pose a possible threat to human health or the environment. Scientifically important organisms include, but are not limited to, mice, rats, rabbits, fruit flies like *Drosophila melagonaster* and nematodes like *Caenorhabditis elegans*.

The biological sample may also be derived or obtained from a primate or from a human being. The person skilled in the art is aware of the meaning of the terms "primate", "human" and "human being", and the like.

The biological sample to be employed in accordance with the present invention may also be derived from or is (a) cell(s), (a) tissue(s) or (a) body fluid(s). It is particularly envisaged that the cell, tissue or body fluid is derived from any one of the single- or multicellular organisms described herein. The biological sample may be derived from a single cell, a plurality of cells and a tissue. The term "cell" is well known in the art. The term "plurality of cells" means in the context of the present invention a group of cells comprising more than a single cell. Thereby, the cells out of said group of cells may have a similar function. Said cells may be connected cells and/or separate cells. The term "tissue" in the context of the present invention particularly means a group of cells that perform a similar function.

Non-limiting examples for animal cells are lymphatic cells, muscle cells, heart cells, nerve cells, cells from the spinal cord, brain cells, liver cells, kidney cells, cells from the intestinal tract, cells from the testis (e.g. Leydig cells and granulosa-lutein cells), cells from the urogenital tract, colon cells, skin cells, placenta cells, stem cells (embryonal, neuronal, and/or others) or primary or immortalized cell lines (lymphocytes, macrophages, or cell lines).

Examples for plant tissues are epidermis, vascular tissue and ground tissue. The term "plantal epidermis" in the context of the present invention means cells forming the outer surface of the leaves and of the young plant body. In the context of the present invention, the term "vascular tissue" means the primary components of vascular tissue, namely xylem and phloem. The term "ground tissue" means in the context of the present invention less differentiated tissue which performs photosynthesis and stores reserve nutrients. Accordingly, cells comprised in said tissues may be, for example, epidermal cells or mesophyll cells (such as cells comprised in the palisade layer or spongy layer). Of course, plant cells may also be meristematic cells, such as cambium cells.

Non-limiting examples for animal tissues are epithelium, connective tissue, muscle tissue and nervous tissue. The meaning of the terms "epithelium", "muscle tissue", "nervous tissue" and "connective tissue" are well known in the art. In the context of this invention "epithelium" particularly means tissues composed of layers of cells that cover organ surfaces such as surface of the skin and inner lining of digestive tract. The term "muscle tissue" particularly means in the context of the present invention muscle cells which contain contractile filament. Muscle tissue can be part of a smooth muscle, which is found in the inner linings of organs; part of a skeletal muscle, which is found attached to bone; or part of a cardiac muscle found in the heart. In the context of the present invention, the term "nervous tissue" particularly means a tissue comprising cells which form parts of the brain, spinal cord and peripheral nervous system. The term "connective tissue" particularly means in the context of the present invention a tissue which is involved in structure and support. Examples for connective tissue are blood, cartilage and bone. The cells and tissues to be employed in accordance with the present invention may also be cultured cells or tissues.

In the context of the present invention the term "body fluid" includes, for example, a fluid that is secreted or excreted from an animal or human body. However, a "body fluid", for example, of human or animal origin, may also normally not be excreted or secreted. Non-limiting examples of body fluids are selected from the group consisting of amniotic fluid, aqueous humour, bile, blood plasma, blood serum, cerumen, cowper's fluid, chyle, chyme, female ejaculate, interstitial fluid, lymph, menses, breast milk, mucus, pleural fluid, pus, saliva, sebum (skin oil), semen, sweat, tears, urine, vaginal lubrication, vomit, feces, cerebrospinal fluid, synovial fluid, intracellular fluid, and vitreous humour (fluid in the eyeball).

The biological sample may also be hair, hair follicle, feather, nail, fish or reptile scale and the like.

The at least one component of the biological sample to which the at least one SERS marker binds in accordance with the present invention may be any target molecule the binding molecule described herein above may bind to. The skilled person is capable of identifying binding molecules and corresponding target molecules said binding molecules bind to and vice versa. In particular, a target molecule to which the binding molecules of the present SERS markers can bind may be suitably selected from the various types of target molecules indicated above.

For example, the binding molecule being an antibody may bind to a corresponding antigen comprised in a biological sample. Correspondingly, the binding molecule being a hormone may bind to the corresponding hormone receptor or being a RNA it may bind to a homologous nucleic acid molecule.

In the context of the present invention, it is clear that the skilled person is readily in the position to contact the biological sample described herein above with at least one SERS marker and to allow binding of the SERS marker to at least one component. The biological sample or the component comprised in said biological sample may be isolated and/or concentrated and/or modified prior to said steps of contacting and binding. Corresponding methods of isolation, concentration or modification are well known in the art and may be deduced, for example from Sambrook and Russell (2001, Molecular Cloning: A Laboratory Manual, CSH Press, Cold Spring Harbor, N.Y., USA). However, it is also envisaged herein that a whole organism comprised in the biological sample, preferably a single-cellular to few-cellular organism, such as a virus, a bacterium or a protist, is contacted with the SERS marker and that the SERS marker binds to a component that is either at the surface of said organism or an internal part of said organism. It is to be understood that in case a whole organism is contacted with the SERS marker said organism is preferably killed before said step of contacting. The present in vitro method also comprises methods for analyzing biological samples comprising microorganisms, i.e. unicellular organisms.

Preferably, one SERS marker specifically binds to one component of the biological sample. Preferably several SERS markers are used, each SERS marker binding to a distinct component, i.e. a first SERS marker would then, for example, specifically bind to a first target molecule while a second SERS marker, preferably comprising a Raman-active reporter group dissimilar to the Raman-active reporter group of the first SERS marker, would specifically bind to a second target molecule. It is preferred that at least 2, 3, 4, 5, 6, 7, 8, 9, 10, 12, 15, 20 SERS markers bind specifically to a target molecule, wherein it is to be understood that said SERS markers preferably bind to different target molecules. It is, however, envisioned to employ up to 100 or even 1000 or more different specific SERS markers each comprising its own characteristic Raman-active reporter group. This type of multiplexing, wherein each SERS marker is distinguished from the other SERS markers by Raman-active reporter group and binding molecule, is particularly useful for imaging applications, such as Raman microscopy/spectroscopy and diagnostic means and methods as described herein below.

Different target molecules can be detected simultaneously by multiplexing after applying the steps of irradiating the SERS markers and detecting the Raman scattering. Accordingly, different target molecules of a kind, for example RNA molecules which need not be homologous to each other, can be detected simultaneously. However, it is also envisaged herein that various types of target molecules can be detected simultaneously, for example, proteins, RNA molecules and DNA. In a preferred embodiment the target molecules to be detected simultaneously are associated with the same gene, thus being, for example, gene products of said same gene, such as mRNA or protein.

In a further preferred embodiment, said target molecules are preferably associated with the same disease or phenotype, for example gene products of different genes which are associated with the same disease or phenotype.

The person skilled in the art also knows how to irradiate a SERS marker used in accordance with this invention and how to detect the Raman scattering, see, for example, Smith, Modern Raman Spectroscopy: A Practical Approach, Wiley, 2005; McCreery, Raman Spectroscopy for Chemical Analysis, Wiley, 2000. Kneipp, Surface-Enhanced Raman Scattering: Physics and Applications, Springer, 2006.

For example, if the component is a protein, contacting and binding can be performed by taking advantage of immunoagglutination, immunoprecipitation (e.g. immunodiffusion, immunelectrophoresis, immune fixation), western blotting techniques (e.g. (in situ) immuno histochemistry, (in situ) immuno cytochemistry, affinitychromatography, enzyme immunoassays), and the like. These and other suitable methods of contacting proteins are well known in the art and are, for example, also described in Sambrook and Russell (2001, loc. cit.)

For example, if the component is a DNA, contacting and binding can be performed by taking advantage of Southern blotting techniques (such as in situ hybridization) and the like. These and other suitable methods of contacting DNA are well known in the art and are, for example, also described in Sambrook and Russell (2001; loc. cit.)

For example, if the gene product is a mRNA, contacting and binding can be performed by taking advantage of Northern blotting techniques or PCR techniques, like in-situ PCR. These and other suitable methods for binding (specific) mRNA are well known in the art and are, for example, described in Sambrook and Russell (2001, loc. cit.).

In a particularly preferred embodiment the amount of the component, particularly of the gene products as defined herein (e.g. mRNA, protein), is to be determined using the SERS marker of the invention. In case the component is a protein, quantification can be performed by taking advantage of the techniques referred to above, in particular Western blotting techniques. Generally, the skilled person is aware of methods for the quantitation of polypeptides. Amounts of purified polypeptide in solution can be determined by physical methods, e.g. photometry. Methods of quantifying a particular polypeptide in a mixture rely on specific binding, e.g of antibodies. Specific detection and quantitation methods exploiting the specificity of antibodies comprise for example immunohistochemistry (in situ). Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction.

If the component is a mRNA, determination can be performed by taking advantage of northern blotting techniques, hybridization on microarrays or DNA chips equipped with one or more probes or probe sets specific for mRNA transcripts or PCR techniques referred to above, like, for example, quantitative PCR techniques, such as Real time PCR. A skilled person is capable of determining the amount of the component, in particular said gene products, by taking advantage of a correlation, preferably a linear correlation, between the intensity of a Raman signal and the amount of the component to be determined.

Non-limiting examples of gene products the amount of which is to be determined are cancer-specific tumor markers, such as CEA (carcinoembryonic antigen), CA19-9 or CA125 or tissue-specific tumor markers, such as PSA (prostate specific antigen), beta-HCG (human chorionic gonadotropin), AFP (Alpha-fetoprotein), AFP-L3 (lectin-reactive AFP) and Thyroglobulin. The SERS marker may also be used to determine the homozygous or heterozygous state of a biological sample in respect of at least one allele. For example, heterozygous carriers of autosomal recessive disorders, which do not show any symptoms can be detected. Said autosomal recessive disorders include but are not limited to anemia, cystic fibrosis, Tay-Sachs disease, chronic granulomatous disease, thalassemia, Bloom's syndrome, Alpha 1-antitrypsin deficiency, haemochromatosis types 1-3, Wilson's disease, homocystinuria, congenital adrenal hyperplasia, Dubin-Johnson syndrome, Fanconi anemia, galactosemia, phenylketonuria, albinism, rotor syndrome, pendred syndrome or Xeroderma pigmentosum.

A particular advantage of the SERS marker of the present invention is the detection of minute amounts of a component, e.g. DNA or gene products, because of the high sensitivity of the SERS marker.

A person skilled in the art knows how to determine whether a subject exhibits a mutation or a polymorphism in a gene by his common general knowledge and the teaching provided herein.

It is preferred that a mutation or a polymorphism is to be detected in the context of the present invention, which is associated with a particular disease or phenotype. In order to detect said mutation or polymorphism advantage can be taken of, for example, hybridizing techniques/PCR techniques using probes/primers representing the mutation or polymorphism to be detected or, for example, of sequencing approaches, e.g. nucleotide or protein sequencing approaches. These and other suitable methods of detecting a mutation or a nucleotide polymorphism are also well known in the art. The binding molecule bound to group Y may then be, for example, an oligonucleotide specifically recognizing a target molecule, so that the SERS marker of the present invention may be used as a (sequencing) primer. Accordingly, the SERS marker may be used for the detection of single nucleotide polymorphisms (SNP), short tandem repeats (STR), minisatellites and copy number variations. Preferably the SERS marker is used in accordance with the present invention for detection of (a) mutation(s) or (a) polymorphism(s) which is (are) associated with a disease.

The term "nucleotide polymorphism" refers to the occurrence of one or more different nucleotides or bases at a given location on a chromosome. Usually, polymorphisms are distinguished from mutations based on their prevalence. Sometimes a threshold of 1% prevalence in a population of individuals is considered for separating polymorphisms (more frequent) from mutations (less frequent). A single nucleotide polymorphism (SNP) is a polymorphism of a single nucleotide or base. The SNP database maintained at NCBI (http://www.ncbi.nlm.nih.gov/SNP/) divides SNPs into SNPs in the proximity of a known locus and such that are 5' further away than 2 kb from the most 5' feature of a gene and 3' further away than 500 bases from the most 3' feature of a gene. SNPs in the proximity of a known locus are further divided into SNPs occurring at a mRNA location and such that do not. SNPs occurring at a mRNA location comprise coding and non-coding SNPs.

It is understood that the term "polymorphism(s)" embraces polymorphisms in exons, introns and regulatory regions such as promoters. Polymorphisms in exons may be determined or analysed using genomic DNA or cDNA (or equivalently mRNA). Polymorphisms in introns or regulatory regions such as promoters may be determined or analysed using genomic DNA.

Said associating of polymorphism(s) with a disease state or disposition state refers to classifying of individuals and patients. The term "classifying" refers to the assignment of individuals or patients to two or more groups or classes. In other words, individuals, previously unclassified, get labelled by their respective class. The assigned class label may refer to parameters used for classification, e.g. polymorphisms, or may refer to parameters not used for classification because their values are not known beforehand, e.g. fast or slow response to therapy. In the first case, class discovery methods, e.g. clustering may be applied, whereas in the second case predictive classification methods are used. Classification may be done manually by a trained person or by a computer program provided with the values of the parameters used for class distinction. Patients have to give informed consent. Data have to be handled and kept secret in accordance with national laws.

It is also envisaged herein that the SERS marker may be used in drug screening, for example to determine increased erythropoietin levels or testosteron levels of blood samples of athletes.

In a further aspect the invention relates to the use of the SERS marker in immunoassays, cytometry systems, flow cytometry, high-throughput screening, high-speed screening systems, chemical array systems, biomolecule array systems, biosensing systems, biolabeling systems, gene expression systems, protein expression systems, medical diagnostic systems, diagnostic libraries, microfluidic systems, DNA/RNA assays, microarrays, proteomics, protein biochemistry, imaging, labelling and detection and analyses of blood and tissue samples. The meaning of the terms "immunoassays", "flow cytometry", "high-throughput screening", "DNA/RNA assays", "microarrays", "proteomics", "protein biochemistry" is well known in the art and may be deduced, for example, from Lottspeich (Bioanalytik, Spektrum Akademischer Verlag, 1998); Raem (Immunoassays, Spektrum Akademischer Verlag, 2007); Rehm (Der Experimentator: Proteinbiochemie/Proteomics, Spektrum Akademischer Verlag, 2006); Luttmann (Der Experimentator: Immunologie, Spektrum Akademischer Verlag, 2006). The terms "labelling and detection" refer to the target molecules described herein above that can be labelled and detected using the SERS marker of the invention while the term "imaging" is a particular mode of detection giving rise for example to an image of a biological sample such as a tissue or cell after the steps of contacting and binding described above. Analyses of blood and tissue samples, by taking advantage of Northern Blotting, Southern blotting, Western blotting or PCR techniques, and the like, are described exemplarily herein above.

Further, the invention relates to the use of the compound or the SERS marker according to the invention for the manufacture of a diagnostic composition for immunoassays, flow cytometry, high-throughput screening, DNA/RNA assays, microarrays, proteomics, protein biochemistry, imaging, labelling and detection and analyses of blood and tissue samples.

The present invention also provides a diagnostic composition comprising the SERS marker of the invention. The dosage regimen/administration mode the SERS marker to be employed/used herein or the diagnostic composition comprising it will be determined by the attending physician and clinical factors. As is well known in the medical arts, dosages for any one patient depends upon many factors, including the patient's size, body surface area, age, the particular compound to be administered, sex, time and route of administration, general health, and drugs being administered concurrently. A person skilled in the art is aware of or able to determine suitable doses of the SERS markers of the present invention. The diagnostic composition will be formulated and dosed in a fashion consistent with good medical practice, taking into account the clinical condition of the individual subject, the site of delivery of the diagnostic composition, the method of administration, the scheduling of administration, and other factors known to practitioners. The "effective amount" of the diagnostic composition for purposes herein is thus determined by such considerations.

The skilled person knows that the effective amount of diagnostic composition administered to a subject will, inter alia, depend on the nature of the compound. For example, if said compound is a (poly)peptide or protein the total diagnostically effective amount of diagnostic composition administered parenterally per dose can, for example, be in the range of about 1 µg protein/kg to 10 mg protein/kg of patient body weight. More preferably, this dose is at least 0.01 mg protein/kg, and most preferably for humans between about 0.01 and 1 mg protein/kg. If given continuously, the diagnostic composition can, for example, be administered at a dose rate of about 1 µg/kg/hour to about 50 µg/kg/hour, for example by continuous subcutaneous infusions, using, for example, a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Diagnostic compositions of the invention may be administered orally, rectally, parenterally, intracisternally, intravaginally, intraperitoneally, topically (as by powders, ointments, drops or transdermal patch), bucally, or as an oral or nasal spray.

Diagnostic compositions of the invention preferably comprise a diagnostically acceptable carrier. By "diagnostically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The diagnostic composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988). Sustained release diagnostic composition also include liposomally entrapped compound. Liposomes containing the diagnostic composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the diagnostic composition is formulated generally by mixing it at the desired degree of purity, in a unit dosage injectable form (solution, suspension, or emulsion), with a diagnostically acceptable carrier, i.e., one that is non-toxic to recipients at the dosages and concentrations employed and is compatible with other ingredients of the formulation.

Generally, the formulations are prepared by contacting the components of the diagnostic composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the diagnostic composition are preferably sterile. Sterility is readily accomplished by filtration through sterile filtration membranes (e.g., 0.2 or 0.4 micron membranes). Components of the diagnostic composition generally are placed into a container having a sterile access port, for example, an intravenous solution bag or vial having a stopper pierceable by a hypodermic injection needle.

The components of the diagnostic composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

In a further preferred aspect of the present invention, the diagnostic composition of the present invention may further comprise (an) instruction manual(s) which guide the skilled person how to diagnose a disease as defined herein. Particularly, said instruction manual(s) may comprise guidance how to use or apply the methods of diagnosing a disease provided herein.

To this end, the diagnostic composition of the present invention may comprise a kit further comprising the substances/chemicals and/or equipment suitable for the corresponding diagnostic assessment and, optionally, a carrier, excipient, solvent, diluent, buffer for stabilizing and/or storing the compounds.

In a further embodiment, the invention relates to a SERS marker for use in diagnosis, wherein the diagnosis comprises the steps of:
(a) administering at least one SERS marker to a subject;
(b) allowing binding of the binding molecule of the at least one SERS marker to a part of the subject;
(c) irradiating the at least one SERS marker bound to the part of the subject so as to cause SERS/Raman scattering of the SERS marker; and
(d) detecting the SERS/Raman scattering.

SERS data may, for example, be acquired from the same sample location, different sample locations, or be acquired in a spatially resolved experiment (mapping or imaging). In each case, the SERS data evaluation requires the analysis of spectra and/or images (in the case of mapping/imaging data, sometimes the term "hyperspectral image cube" is used: it refers to microspectroscopic images as a function of vibrational wavenumber).

For SERS marker (i.e. also target molecule) localization and quantification, the knowledge of the characteristic vibrational spectroscopic signature of the corresponding SERS markers is required. In a very simple implementation, a single Raman/SERS band occurs at a specific wavenumber position at which all other SERS markers do not have a spectral contribution. The SERS signal above baseline is then a direct measure for the amount/concentration of the SERS marker at that particular location. This simple uni-variate approach may not be feasible in the case of many SERS markers so that other, more sophisticated approaches have to be used. For example, chemometrics—the application of mathematical procedures to chemical data sets—provides various tools for the analysis of complex data sets and extracting chemically meaningful information from it (see, for example, Otto, Chemometrics, Wiley, 1999). This may, for example, require to establish a training set and a robust (for example, multivariate) procedure for data analysis. A central aim of the entire SERS data evaluation procedure is to provide quantitative (and in the case of mapping/imaging experiments also spatially resolved) information on the presence/amount (and/or location) of the set of distinct SERS markers used in the corresponding experiment. Various software platforms for generating/extracting such information from spectroscopic data sets exist. Examples for software products include Matlab (available from The MathWorks) and ENVI/IDL (available from ITT Visual Information Solutions and other providers).

The term "part of the subject" comprises for example the components described in the context of the biological sample hereinabove. A preferred subject/patient is a mammalian subject/patient, more preferably a primate subject/patient, most preferably a human being, preferably in need of diagnosis.

The amount of the component of a subject, described herein may be elevated, normal or decreased compared to "normal" amounts. If the component is a gene product, it may be "over-expressed", "normally expressed" or the expression may be "reduced" compared to "normal expression". The term "over-expression" denotes an expression level of said gene product, preferably mRNA or protein, which is elevated in comparison to normal expression. The term "normal expression" refers to a reference expression level determined in one or more samples from healthy individuals. The term "reduced expression" is a expression level which is reduced compared to "normal" expression levels. The samples with "normal expression" are preferably from healthy tissue corresponding to the tissue affected by the disease or condition under consideration. Samples may be drawn from a mixed population, from a fraction of the population, wherein the population has previously been stratified according to one or more parameters, or from healthy regions of the tissue affected by the disease or condition from the same patient. Statistical methods known in the art may be used in order to assign significance values and confidence intervals to the measured expression and over-expression data. The definitions given herein above and below with respect to "over-expression", "normal expression" or "reduced expression" apply with respect to "elevated" amount, "normal" amount and "reduced" amount of components or target molecules, respectively, mutatis mutandis.

A skilled person is able to employ to correlate data obtained in the above methods with pathological conditions. Thus, the present methods can be useful for the diagnosis of a disease or disorder selected from, for example, infectious (contagious) diseases, proliferative diseases, neurodegenerative diseases, cancers, psychological disorders, metabolic diseases, autoimmune diseases, sexually transmitted diseases, gastro-intestinal disorders, pulmonary disorders and cardiovascular disorders.

In one embodiment, the present invention relates to a method of diagnosing in a subject suspected of suffering from a disease as defined herein above or suspected of being prone to suffering from a disease as defined herein above, comprising the steps of
(a) administering at least one SERS marker as described and defined herein above to a subject;
(b) allowing binding of the binding molecule of the at least one SERS marker to a part of the subject;
(c) irradiating the at least one SERS marker bound to the part of the subject so as to cause Raman scattering of the SERS marker;
(d) detecting the Raman scattering of the at least one SERS marker; and
(e) comparing the Raman scattering of said at least one SERS marker detected in (d) with a reference Raman scattering of said at least one SERS marker detected in a control subject (healthy subject),
wherein said disease is diagnosed when said Raman scattering detected in (d) differs from said reference Raman scattering.

In a further embodiment, the present invention relates to a method of diagnosing in a subject suspected of suffering from a disease as defined herein above or suspected of being prone to suffering from a disorder as defined herein above, comprising the steps of
(a) contacting at least one SERS marker as described and defined herein above to a cell or tissue sample obtained from said subject;
(b) allowing binding of the binding molecule of the at least one SERS marker to at least one component of said cell or tissue sample;
(c) irradiating the at least one SERS marker bound to the at least one component of said cell or tissue sample so as to cause Raman scattering of the SERS marker;
(d) detecting the Raman scattering of the at least one SERS marker; and (e) comparing the Raman scattering of said at least one SERS marker detected in (d) with a reference Raman scattering of said at least one SERS marker detected in a cell or tissue sample obtained from a control subject (healthy subject), wherein said disease is diagnosed when said Raman scattering detected in (d) differs from said reference Raman scattering.

The present invention overcomes the shortcomings of approaches known in the art for diagnosing diseases, in particular by providing highly sensitive SERS markers for diagnosing diseases/disorders and for predicting/monitoring the response to corresponding treatments (for example by using peripheral blood samples). The SERS markers to be used in the diagnosing methods of the present invention is preferably comprised in a diagnostic composition as described herein.

The term "Raman scattering" as used herein refers to a characteristic vibrational spectroscopic signature of at least one SERS marker as described elsewhere herein. The terms "Raman scattering" and "SERS scattering" referred to herein above can be used interchangeably. The SERS markers provided in context of the present invention and to be used in the diagnosing methods may be useful in determining in (a cell or tissue sample obtained from) a subject/patient suspected of suffering from (or suspected of being prone to suffering from) a disease as described herein above a difference in the Raman scattering detected in said subject/patient and in a healthy subject/patient. A difference in the Raman scattering may be a difference in the intensity of (a) specific Raman/SERS band(s) and/or in the presence of (a) specific Raman/SERS band as described herein above. In a very simple implementation, the presence of such (a) band(s) indicates the presence of (a) target molecule(s), wherein the presence of said target molecule is indicative for (a) disease(s). Vice versa, absence of such (a) band(s) may, in specific aspects, indicate the presence of (a) disease(s). By taking advantage of the difference in the intensity of (a) specific Raman/SERS band the amount/concentration of (a) target molecule(s) can be determined, wherein the difference is indicative of the presence or absence of (a) disease(s). A person skilled in the art is in the position to evaluate differences in the Raman scattering and to diagnose in accordance with the present invention the presence or absence of (a) disease.

For example, a difference in the Raman scattering may reflect a difference in the expression level or the amplification status of (a) gene(s), wherein an aberrant expression level/amplification status of (a) gene(s) or sequence(s) coding for an RNA transcript (e.g. an miRNA locus) is indicative for (a) disease(s). A person skilled in the art will know the gene(s) whose aberrant expression level/amplification status is indicative for (a) specific disease(s). However, not only the expression level/amplification status may be assessed but also the level of metabolites, antibodies, hormones, cell types (such as lymphocytes, erythrocytes, blood platelets), microorganisms (e.g. bacteria, protists) and the like, wherein an aberrant level is indicative for (a) specific disease(s). A person skilled in the art will be aware of further substances/compounds wherein an aberrant level is indicative for (a) specific disease(s) or may deduce such substances from standard textbooks. Based on the disclosure of the present invention and his common general knowledge an artisan will also be aware of means and methods for detection of aberrant levels of the above-mentioned components (i.e. target molecules) using the SERS marker of the present invention. Exemplary components and methods of detection are also described herein above, in particular in context of the in vitro method for analyzing a biological sample and diagnostic compositions.

It is to be understood that in the diagnostic methods described herein not only the level of (a) substance(s) or the expression level/amplification status of (a) gene(s) as defined herein above in a biological sample (e.g. a cell sample, tissue sample or biopsy sample) obtained from a subject suspected of suffering from a disease as defined herein above or suspected of being prone to suffering from a disease as defined herein but also in said subject itself may be determined in accordance with the present invention. Accordingly, the present invention relates in specific aspects to in vivo or in vitro diagnostic methods. For example, in vivo diagnosis may be particularly advantageous when size or location of e.g. (a) tumor(s) (or metastases) in a body is to be identified or when the site of a bacterial and/or viral infection is to be identified.

Generally, the skilled person is readily in the position to deduce a "control subject/patient" in accordance with the invention. If required, the "control subject/patient" may, for example, be weight-, age- and/or gender-matched with respect to the subject/patient in/for which the disease(s) is to be diagnosed or the efficacy of a treatment of a said disease is to be monitored/predicted in accordance with the present invention.

In particular with respect to the means, methods and uses of diagnosing the above-described disease(s), the control subject/patient preferably is a healthy subject, i.e. a subject/patient having e.g. a normal expression level of said at least one marker gene as described in accordance with this invention, and/or a subject/patient not suffering from the disease to be diagnosed. In this context, "normal" expression level means lying within the "normal range" of expression level different healthy patients exhibit. What a "normal" or "normal range" of expression level of the herein described marker genes is can be deduced by the skilled person, for example by consulting corresponding literature, and/or can also be readily be deduced on the basis of the teaching provided herein and/or his common general knowledge.

In accordance with the above, the reference expression level of the at least one marker gene, with respect to the means, methods and uses of diagnosing a disease, is that determined in (a sample of) the corresponding healthy control subject, i.e. is the "normal" expression level.

As mentioned above, a disease is diagnosed in accordance with this embodiment of the invention, when the expression level of at least one marker gene as described, herein is different from the above described reference expression level. Thereby, it is clear that different means higher or lower, depending on whether the disease comes along with an up- or down-regulated expression level of said at least one marker gene.

In this context, different, higher or lower means different, higher or lower than the normal (range of) expression level of said at least one marker gene. For example, different, higher or lower means at least 1.5 fold, at least 2 fold, at least 2.5 fold, at least 3 fold, at least 4 fold, at least 5 fold, at least 7 fold, at least 10 fold, at least 15 fold, at least 25 fold, at least 50 fold, at least 100 fold, at least 200 fold different, higher or lower, wherein the higher values are preferred.

If, in which direction (i.e. higher or lower), and to which extent the expression level of at least one marker gene as described herein differs from its corresponding reference expression level, can easily be deduced by the skilled person based on the teaching provided herein and the common general knowledge. Accordingly, it is possible for each marker gene particularly described herein, whether a given difference between the reference expression level and the expression level of a subject/patient to be diagnostically assessed is diagnostic for a disease.

With respect to the means, method and uses of diagnosing a disease, the control subject/patient may also be a subject/patient suffering form the disease; i.e. having an aberrant expression level of (a) marker gene(s).

In accordance with this, the reference expression level of the at least one marker gene is the one determined in (a sample of) the corresponding diseased control subject, i.e. is the "aberrant" expression level.

A disease is diagnosed in accordance with this embodiment of the invention, when the expression level of the at least one marker gene as described herein is (substantially) the same than the above-described reference expression level, i.e. differs less than 1.5 fold from said reference expression level.

The possibility of recognizing (aberrant) changes of expression level of (a) marker gene(s) early, provides several advantages, like a higher lifespan/likelihood of survival of the subject/patient (for example due to the notice of possible treatment failures and a corresponding change of the treatment regimen) and the possibility of a more efficient therapy (for example due to the possibility to avoid/recognize treatment failures early and, hence, to correspondingly change the treatment regimen early in therapy, i.e. to timely switch to a more suited inhibitor, to discontinue an expensive, ineffective treatment early after diagnosis and to opt for alternative therapy).

In context of the above embodiments of this invention, "early" particularly means prior to (the onset of) a (complete or partial) cytogenetic or haematological response or a response measured by a Raman imaging technique to be used in accordance with the present invention and/or prior to the outbreak of a disease (or susceptibility thereto). The term "susceptibility to a disease" as used herein refers to a subject/patient being prone to suffering from a disease, e.g. a subject having a hereditary risk for a disease.

For example, "early" diagnosing a disease may be at least 1, at least 2, at least 3, at least 4, at least 5, at least 6, at least 7, at least 10, or at least 14 days prior to (the onset of) a (partial) cytogenetic or haematological response or a response measured by a imaging technique and/or prior to the outbreak of a disease (or susceptibility thereto), wherein the longer periods are preferred.

The SERS marker of the present invention may also be useful in monitoring or predicting the efficacy of a treatment of a disease suffering from said disorder or being prone to suffering from said disorder. The definitions and explanations given herein above in respect of diagnosing a disease apply here, mutatis mutandis, in respect of monitoring or predicting the efficacy of a treatment of a disease.

For example, an aberrant expression level of at least one marker gene may be present in a sample before start of the treatment of a disease. During or after treatment of the disease, the diseased cells having said aberrant expression level are erased or otherwise depleted. Thus, the absence of a detectable aberrant expression level of at least one of said genes in a sample (cell samples/biopsy samples and the like) obtained from a subject/patient or in a subject/patient during or after treatment of a disease is indicative of the efficacy of the treatment.

It is particularly preferred in this context that the control subject/patient is subjected to the same treatment of the disease described and defined herein as the subject/patient itself and/or that it is known whether the control subject/patient is a responder or non-responder to this treatment. Whether a subject/patient is a "responder" or "non-responder" with respect to a certain kind of treatment/therapy of the disease can be evaluated by the skilled person on the basis of his common general knowledge and/or the teaching provided herein. In particular, a "responder" may be a subject/patient whose cytological/haematological parameters and/or (aberrant) marker gene expression level(s))/change towards the their "normal" (expression) level(s) (in a sufficient manner) upon the treatment/therapy.

In one embodiment disclosed herein, the present invention relates to the use of a (transgenic) cell or a (transgenic) non-human animal having at least one marker gene as defined herein for screening and/or validation of a medicament for the treatment of (a) disease as described herein. The term "cell" as used in this context may also comprise a plurality of cells as well as cells comprised in a tissue. A cell to be used may, for example, be a primary tumor cell. The tumor cell or cell to be used in the screening or validation method may be obtained from samples from a (transgenic) non-human animal suffering from the disease. The tumor cell or cell may also be obtained from patient samples (e.g. biopsies), in particular a biopsy/biopsies from a patient/subject suffering from the disease. Accordingly, the tumor cell or cell may be a human tumor cell or cell. Again, such a cell to be used in the present screening or validation methods may be comprised in a tissue or tissue sample, like in a sample biopsy.

The used non-human animal or cell may be transgenic or non transgenic. "Transgenic" in this context particularly means that at least one of the marker genes as described or defined herein is over- or under-expressed or that the gene product(s) of said marker gene(s) has (have) a higher or lower activity.

"Transgenic" in this context may also mean that (a) marker gene(s) is (are) over- or under-expressed, and/or that the activity of the gene product(s) of said marker gene(s) in the transgenic non-human animal or a transgenic cell is enhanced or decreased. A preferred (transgenic) non-human animal or (transgenic) cell in context of the invention suffers from a disease for the treatment of which the medicament is to be screened and/or validated. For example, if a medicament for the disease is to be screened and/or validated, the (transgenic) non-human animal or (transgenic) cell is particularly intended to suffer from the disease.

The term "transgenic non-human animal" or "transgenic cell" as used herein refers to a non-human animal or cell, not being a human, that comprises genetic material different from the genetic material of a corresponding wild-type animal/cell. "Genetic material" in this context may be any kind of a nucleic acid molecule, or analogues thereof, for example a nucleic acid molecule, or analogues thereof as defined herein. "Different" in this context means additional or fewer genetic material with respect to the genome of the wild-type animal/cell and/or rearranged genetic material, i.e. genetic material present at a different locus of the genome with respect to the genome of the wild-type animal/cell. An overview of examples of different expression systems to be used for generating transgenic cell/animal is, for instance, contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440).

In a preferred embodiment, the (transgenic) non-human animal or (transgenic) cell is or is derived from a mammal. Non-limiting examples of the (transgenic) non-human animal or derived (transgenic) cell are selected from the group consisting of a mouse, a rat, a rabbit, a guinea pig and a *Drosophila*.

Preferably, the (transgenic) cell in accordance with this invention may be an animal cell, for example, a non-human animal cell. However, also human cells are envisaged to be used as cells in context of the present invention. In a non limiting example, such cell may be an embryonic stem cell (ES cell), particularly a non-human animal ES, like, for example, a mouse or rat ES cell. The (transgenic) cell as described herein, particularly the ES cell, may also be used for generating the (transgenic) non-human animal as described herein. The ES cell technology for generating transgenic animals is well known in the art and for example is described in Pirity et. al. (Methods Cell Biol, 1998, 57:279).

Generally, the (transgenic) cell may be a prokaryotic or eukaryotic cell. For example, the (transgenic) cell, may be a bacterial, yeast, fungus, plant or animal cell. In general, the transformation or genetically engineering of a cell with a nucleic acid construct or vector can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

The (transgenic) non-human animal or (transgenic) cell as described or defined in context of this invention is particularly useful in methods for screening and/or validation of a medicament for the treatment of cancers as defined and described herein.

These screening methods may, in particular, performed in vivo using, for example, (transgenic) animals as described herein (e.g. rats, mice and the like) and/or animals comprising (a) diseased cell(s), (a) tissue(s) or (a) cell culture(s). Said (a) cell(s), (a) tissue(s) or (a) cell culture(s) may, for example, be obtained/derived from (a) diseased cell(s)/tissue(s). In particular, said (a) cell(s), (a) tissue(s) or (a) cell culture(s) may be obtained from a subject/patient suffering from the disease. These in vivo screening methods may in particular comprise measuring and determining differences progression of the disease. For example, if the disease is a cancer differences in tumor volume, for example, in the (transgenic) animals described herein above, may be measured and determined.

The corresponding definitions and descriptions provided above, for example with respect to "marker gene", "therapy/treatment", "efficacy", "disease" or "susceptibility" thereto, "(control) subject/patient", "(transgenic) non-human animal" or "(transgenic) cell", "expression level", "reference expression level" etc., apply here, mutatis mutandis. Particularly the relevant definitions and descriptions provided above with respect to "control subject/patient" also apply to the "control (transgenic) non-human animal" or "(transgenic) cell", mutatis mutandis.

In context of this invention, "screening and/or validation of medicaments" means, on the one hand, whether a given set of compounds comprises one or more compound(s) that can function as (a) medicament(s), and/or, on the other hand, whether (a) given compound(s) can function as (a) medicament(s). It is particularly intended that the medicaments to be screened and/or validated in context of this invention are medicaments for the treatment, prevention and/or amelioration of a cancer as defined herein.

The skilled person is readily in the position to put this embodiment of the present invention into practice. For example, by doing so, the compound(s)/medicament(s) to be screened and/or validated may be administered to the non-human (transgenic) animal or cell described herein, and, afterwards (for example after a certain period of time sufficient to allow a compound to effect on a cancer as described herein), it is analyzed whether the cancer, or a symptom thereof, of said animal/cell is ameliorated.

The present invention also relates to a kit for carrying out the methods or uses of this invention. For example, said kit particularly comprising (an) SERS marker(s) of the present invention required for specifically determining the expression level of said at least one marker gene as defined herein. Moreover, the present invention also relates to the use of (an) SERS marker(s) compound(s) required for specifically determining the expression level of said at least one marker gene as defined herein for the preparation of a kit for carrying out the methods or uses of this invention. On the basis of the teaching of this invention, the skilled person knows which compound(s) is(are) required for specifically determining the expression level of said at least one marker gene as defined herein. For example, such compound(s) may be (a) "binding molecule(s)", like, for example, (a) "binding molecule(s)" as defined herein-above. Particularly, such compound(s) may be (a) (nucleotide) probe(s), (a) primer(s) (pair(s)), (an) antibody(ies) and/or (an) aptamer(s) specific for at least one marker gene as described herein or for a product thereof. In a preferred embodiment, the kit (to be prepared in context) of this invention is a diagnostic kit.

In a particularly preferred embodiment of the present invention, the kit (to be prepared in context) of this invention or the methods and uses of the invention may further comprise or be provided with (an) instruction manual(s). For example, said instruction manual(s) may guide the skilled person (how) to determine the (reference) expression level of (a) marker gene(s) described herein, i.e. (how) to diagnose a disease or a susceptibility thereto, (how) to monitor the efficacy of a treatment of a disease or a susceptibility thereto or (how) to predict the efficacy of a treatment of a disease disorder or a susceptibility thereto in accordance with the present invention. Particularly, said instruction manual(s) may comprise guidance to use or apply the herein provided methods or uses.

The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) compound(s) required for specifically determining the expression level of said at least one marker gene as defined herein.

These and other embodiments are disclosed and encompassed by the description and examples of the present invention. Literature concerning any one of the methods, uses, kits and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

Furthermore, the term "and/or" when occurring herein includes the meaning of "and", "or" and "all or any other combination of the elements connected by said term".

The present invention is further described by reference to the following non-limiting figures and examples.

The figures show:

FIG. 1.

Comparison of characteristic line widths for fluorescence and Raman bands. Because the characteristic line width for conventional organic chromophores is about 20 to 50 nm, typically three distinct fluorophores can be detected simultaneously (top). Raman bands have a full width at half maximum of typically 2 to 20 cm$^{-1}$ which is about two orders of magnitude smaller. As an example, the Raman spectrum of benzene is shown (bottom, $\lambda_{exc}$=514.5 nm). The laser excitation line of 514.5 nm in this example corresponds to 0 cm$^{-1}$ in the Raman spectrum.

FIG. 2.

Surface-enhanced Raman scattering (SERS) spectroscopy for the highly sensitive detection of antigens (proteins) in immunoassays. SERS markers are covalently attached to the antibody and the noble metal (e.g. gold) nanoparticle. Immobilization of antigens is achieved by capture antibodies on a gold coated glass surface. Star: Raman-active reporter group; Y: antibody; Square: antigen.

FIG. 3.

Section of the surface of a gold particle covered by a self-assembled monolayer (SAM). The Raman-active reporter molecules are conjugated to the metal surface via sulphur atoms. In this example, the aromatic rings are stabilized by π-π stacking interactions.

FIG. 4.

Example of a SERS marker comprising a moiety comprising structure (Ia) or (IIa).

FIG. 5.

Schematic representation of a SERS marker comprising moieties comprising structure (Ia) and moieties comprising structure (IIa). Two different situations are illustrated. (top): Structure (IIa) does not contain a group Sp*; (bottom): Structure (IIa) contains a group Sp*.

FIG. 6.

Schematic representation of a silica-encapsulated SERS marker with a functionalized silica shell. The metal particle is covered by the self-assemble monolayer which is, in turn, covered by the encapsulant. Spacer groups are shown on the outermost surface.

FIG. 7.

Electronic absorption spectrum (UV-VIS region) of the gold nanoshells in water (solid line), in DMF (dashed line), and gold nanoshells with SAM of Example 2 in DMF (dotted line).

FIG. 8.

Raman/SERS spectrum of the hollow gold nanoshells of Example 2 with a SAM comprising the Raman marker in dimethylformamide (top) and with a SAM comprising the Raman marker with a protective silica shell (bottom) in water. Excitation wavelength: 633 nm

FIG. 9.

Raman/SERS spectrum of the hollow gold nanoshells of Example 5 containing the mixed/dual SAM (bottom). Raman/SERS spectrum after NHS activation (middle). Raman/SERS spectrum after antibody conjugation (top). Excitation wavelength: 633 nm

FIG. 10.

Electronic absorption spectrum (UV-VIS region) of gold nanoshells in water (solid line), after functionalization with a mixed/dual SAM (dashed line), and after subsequent conjugation of the SERS marker to PSA antibodies (dotted line), cf. Example 5.

FIG. 11.

Transmission electron microscopy (TEM) pictures of encapsulated SERS markers with silica covalently bound to the SAM, cf. Example 2.

FIG. 12.

TEM pictures of gold nanoshells.

FIG. 13.

Electronic absorption spectrum (UV-VIS region) of the gold nanoshells in water (solid line), and after subsequent functionalization with a SAM and silica encapsulation (Example 4) in water (dashed line) and in isopropanol (dotted line).

FIG. 14.

TEM pictures of silica-encapsulated SERS markers, cf. Example 4
A+B: silica shell thickness about 10 nm;
C: silica shell thickness about 25 nm, due to greater amount of tetraethoxysilicate (TEOS) added.

FIG. 15.

Multiplexing with four different SERS markers/Raman-active reporter molecules (from top to bottom) as illustrated by the corresponding Raman/SERS spectra. 5,5'-dithiobis(2-nitrobenzoic acid), mercaptobenzoic acid, 5,5'-dithiobis(2-bromobenzoic acid), and 6-hydroxy-naphthylsulfide.

FIG. 16.

Kinetics of self-assembled monolayer formation, cf. Example 6. The SERS intensities of the 1340 cm$^{-1}$ peak of DTNB relative to the 882 cm$^{-1}$ peak of the solvent ethanol are plotted against the reaction coordinate (circles) and fitted with an exponential function (solid line).

FIG. 17.

Influence of surface coverage on the brightness of SERS markers: complete SAM (dashed line) compared to sub-monolayer coverage (solid line) with MBA. SERS signals of the Raman-active reporter (MBA) were normalized to the Raman band of ethanol at about 882 cm$^{-1}$. The arrows mark the SERS bands of MBA.

FIG. 18.

Influence of the SERS substrate: Au/Ag nanoshells compared with Au nanospheres (SERS signals from DTNB are marked with arrows).

FIG. 19.

Mie calculations: calculated extinction spectra of a gold nanosphere (solid line) and a gold nanoshell (dashed line).

FIG. 20.

Transmission electron microscopy (TEM) image of a SERS marker batch prepared from 2-cyanoethyltrimethoxysilane, following the teachings of US 2006/0054506 A1.

The examples illustrate the invention.

EXAMPLE 1

Synthesis of the SERS marker unit
2,2'-Dichloro-5,5'-dithiobis(benzoic acid)

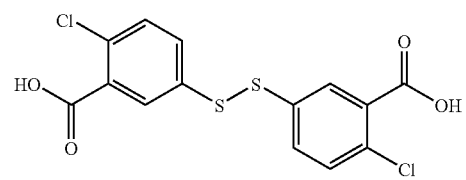 [SMILES: O=C(O)c1cc(SSc2ccc(Cl)c(C(=O)O)c2)ccc1Cl]

A solution of 5-amino-2-chlorobenzoic acid (2.0 g, 11.6 mmol), NaOH (0.46 g, 11.6 mmol) and NaNO$_2$ (0.80 g, 11.6 mmol) in 15 ml water is cooled to 0° C. This solution is slowly added to concentrated hydrochloric acid under stirring. The reaction temperature must not exceed 5° C. After stirring at 0° C. for 1 h, the solution is neutralized with a 1:1 mixture of $Na_2CO_3$ and sodium acetate. The solution of this diazonium salt kept at 0° C. is slowly added to a 80° C. hot solution of potassium xanthogenate (5.6 g, 35 mmol, 3 eq) in 20 ml water. After stirring 2 h at 75° C., the solution is made acidic (pH 3) at room temperature, yielding a solid product. The supernatant is decanted, the solid is solved in 9 ml of 10% NaOH solution and subsequently stirred for 2 h under reflux. After the addition of concentrated hydrochloric acid in the cold, a solid product precipitates, which is washed with water and a solution of $NaHSO_4$ after filtration. The solid product is solved in 10 ml methanol and oxidized to the disulfide at room temperature over night, employing oxidizing agents such as diluted $H_2O_2$ solution, Fe (III) or iodine. The solvent is removed under vacuum and the yellow solid is purified on a silica column (eluant: dichloromethane, 3% methanol, 1% trifluoro acetic acid) (yield: 1.09 g, 3 mmol, 25%). $R_f$(dichloromethane, 3% methanol, 1% trifluoro acetic acid): 0.2.

$^1$H-NMR (400 MHz, DMSO, 27° C.): δ=7.58 (d, 2H, $^2J$=8.48 Hz, 5-H), 7.67 (dd, 2H, $^2J_{4H5H}$=8.48, $^2J_{4H2H}$=2.40, 4-H), 7.90 (d, 2H, $^2J$=2.40 Hz, 2-H).

EXAMPLE 2

5,5'-Dithiobis(2-nitro(3-trimethoxysilyl)propylbenzamide as a Self-Assembled Monolayer (SAM) on Hollow Gold Nanospheres with Subsequent Silica Encapsulation and Amino-Functionalization of the Silica Shell (1) Synthesis and Purification of the Amide Formed in the Reaction of 5,5'-dithiobis(2-nitrobenzoic Acid) and Aminopropylsilane Via the Corresponding Acyl Chloride The educt and SERS marker unit 5,5'-dithiobis(2-nitrobenzoic acid) is dissolved in a mixture of organic solvents (182.2 mg in 10 ml dry dichloromethane and 1 ml dry THF) under nitrogen atmosphere. Oxalyl chloride (0.24 ml) and catalytic amounts of dimethylformamide (1 drop) are added and the reaction mixture is stirred for 2 h under reflux at about 55-60° C. After cooling down, the solvent mixture is removed under vacuum. The reaction products are dissolved in 1 to 2 ml dry dichloromethane. 3-aminopropyltrimethoxysilane (0.178 ml) and then triethylamine as an auxiliary base are added to the dissolved acyl chloride; the reaction mixture is stirred at room temperature over night (14 h). A yellow-orange solid is obtained after removal of the solvent mixture. Purification is achieved by column chromatography. Because the —Si(OMe)$_3$ moiety is sensitive to hydrolysis, the purification steps are also performed under a protective gas (nitrogen) atmosphere employing dry (absolute) solvents. A mixture (specifications in % vol) of 95% dry dichloromethane and 5% dry methanol is used for dissolving the solid and as a mobile phase for column chromatography. Dry silica is used as the stationary phase. The retention factor ($R_f$ value) for the amide is about 0.6, while it is zero for the educt 5,5'-dithiobis(2-nitrobenzoic acid). The column fractions containing the product are combined and the solvent is removed under vacuum.

$^1$H-NMR: three aromatic protons: (d=doublet) at 8.0 ppm (2H), (dd=doublet of doublets) at 7.6 ppm (2H), (d) at 7.5 ppm (2H); amide proton: (t=triplet) at 6.3-6.4 ppm (2H); methyl protons of the Si(OMe)$_3$ units: at 3.6 ppm (18H); alkyl protons: (dd or dt) at 3.5 ppm (4H): $CH_2$—$CH_2$—NH—CO, (tt=triplet of triplets) at 1.7-1.8 ppm (4H): $CH_2$—$CH_2$—$CH_2$—, (tt) at 1.7-1.8 ppm (4H): $CH_2$—$CH_2$—$CH_2$—, (t) at 0.7-1.8 ppm (4H): Si—$CH_2$—$CH_2$—.

(2) Formation of a Self-Assembled Monolayer (SAM) of the Amide Described in (1) on Gold Nanoparticles with Subsequent Silica Encapsulation The product (2 mg) described in (1) is dissolved in 1 ml of dry dimethylformamide (DMF) and added dropwise to 40 ml of a polyvinylpyrrolidone (PVP)-stabilized solution containing gold hollow nanoshells in dry DMF under stirring (about 400 rpm). After 20 h the formation of the self-assembled monolayer (SAM) on the hollow gold shells is completed. This is confirmed by the characteristic SERS spectrum of the SAM. The hollow gold shells, which are now functionalized with an organic monolayer, are purified by centrifugation (two times, each 45 min at 4000 rpm) and resuspension in 40 ml of dry DMF. The precipitate is dissolved in a mixture of 1.6 ml of Milli-Q-Water and 8 ml isopropanol. This solution is added dropwise to a mixture of 2.8 ml of Milli-Q-Water and 34 ml of isopropanol under vigorous stirring. 2.2 ml of a 25% ammonia solution are mixed with 6 ml of isopropanol and the solution is added dropwise to the functionalized nanoshell solution under vigorous stirring. While stirring for another 90 minutes hydrolysis takes place. Then, a 10 mM solution of tetraethoxysilicate (TEOS) in isopropanol is added stepwise: in each of the four successive additions, 1 ml of the TEOS solution is added dropwise followed by stirring for 1 h at 400 rpm. By varying the amount of TEOS, the thickness of the silica shell can be adjusted. The hollow gold nanoshells are now covered with a SAM containing the Raman marker units and they are encapsulated with a silica shell. To remove the small quantities of single silica particles the solution is purified by centrifugation (one time, 75 min at 2500 rpm) and the precipitate is dissolved in 10 ml of ethanol. (3-Aminopropyl)trimethoxysilane, APS, (0.3 mmol, 10 mM solution in isopropanol) is added dropwise under stirring (400 rpm) to a suspension of these silica-encapsulated and Raman marker functionalized nanoparticles. After 5 h of stirring at room temperature the corresponding amino-functionalized nanoparticles are obtained.

Figure 7:
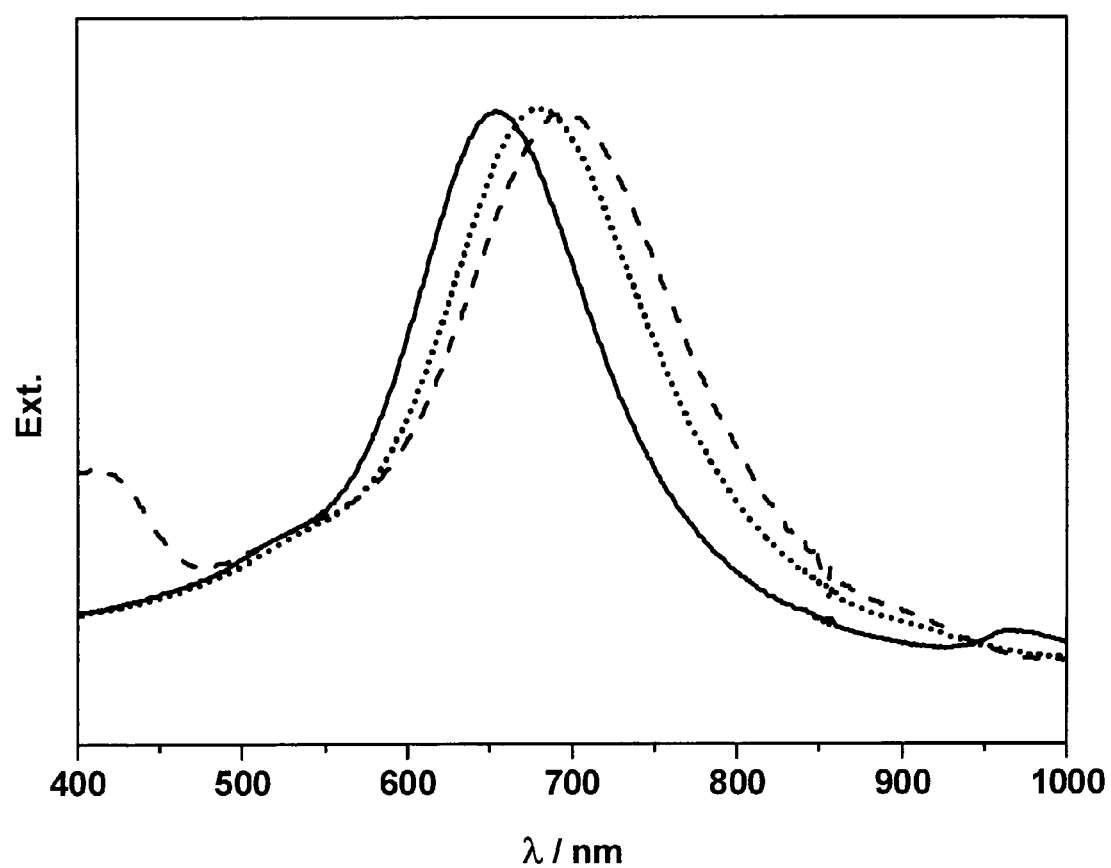
Figure 8:
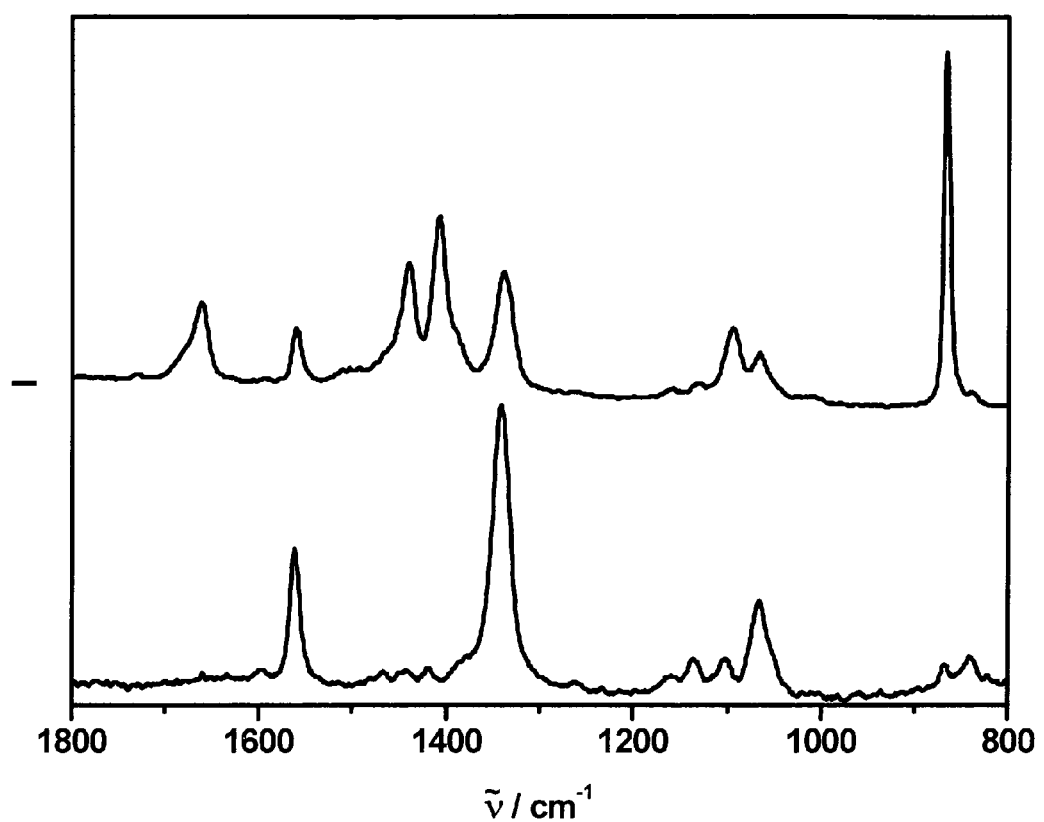
Figure 11:

The presence of a silica shell is clearly visible in the TEM pictures (TEM: transmission electron microscopy), FIG. 11. The presence and intactness of the SAM in the silica-encapsulated nanoparticles is demonstrated by the characteristic SERS signal of the Raman marker unit. Spectroscopic and microscopic characterizations of the silica-encapsulated nanoparticles are shown in FIG. 7 and FIG. 8

EXAMPLE 3

Synthesis of the Raman Marker Unit with a Spacer: 11-amino-undecane Acid a) Formation of the active ester:
5,5'-Dithio(2-nitrobenzoic acid-N-hydroxy succinimidester)

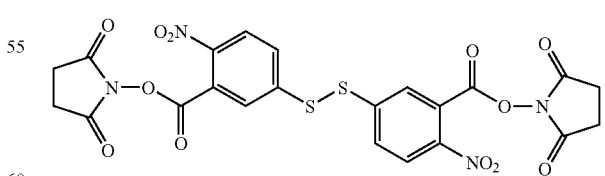

5,5'-Dithiobis(2-nitrobenzoic acid) (DTNB) is the Raman marker unit. DTNB (325 mg, 0.82 mmol) is dissolved at room temperature in a dry organic solvent, for example in 8 ml absolute DMF, under inert gas atmosphere such as argon. An active ester forming compound such as thionyl chloride, oxalyl chloride, EDC/sulfo-NHS, or DCC/hydroxy-malimide is added. In this experiment, we used NHS (207 mg, 1.8 mmol, 2 eq) and subsequently DCC (370 mg, 1.8 mmol, 2 eq) dissolved in 2 ml DMF. The reaction mixture is stirred sufficiently long (10-48 h) at room temperature or, if required, stirred at elevated temperatures (up to reflux), preferred is stirring for 16 h at room temperature. The solid urea derivative, which precipitates upon usage of EDC or DCC, is filtrated and the solution volume is reduced at the vacuum. The solid is suspended in a suitable organic solvent, for example 20 ml diethylether, washed with a polar organic solvent, for example isopropanol. Further purification is possible by column chromatography in an acid containing medium. Following the described procedure, we could obtain pure DTNB NHS ester (yield: 344 mg, 0.58 mmol, 71%). $R_f$(SiO$_2$, dichloromethane, 10% methanol, 1% trifluoro acetic acid) 0.8.

$^1$H-NMR (400 MHz, DMSO, 27° C.): δ=2.88 (s, 8H, NHS—CH$_2$), 8.11 (d, 2H, $^2$J=1.88 Hz, 5-H), 8.15 (dd, 2H, $^2$J$_{4H5H}$=8.60, $^2$J$_{4H2H}$=1.88, 4-H), 8.28 (d, 2H, $^2$J=8.60 Hz, 2-H)

b) Spacer conjugation with DTNB:
5,5'-dithio-(2-nitrobenzoic acid-1'-amidoundecan acid)

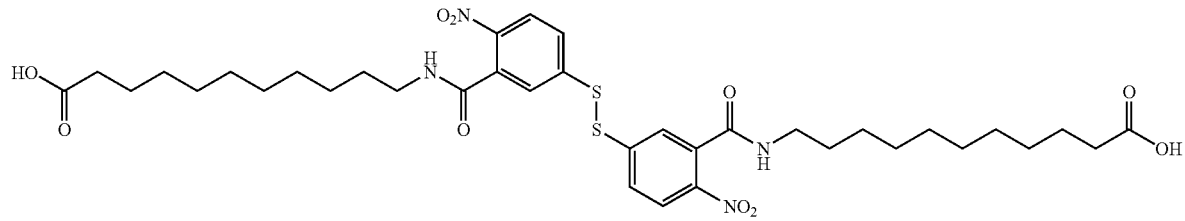 [SMILES: O=C(O)CCCCCCCCCCNC(=O)c1cc(SSc2ccc([N+](=O)[O-])c(C(=O)NCCCCCCCCCCC(=O)O)c2)ccc1[N+](=O)[O-]]

In this example, the spacer unit is 11-amino-undecanoic acid. The spacer (411 mg, 2.04 mmol, 4 eq) is suspended in a dry organic solvent, for example tetrahydrofuran (THF). Depending on its solubility and the stability of the Raman marker unit, the suspension temperature can be varied between −78° C. and reflux. First, an auxiliary base (2.1 ml triethylamine) is added. Then, the activated marker unit in a suitable organic solvent, for example DTNB-NHS (300 mg, 0.51 mmol in 10 ml THF and 5 ml DMF), is added dropwise. Depending on the reactivity, the reaction mixture is stirred 10 to 48 h, in this case 16 h. The solvent is removed by vacuum, the remaining solid is washed with NaHSO$_4$ solution and a suitable organic solvent. Further purification can be achieved by column chromatography, preferably on reversed phase silica (yield: 260 mg, 0.34 mmol, 67%).

$^1$H-NMR: (400 MHz, DMSO, 27° C.): δ=1.25 (s, 24H, CH$_2$), 1.48 (brs, 8H, CH$_2$), 2.18 (t, 4H, $^3$J=3.32 Hz, CH$_2$COOH), 3.18 (m, 4H, CH$_2$NH), 7.71 (d, 2H, $^2$J=2.16 Hz, 5-H), 7.79 (dd, 2H, $^2$J$_{4H5H}$=8.72, $^2$J$_{4H2H}$=2.16, 4-H), 8.08 (d, 2H, $^2$J=8.72 Hz, 2-H), 8.62 (t, 2H, $^3$J=5.68 Hz, NH), 11.65 (brs, 2H, COOH).

EXAMPLE 4

AgNO$_3$, polyvinylpyrrolidone (PVP), ethyleneglycol, HAuCl$_4$, 5,5'-dithiobis(2-nitrobenzoic acid) (DTNB), poly(allylamine-hydrochloride) (PAH), tetraethylorthosilicate (TEOS), aminopropyl-tri-methoxysilane (APS), anhydrous DMF, isopropanol, ethanol, phosphate buffer saline (PBS), fluorescamine were purchased from Aldrich/Fluka. Succinimidyl-[(N-maleimidopropionamido)-(dodecaethylengly-col)]ester (hetero-bifunctional crosslinker), Dylight 488 Microscale labeling kit, goat anti-Mouse IgG Dylight 488 conjugated were purchased from Pierce Biotechnology. Monoclonal mouse anti-human prostate-specific antigen (PSA) was purchased from Dako cytomation.

Nanoparticle Synthesis

Spherical Ag nanoparticles with an average diameter of 35 nm were synthesized with the polyol method, using AgNO$_3$ and PVP in ethylene glycol as described in Silvert, J. Mater. Chem. 1997, 7, 293; Wiley, Chem. Eur. J. 2005, 11, 454.

3 ml of the concentrated Ag nanoparticle solution was diluted in 300 ml of millipore water and heated to 100° C. under reflux. To the boiling solution, HAuCl$_4$ was added dropwise until the absorption maximum of the solution shifted to about 650 nm. The synthesized hollow gold nanoparticles had an average diameter of 54 nm, as determined by electron microscopy.

SERS Marker Synthesis 40 ml of the colloidal Au solution was centrifuged for 40 min at 4000 rpm and the precipitate was redispersed in 40 ml ethanol. 5 mg of DTNB (or an equal amount of an alternative Raman marker) were dissolved in 1 ml ethanol and added to the Au nanoparticle solution under vigorous stirring and were allowed to react for 8 hours. The formation of a complete self-assembled monolayer was monitored by Raman microspectroscopy, as determined by a maximum SERS signal of DTNB.

Polyelectrolyte Coating 40 ml of the Raman-labelled colloid was centrifuged twice (40 min, 4000 rpm) to remove excess Raman marker molecules and redispersed in 20 ml H$_2$O. This solution was added dropwise under vigorous stirring to 20 ml PAH-solution (2 g/l PAH and 3.5 g/l NaCl in H$_2$O), which has been sonicated for 15 min. The solution was stirred for 3 hours and then centrifuged for 40 min at 4000 rpm. The Au colloid was redispersed in 20 ml H$_2$O and added dropwise to 20 ml PVP solution (4 g/l PVP in H$_2$O). The solution was allowed to react overnight under vigorous stirring.

Silica Coating

The polyelectrolyte-coated particle solution was centrifuged twice at 4000 rpm for 50 min and redispersed in a solution of 5.2 ml H$_2$O and 6 ml isopropanol. 8.25 ml of NH$_3$-isopropanol-solution (4 vol-% NH$_3$) was added and under vigorous stirring a total amount of 1.2 ml TEOS-solution (1 vol-% TEOS in isopropanol) was added in six steps over 6 hours. The thickness of the silica shell can be controlled by the amount of TEOS. Morphology and shell thickness were determined by electron microscopy.

Amino-Functionalization of the Silica Surface

The silica-coated, Raman-labelled nanoparticles were centrifuged at 4000 rpm for 50 min and redispersed in 40 ml ethanol. They were sonicated thoroughly. The solution was heated to 40° C. and 500 μl APS were added under stirring. After one hour the heating was stopped and the solution was allowed to react for 5 hours at room temperature. The particle solution was centrifuged four times at 4000 rpm for 50 min. The presence of free amino groups was demonstrated by a fluorescence test with fluorescamine.

Conjugation to Antibody

The amino-functionalized nanoparticles were centrifuged 4 times at 4000 rpm for 60 min to remove excess APS and redispersed in 40 ml anhydrous DMF under an inert gas atmosphere. The heterobifunctional crosslinker was diluted in anhydrous DMF (10 g/l) and 2 ml of the crosslinker-solution was added to the colloidal dispersion. The reaction was stirred for 40 min under anhydrous conditions. Then triethylamine was added to the solution up to 5 mM and allowed to react for 3 h. The nanoparticle-crosslinker solution was centrifuged two times for 50 min at 4000 rpm and redispersed in 2 ml DMF.

The buffer of the antibody was exchanged to PBS-solution (pH 7.2). 18 ml of PBS-solution were added to 200 µl antibody solution. The resulting antibody solution was then added to the nanoparticle dispersion and was allowed to react for 24 hours. To get the nanoparticle-antibody dispersion ready for tissue application the solution was centrifuged twice (4000 rpm, 40 min) to remove excess antibody and redispersed in 20 ml PBS-solution. The formation of a bond between the amino-functionalized nanoparticles and the antibody was shown by using fluorescence labelled antibody parallel to unlabeled antibody.

Figure 13:
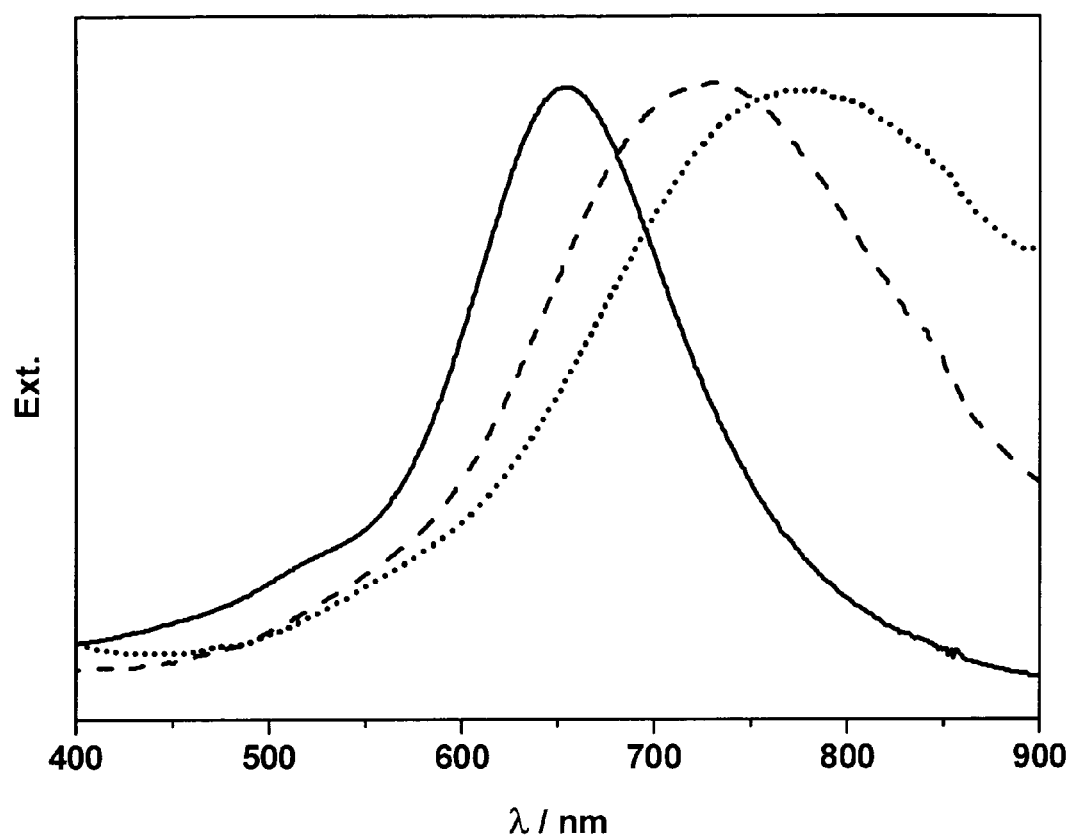
Figure 14:
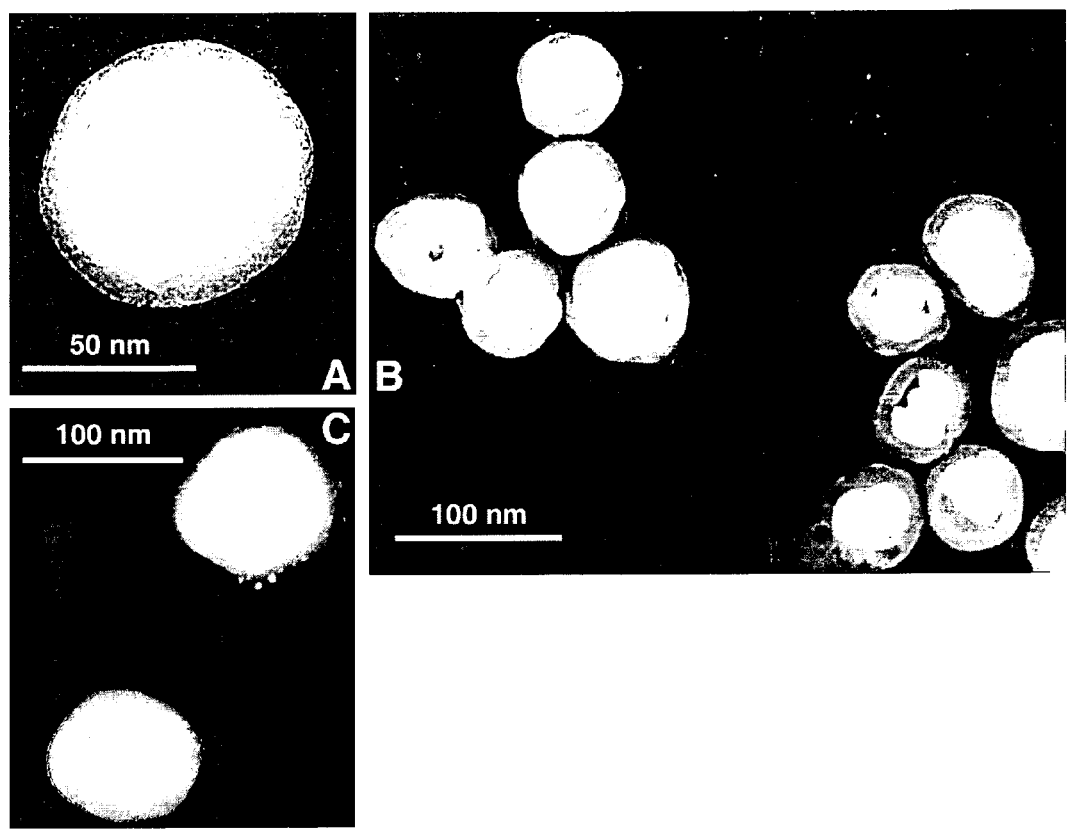
Figure 15:
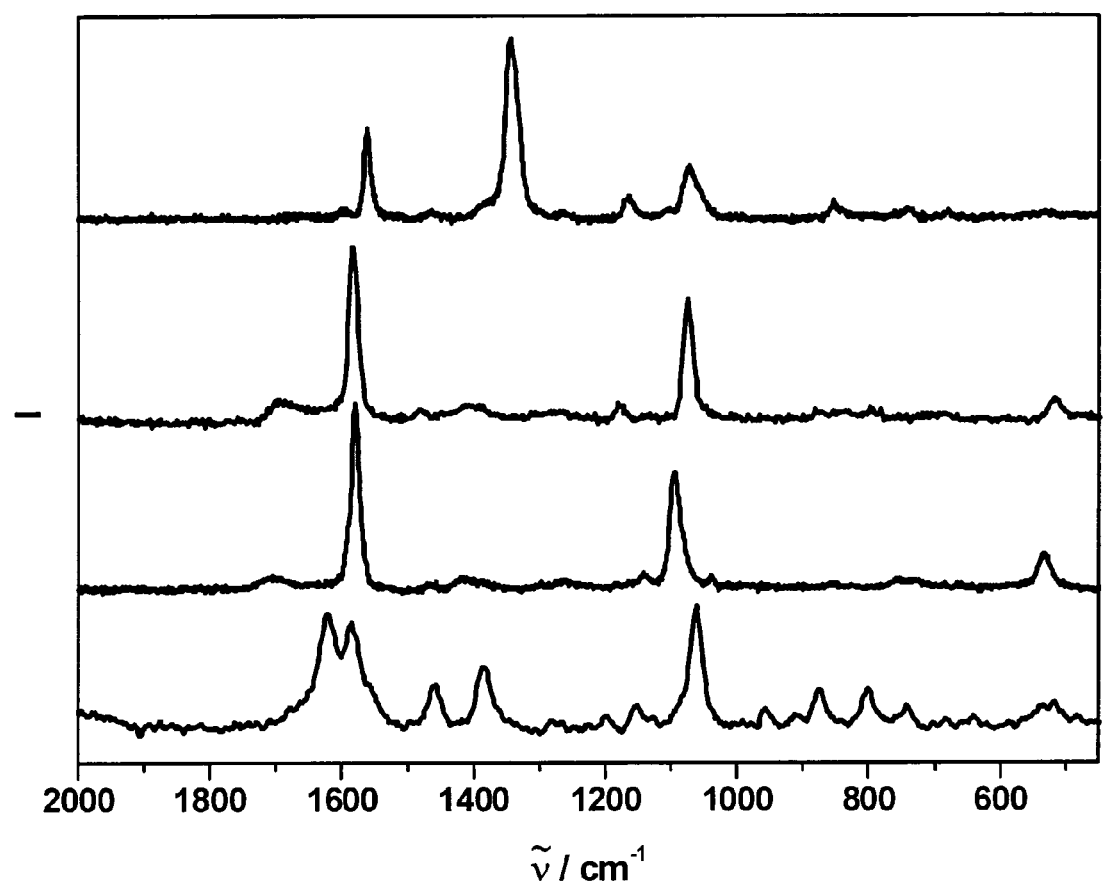

FIGS. 13 and 14 show a characterization of particles obtained in Example 4.

EXAMPLE 5 a) Synthesis of a Conjugate Between a Raman-Active Reporter Group, Ra, (Here: DTNB) and a Short Spacer Group Sp* (Here: Comprising a Monoethylene Glycole Unit)

198.2 mg (0.5 mmol) 5,5'-dithiobis(2-nitrobenzoic acid) (DTNB), 572.4 mg (1.1 mmol) (benzotriazol-1-yloxy)tripyrrolidino-phosphonium-hexafluoro-phosphate (Pybop) and 134.4 mg (1.1 mmol) 4-(dimethylamino)pyridine (DMAP) were suspended in 10 ml dichloromethane (DCM). In order to increase the solubility of the reagents, 3 drops of dimethylformamide were added. 115.7 mg (1.1 mmol) aminoethoxyethanol were slowly added to the clear yellow solution and the resulting orange solution was stirred for 4 days at room temperature. After removing the solvent under vacuum, the residue was purified by column chromatography (silica; dichloromethane/methanol/trifluoroacetic acid 100/10/1). Further purification was achieved with medium pressure liquid chromatography (MPLC) using a reversed phase column (RP 18) and a solvent mixture (dichloro-methane/methanol/trifluoroacetic acid). Yield: 35%. $R_f$ (silica; DCM/MeOH 10/1): 0.875.

$^1$H-NMR (250 MHz, dimethyl sulfoxide-$d_6$): δ=3.51 (m, 9H, $CH_2CH_2OCH_2CH_2OH$), 7.78 (m, 2H, Ar—H), 8.13 (d, 1H, Ar—H), 8.76 (s, 1H, $ArCONHCH_2CH_2OCH_2CH_2OH$)

b) Synthesis of a Conjugate Between a Raman-Active Reporter Group, Ra, (Here: DTNB) and a Longer Spacer Group Sp (Here: Comprising a Triethylene Glycole Unit)

Under a protective nitrogen atmosphere, 198.2 mg (0.5 mmol) DTNB were dissolved in a mixture of 1 ml tetrahydrofuran (THF) and 10 ml DCM. 260 µl (3 mmol) oxalyl-chloride were added to the solution. A catalytic amount of dimethylformamide (2 drops) was added. After reflux for 1 h, the solvent was removed under vacuum. The yellow residue was dissolved in 2 ml dichlormethane, and 350 mg (1.3 mmol) tert-butyl 3-[2-(2-(2-aminoethoxy)-ethoxy)ethoxy]propionate and 120 µl triethylamine were added. After 12 h reaction time, the orange solution was purified by column chromatography (silica; dichloromethane/methanol). The isolated intermediate product was stirred for 2 h in a solution of DCM and trifluoroacetic acid. Purification was achieved by reversed phase MPLC (RP 18, water/methanol). Yield: 20%.

$^1$H-NMR (250 MHz, $CDCl_3$): δ=2.42 (b, 2H, $CH_2CH_2OCH_2CH_2OCH_2CH_2OCH_2CH_2COOH$), 3.62 (m, 15H, $CH_2CH_2OCH_2CH_2OCH_2CH_2OCH_2CH_2COOH$), 7.38 (s, 1H, $ArCONH(CH_2CH_2O)_3COOH$), 7.62 (m, 2H, Ar—H), 8.2 (d, 1H, Ar—H)

c) Formation of a Mixed/Dual SAM

The centrifugate of 2 ml of a colloidal solution containing hollow gold particles was dissolved in 1 ml of a 1 mM solution containing the Raman-active reporter unit attached to the short spacer unit (DTNB with monoethylene glycole unit) and 1 µl of a 1 mM solution containing the Raman-active reporter unit attached to the longer spacer unit (DTNB with triethylene glycole unit). After treatment in an ultrasonic bath for 2 minutes the mixture was stirred for 4 h. The solvent for preparing the solutions containing the Raman-active reporter molecules was a 1:1 water-ethanol mixture. After formation of a complete SAM, monitored by the maximum SERS signal for the Raman reporter molecule, the colloid was washed twice with 50 mM phosphate buffered saline (PBS), pH 7.0.

d) Biofunctionalization of the Mixed/Dual SAM

Figure 9:
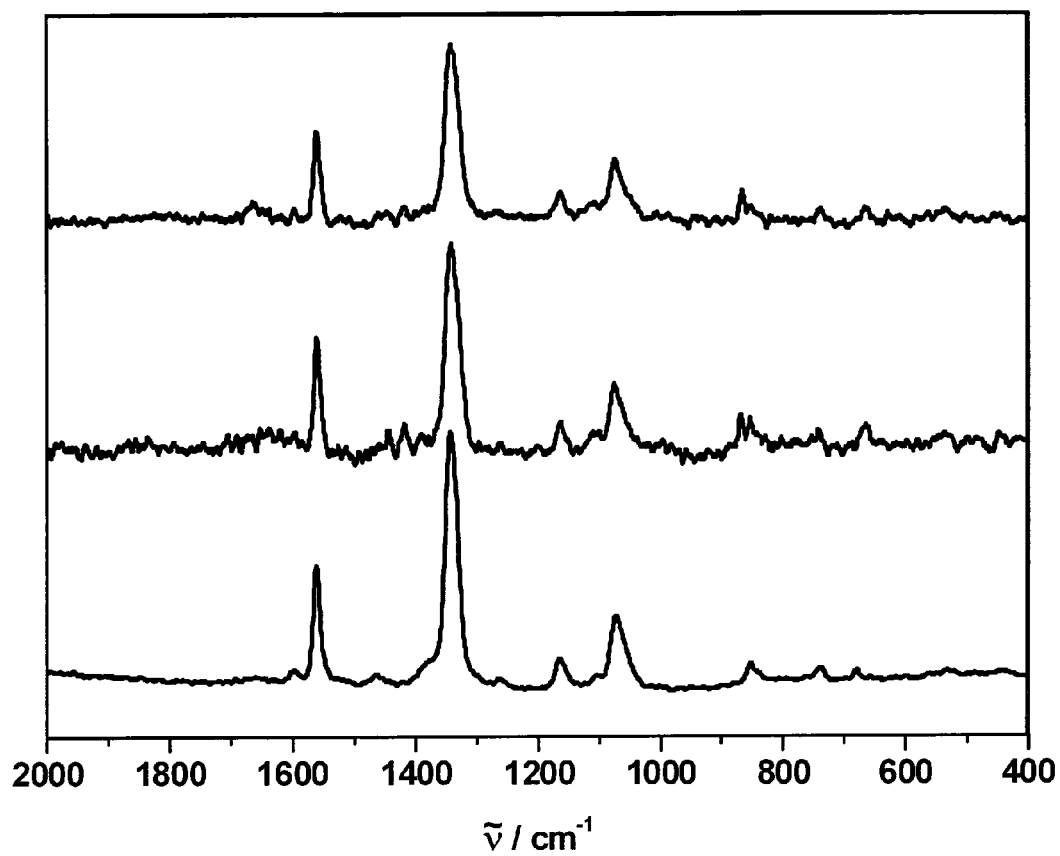
Figure 10:
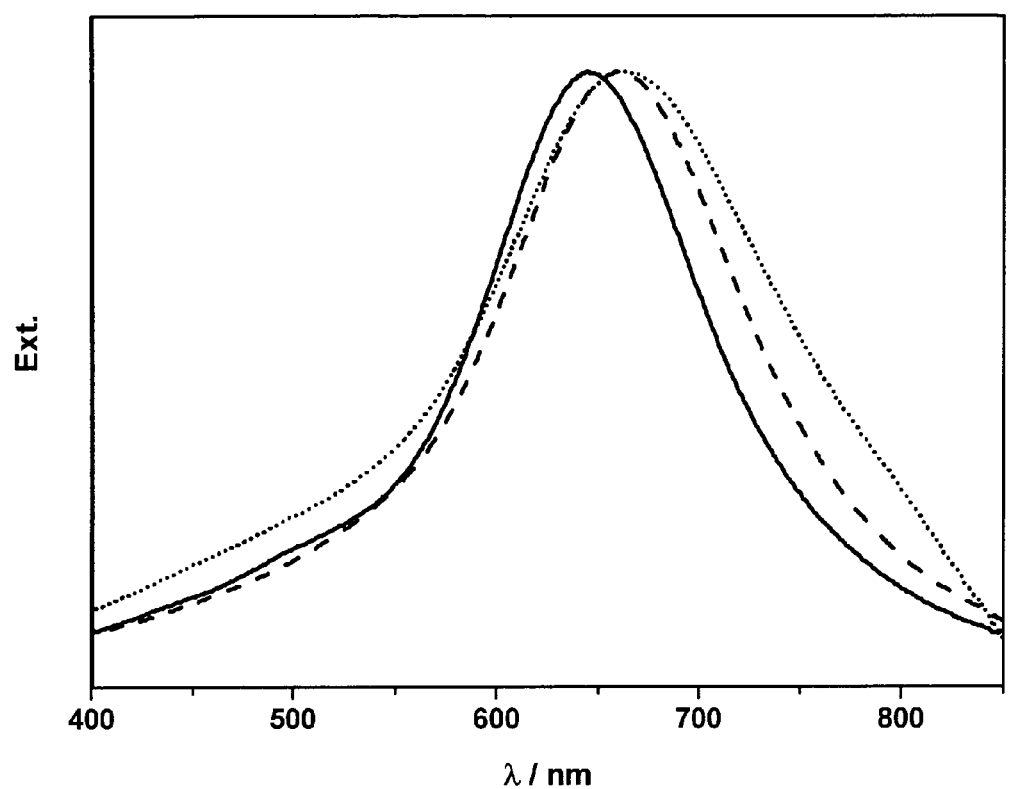

To the centrifugate of 2 ml of the colloidal solution functionalized with the Raman-active reporter molecules obtained in c), 500 µl of a 2 mM solution of N-(3-dimethylaminopropyl)-N'-ethylcarbodiimide in PBS and 500 µl of a 5 mM solution of N-hydroxysulfosuccinimide (sodium salt) were added and stirred for 30 min. In order to prevent particle aggregation, 1% TWEEN® 80 was added prior to biofunctionalization; N-hydroxysulfosuccinimide sodium salt was provided before addition of N-(3-dimethylaminopropyl)-N'-ethylcarbodiimide. After washing with PBS containing 1% TWEEN® 80, the residue was dissolved in a solution of PSA (prostate-specific antigen) antibody and rotated for 12 h. Washing was done with PBS. A spectroscopic analysis of the obtained conjugates is shown in FIGS. 9 and 10.

EXAMPLE 6

Figure 16:
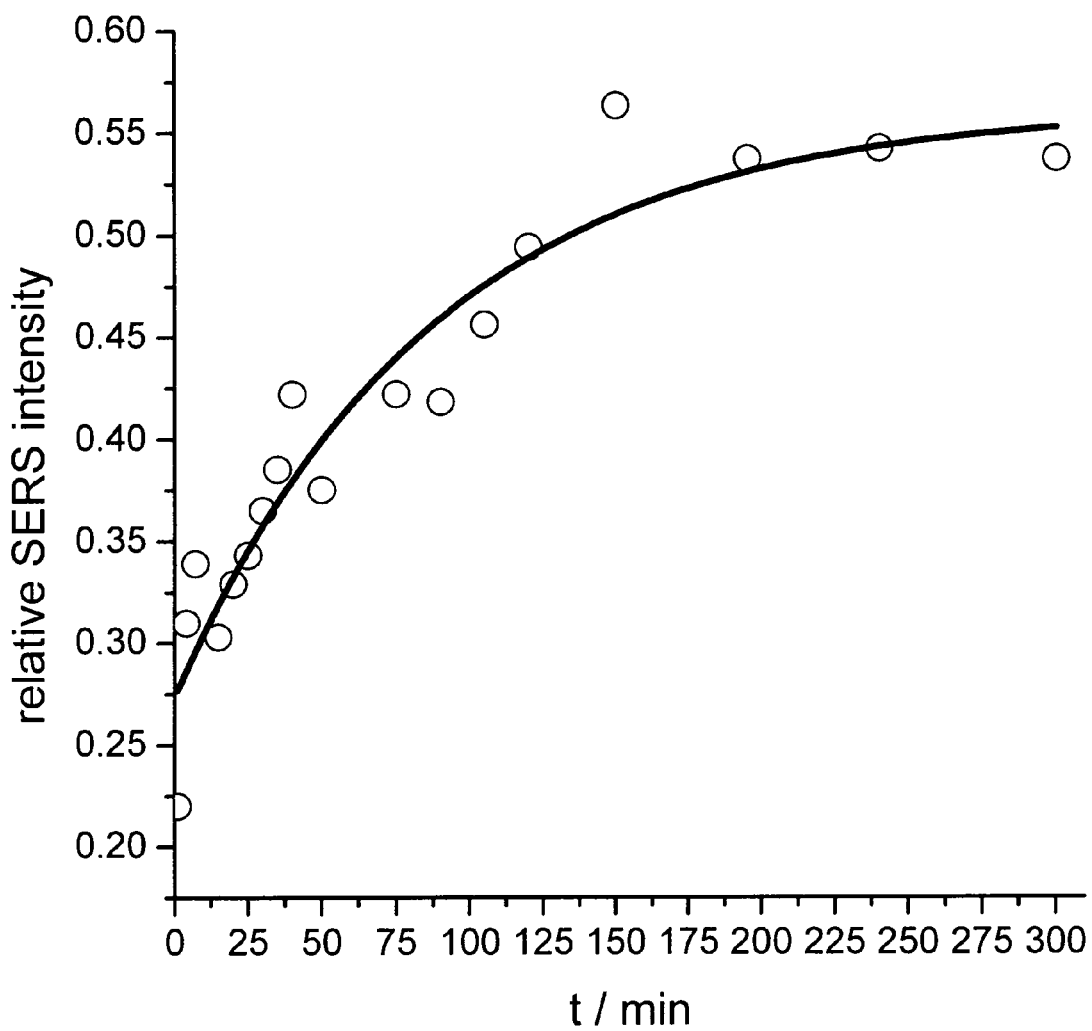

Kinetics of Self-Assembled Monolayer Formation 1.5 ml of a hollow gold nanoshell suspension were centrifuged for 5 min at 12 000 rpm and redispersed in a EtOH/polyvinylpyrrolidone (PVP) solution (1 g PVP in 40 ml EtOH). 7.2 mg 5,5'-dithiobis(2-nitrobenzoic acid) (DTNB) were dissolved in 5 ml EtOH. 10 µl of this solution were combined with 1.5 ml gold nanoshells in EtOH/PVP (final concentration of DTNB was 24 µM) in an Eppendorf tube and were shaken at 45° C. Raman spectra were recorded after 1, 4, 7, 15, 20, 25, 30, 35, 40, 50, 75, 90, 105, 120, 150, 195, 240 and 300 minutes. The SERS intensities of the 1340 $cm^{-1}$ peak of DTNB relative to the 882 $cm^{-1}$ peak of the solvent ethanol were plotted against the reaction coordinate, which is shown in FIG. 16 (circles). After 3 h the relative SERS intensity of DTNB reached a constant value, indicating the formation of a complete self-assembled monolayer on the surface of the nanoshells. The experimental data could be fitted with an exponential function (solid line).

EXAMPLE 7

BSA-Functionalization of Poly(Allylamine-Hydrochloride)-Coated SERS Markers Poly(allylamine-hydrochloride) (PAH)-coated SERS markers were synthesized according to example 4, aborting after the step of polyelectrolyte coating. 1 ml of the sample was centrifuged for 7 min at 12 000 rpm and redispersed in 0.5 ml phosphate-buffered saline (0.5 mM, pH 6.9). 0.16 ml of a BSA solution (5.4 mg BSA in 0.5 ml PBS) were added and shaken for 2 h. After centrifugation the precipitate was redispersed in 0.5 ml PBS and 30 µl of a 20 mM 1-ethyl-3-(3-dimethylaminopropyl) carbodiimide hydrochloride (EDC) solution was added and shaken for 45 min. The mixture was centrifuged for 7 min at 12 000 rpm and redispersed in milli-Q water. The zeta potential of the sample was −15 mV in water (pH 7) and 0 mV in acetate buffer (pH 4.7). The zeta potential of PAH-coated SERS markers in acetate buffer (pH 4.7) was 23 mV. These values clearly indicate a successful conjugation of BSA to the PAH-coated SERS marker.

EXAMPLE 8

Figure 17:
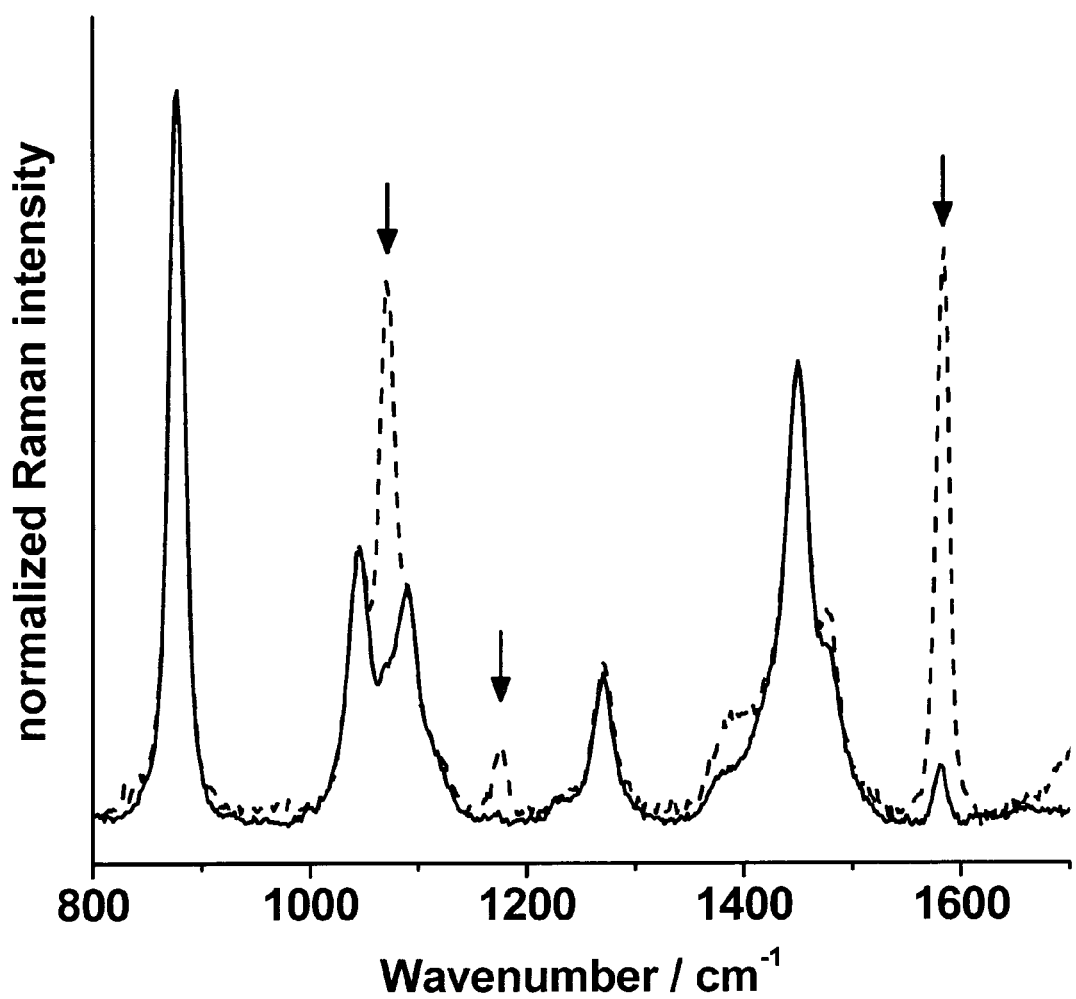

Comparison of SERS Markers Comprising a Monolayer or a Submonolayer, Respectively Au nanoshells were centrifuged for 5 minutes at 12 000 rpm and then redispersed in EtOH/polyvinylpyrrolidone (PVP) solution (1 g PVP in 40 ml EtOH). For the formation of a monolayer, 200 µl of a 10 mM 4-mercaptobenzoic acid (MBA) solution in EtOH were added to 600 µl Au nanoshells in EthOH/PVP. For the formation of a submonolayer, 180 µl of a 10 mM MPTMS solution in EtOH were added and followed by 20 µl of a 10 mM MBA-solution. The final concentration of MBA and MPTMS+MBA was 2.5 mM. Raman spectra were recorded after 3 hours without centrifugation to avoid aggregation. SERS signals of the Raman label (MBA) were normalized to the Raman band of ethanol at ~882 $cm^{-1}$. For the complete SAM, the SERS signals were 22±5 times brighter compared with the sub-monolayer coverage. The normalized spectra of both the marker comprising a monolayer and the marker comprising a submonolayer are shown in FIG. 17.

EXAMPLE 9

Figure 18:
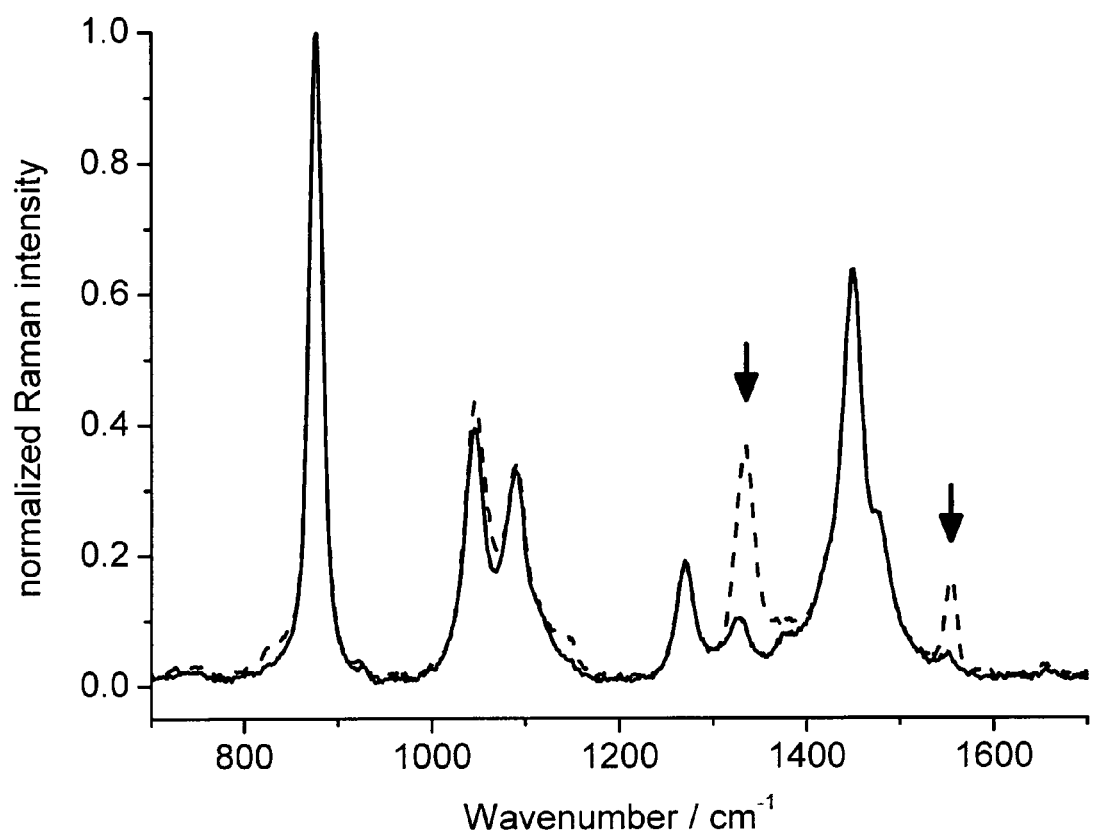

Comparison of SERS Markers Comprising a Gold Nanosphere or a Gold Nanoshell, Respectively Au nanoshells and Au nanospheres (both 60 nm diameter) were centrifuged (5 minutes, 12 000 rpm) and redispersed in 1.4 ml EtOH/polyvinylpyrrolidone (PVP) solution (1 g PVP in 40 ml EtOH). 100 µl of a 15 mM 5,5'-dithiobis(2-nitrobenzoic acid) (DTNB) solution in ethanol was added and the solution was stirred for 3 h. After centrifugation and redispersion in EtOH/PVP the samples were filtered to remove aggregates. Filters with 220 nm and 100 nm pores were used. The intensity of the extinction maxima of the colloidal solutions were then adjusted to the same value and the corresponding Raman spectra were recorded. The Au nanoshells show a 4.5 times higher SERS intensity compared to Au nanospheres, as it is shown in FIG. 18 (SERS signals from DTNB are marked with arrows). According to Mie calculations which are shown in detail below, 1.7 times more Au spheres are present in the sample because their extinction coefficient is 1.7 times lower compared to Au/Ag shells. This is equivalent to an approximately 8-fold increase in sensitivity for the same particle concentration.

Figure 19:
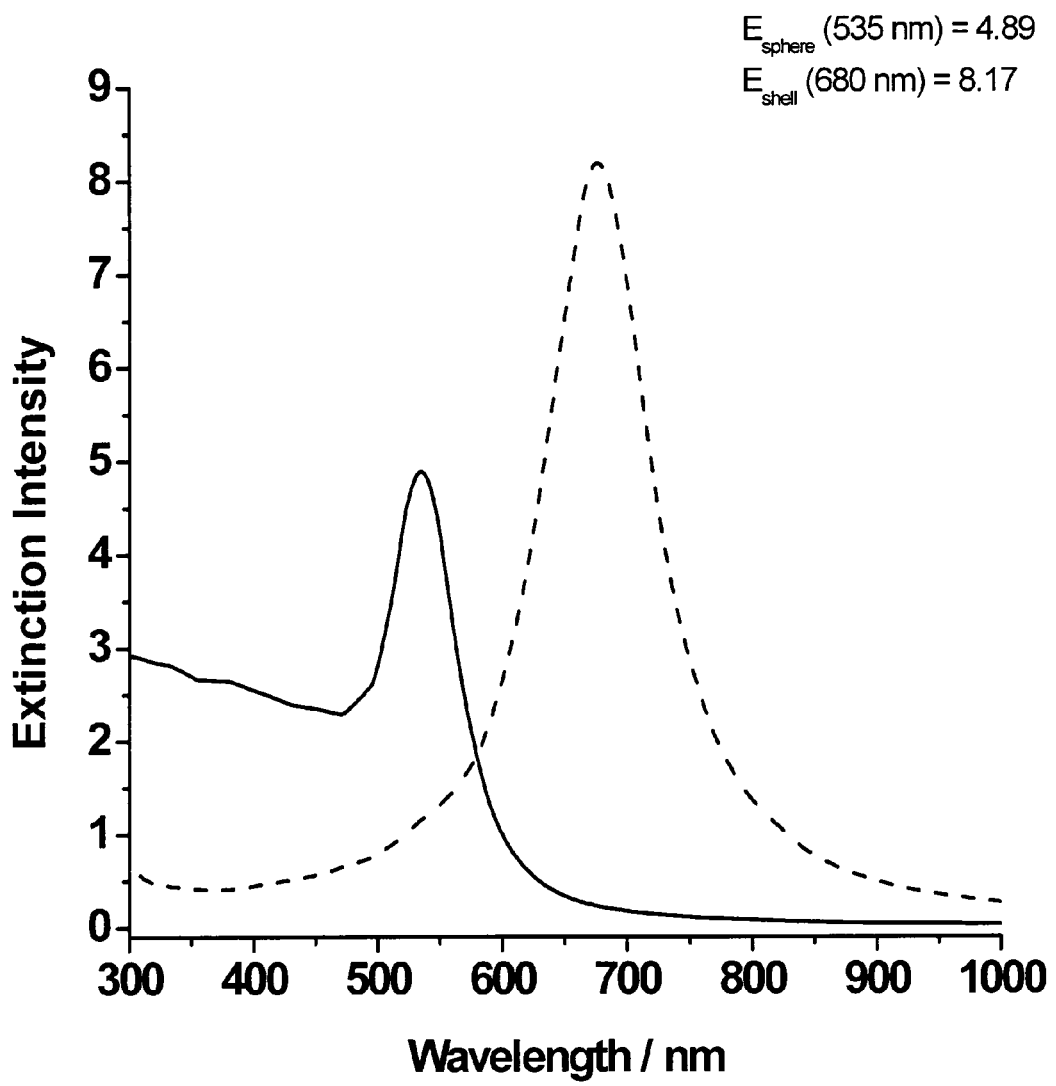

The Mie calculations mentioned above are explained in the following: The extinction intensity is defined as the following equation: E=∈·c·d. Setting c and d as a constant leads to E∝∈, thus $E_{sphere}/E_{shell}=\epsilon_{sphere}/\epsilon_{shell}$. Solving the above equation for $\epsilon_{shell}$ results finally in: $\epsilon_{shell}=\epsilon_{sphere}\cdot E_{shell}/E_{sphere}$. Using the equation from Liu and coworkers (X. Liu, M. Atwater, J. Wang, Q. Huo, Col. Surf. B, Biointerf. 58 (2007) 3-7), ln $\epsilon_{sphere}$=k·ln D+α, which has been reported for gold nanoparticles and incorporating for k=3.32111, D=60 and a=10.80505 leads to an extinction coefficient for gold nanoparticles $\epsilon_{sphere}$=3.96·10$^{10}$M$^{-1}$cm$^{-1}$. According to Mie calculations for 60 nm nanoparticles (for Au nanoshells a shell thickness of 4.5 nm was supposed) the extinction intensity is given by $E_{shell}/E_{sphere}$=8.17/4.89=1.68, which is shown in FIG. 19.

EXAMPLE 10

Standard Operating Procedure for the Formation of a Polyelectrolyte/Silica-Encapsulated SERS Marker a) Nanoparticle synthesis. Spherical Ag nanoparticles with an average diameter of 55 nm were synthesized with the polyol method, using AgNO$_3$ and polyvinylpyrrolidone (PVP) in dry ethylene glycol as described in Silvert, J. Mater. Chem. 1997, 7, 293; Wiley, Chem. Eur. J. 2005, 11, 454. Briefly, 2 g PVP K30 (molecular weight: about 40 000) dissolved in 13 ml dry ethylene glycol were heated at 165° C. in a 50 ml flask. Then a solution of 317.4 mg AgNO$_3$ in 2 ml ethylene glycol was added dropwise and the mixture was stirred for 70 min at 165° C. to obtain a yellow-grey suspension of Ag-nanoparticles. The Ag colloid was diluted with milli-Q water to a final volume of 1 l. The diluted colloidal suspension was centrifuged twice at 4000 rpm for 60 min and the precipitate was redispersed in an aqueous PVP solution (1 g PVP K30/1 l H$_2$O). The Ag nanoparticle solution with an optical density of 2.5 at approximately 420 nm was heated to 100° C. under reflux. To the boiling solution, an aqueous 1 mM HAuCl$_4$ solution was added dropwise until the extinction maximum of the solution shifted to 630 nm. The nanoshell suspension was centrifuged for 60 min at 4000 rpm and the precipitate was redispersed in ethanol (optical density of 5 at 630 nm). The synthesized hollow gold nanoparticles had an average diameter of 55 nm, as determined from electron microscopy.

b) SERS marker synthesis. 10 mg of 5,5'-dithiobis(2-nitrobenzoic acid) (DTNB; or an equal amount of an alternative Raman marker) were diluted in 20 ml ethanol and added to 20 ml of the Au nanoshell suspension under vigorous stirring and the mixture was allowed to react for 8 hours. The formation of a complete self-assembled monolayer was monitored by Raman microspectroscopy, as determined by a constant SERS signal intensity of DTNB.

c) Polyelectrolyte coating. The Raman-labelled colloid was centrifuged (90 min, 4000 rpm) and redispersed in 40 ml H$_2$O. This solution was added dropwise under vigorous stirring to 20 ml poly(allylamine-hydrochloride) (PAH) solution (2 g/l PAH and 3.5 g/l NaCl in H$_2$O), which has been sonicated for 15 min. The solution was stirred for 3 hours and then centrifuged for 60 min at 4000 rpm in polypropylene tubes. The Au colloid was redispersed in 20 ml H$_2$O and added dropwise to 20 ml PVP solution (4 g/l PVP in H$_2$O) under vigorous stirring. The solution was stirred overnight.

d) Silica coating. The polyelectrolyte-coated particle solution was centrifuged twice at 4000 rpm for 60 min and redispersed in H$_2$O to obtain an optical density of 13 at the maximum of the plasmon peak. 6.1 ml of this colloid was mixed with 16.5 ml isopropanol and 375 µl NH$_3$ solution (25%) under vigorous stirring. A total amount of 3.4 ml tetraethylorthosilicate (TEOS) solution (1 vol-% TEOS in isopropanol) was added in six steps over 24 hours. Then the mixture was stirred for another 12 h. Finally the silica-coated Raman-labelled nanoshells were centrifuged (60 min at 4000 rpm) and redispersed in water. The thickness of the silica shell was 35 nm, determined by electron microscopy. The thickness of the silica shell can be controlled by the amount of TEOS added.

e) NH$_2$-functionalization of the silica surface. 15 ml of the silica-coated, Raman-labelled nanoparticles (optical density of 5.5 at maximum of plasmon peak) were centrifuged at 4000 rpm for 60 min and redispersed in 10 ml water and 1.5 ml of 25% NH$_3$ was added. The mixture was sonicated thoroughly. After centrifugation (60 min at 4000 rpm) the precipitate was redispersed in 5 ml ethanol and 750 µl 25% NH$_3$. 20 µl 3-amino-n-propyltrimethoxysilane were added and the mixture was allowed to react in a shaker (1250 rpm, 22° C.) for 16 h. Then the solution was heated to 50° C. for one hour in the shaker. The particle solution was purified by centrifugation at 4000 rpm for 50 min and redispersion in 120 mM acetate buffer (pH 4.7). Finally the colloid was centrifuged and redispersed in water. The amino-functionalization resulted in a Zeta potential of approximately +30 mV in 1 mM acetate buffer (pH 4.7).

COMPARATIVE EXAMPLE 11

Preparation of SERS Markers According to US 2006/0054506 A1

SERS markers were synthesized according to the teaching of US 2006/0054506 A1. The molecules comprising a Raman marker and a silica precursor disclosed in paragraph 0064 were employed in SERS marker synthesis, following the instructions derived from Examples 1 and 3.

a) Synthesis of Au colloids. All solutions were prepared in water, unless specified otherwise. The following steps were performed A solution was prepared from 1 ml of 8% sodium citrate in 0.01 M NaOH, 100 µl of 10$^{-4}$% NaBH$_4$ in 0.01 M NaOH, and 500 µl 0.01 M NaOH. At the same time, 200 µl of 400 mM H$_4$NOCl were added to 150 ml of a 0.01% HAuCl$_4$ solution under vigorous stirring. After 20 min, the above mentioned NaBH$_4$/sodium citrate solution was added to the H$_4$NOCl/HAuCl$_4$ solution. An absorbance spectrum of the reaction batch was recorded, having a local maximum at 510 nm. Using transmission electron microscopy (TEM), the average size of the gold colloids obtained was determined to be 14 nm in diameter, as compared to the reported size of 45 nm in diameter.

b) Functionalization of the 14 nm gold nanoparticles with molecules comprising a Raman marker and a silica precursor disclosed in US 2006/0054506 A1, paragraph 0064, i.e. aminophenyltrimethoxysilane, 3-(2,4-dinitrophenylamino)propyltriethoxysilane, N-(3-triethoxysilylpropyl)-4,5-dihydroimidazole, and 2-cyanoethyltrimethoxysilane. The amounts of 3-aminopropyltrimethoxysilane (APTMS) and of the Raman label mixture given in Example 3, paragraph 0284, were used to calculate a total amount of substance of n=4.65·10$^{-8}$ mol. A solution of each one of the four compounds disclosed in paragraph 0064 was prepared as follows:
i) 8.3 µl aminophenyltrimethoxysilane+9991.7 µl water
ii) 3-(2,4-dinitrophenylamino)propyltriethoxysilane+9982 µl water
iii) N-(3-triethoxysilylpropyl)-4,5-dihydroimidazole+9987.4 µl water
iv) 2-cyanoethyltrimethoxysilane+9992 µl water 10 µl of each one of these four solutions was added to a separate batch of 30 ml of the above prepared solution of gold colloids. After 30 min, 1.2 ml of a 0.54% sodium silicate solution were added to each batch and stirred for 42 h. Subsequently, 120 ml EtOH, 1 ml 2 M ammonia, and 20 µl tetraethylorthosilicate (TEOS) were added to each batch. All batches were incubated for 12 h.

Figure 20:

After 12 h, the solution of the batch, that 2-cyanoethyltrimethoxysilane was added to, was completely colorless and aggregated gold colloids had precipitated. In all the other three batches, the solutions had a lightly red color and gold colloids had precipitated. All solutions were concentrated by centrifugation and prepared for recording Raman spectra and TEM images. The TEM images clearly showed that the gold nanoparticles were not uniformly silica-coated, and instead, long chains of pure silica had been formed, as shown in FIG. 20 for the batch that 2-cyanoethyltrimethoxysilane had been added to. A Raman spectrum of aggregated SERS markers could be recorded only of the batch that aminophenyltrimethoxysilane had been added to.

The invention claimed is:

1. A surface enhanced Raman scattering (SERS) marker comprising
   a metal particle;
   a self-assembled monolayer on the metal particle, the self-assembled monolayer consisting essentially of moieties comprising a Raman-active reporter group Ra and a group X which couples the moiety to the metal particle, wherein X can be comprised in Ra;
   an encapsulant surrounding the self-assembled monolayer, wherein the encapsulant is directly bound to the moieties comprising Ra; and
   a group Y which allows coupling of the SERS marker to a binding molecule;
   wherein the self-assembled monolayer consisting essentially of moieties comprising a Raman-active reporter group Ra comprises at least 85% the number of Raman-active reporter groups Ra compared with a metal particle entirely covered with a self-assembled monolayer formed solely of said moieties comprising Ra.

2. The SERS marker of claim 1, further comprising a spacer group Sp$^E$, wherein Sp$^E$ comprises a linear chain of at least three atoms separating the encapsulant and Y, and further wherein one terminal end of Sp$^E$ is bound to the outer surface of the encapsulant and the other terminal end of Sp$^E$ is bound to the group Y.

3. The SERS marker of claim 1, wherein the moiety comprising Ra further comprises an anchor group A and the encapsulant is covalently bound to A.

4. The SERS marker of claim 3, wherein A comprises an alkoxysilane group.

5. The SERS marker of claim 1, wherein the encapsulant comprises silica (SiO$_2$)$_x$.

6. The SERS marker of claim 1, wherein the encapsulant comprises one or more polymer layers.

7. The SERS marker of claim 6, wherein the encapsulant further comprises one or more additional encapsulant layers, wherein the one or more additional encapsulant layers are present on the outer surface of the outermost of the one or more polymer layers.

8. The SERS marker of claim 7, wherein the one or more additional encapsulant layers comprise silica $(SiO_2)_x$.

9. The SERS marker of claim 6, wherein the outermost of the one or more polymer layers comprises poly(vinylpyrrolidone).

10. The SERS marker of claim 1, wherein the encapsulant has a thickness of from 0.4 to 40 nm.

11. The SERS marker of claim 1, wherein the encapsulant has a thickness of from 1 to 20 nm.

12. The SERS marker of claim 1, comprising a spacer group $Sp^E$ and a spacer group $Sp^{E*}$, wherein $Sp^E$ comprises a linear chain of at least three atoms separating the encapsulant and Y, further wherein one terminal end of $Sp^E$ is bound to the outer surface of the encapsulant and the other terminal end of $Sp^E$ is bound to the group Y, further wherein $Sp^{E*}$ comprises a linear chain of atoms, and further wherein one terminal end of $Sp^{E*}$ is bound to the outer surface of the encapsulant and the other terminal end of $Sp^{E*}$ may be bound to the group Y, provided that the linear chain of atoms in $Sp^E$ is at least three atoms longer than the linear chain of atoms in $Sp^{E*}$.

13. The SERS marker of claim 1, wherein the metal particle comprises a metal selected from Ag, Au and Cu or alloys thereof.

14. The SERS marker of claim 1, wherein X comprises a sulfur atom or a nitrogen atom.

15. The SERS marker of claim 1, wherein Ra comprises an aromatic group, a carbon-carbon double bond and/or a carbon-carbon triple bond.

16. The SERS marker of claim 15, wherein Ra comprises an optionally substituted polyene, polydiacetylene, polyyne, aryl or heterocyclic group.

17. The SERS marker of claim 15, wherein Ra comprises at least one substituent selected from halogen, $NO_2$, CN, NC, OC(O)—$C_{1-4}$ alkyl, NHC(O)—$C_{1-4}$ alkyl, $NR^1_2$ ($R^1$=$C_{1-4}$ alkyl or $C_{6-10}$ aryl), $BF_3^-$, $SiR^2_3$ ($R^2$=$C_{1-4}$ alkyl, $C_{6-10}$ aryl or F), $PR^3_3$ ($R^3$=$C_{1-4}$ alkyl, $C_{6-10}$ aryl or $C_{1-4}$ alkoxy), $C_{1-4}$ perfluoroalkyl, $C_{1-4}$ alkyl, $C_{6-10}$ aryl, $C_{1-4}$ alkoxy, $C_{1-4}$ alkene, and $C_{1-4}$ alkyne.

18. The SERS marker of claim 17, wherein Ra comprises a phenyl group and the substituent is in the para-position with respect to X, and wherein X is a sulfur atom.

19. The SERS marker of claim 16, wherein Ra comprises a terpene or a terpenoid.

20. The SERS marker of claim 19, wherein Ra comprises a carotenoid or a derivative thereof.

21. The SERS marker of claim 1, wherein the self-assembled monolayer comprises two or more different Raman-active reporter groups.

22. The SERS marker of claim 2, wherein $Sp^E$ comprises a monomer unit or an oligomer or a polymer comprising 2 to 100 monomer units, wherein the monomer units are selected from optionally protected natural or non-natural amino acids, saccharides, ethers and alcohols.

23. The SERS marker of claim 1, wherein Y is activated as a N-hydroxysuccinimide (NHS), sulfo-NHS, haloacetyl, pyridyl disulfide, hydrazide, imidoester, isocyanate, phenyl azide, benzophenone, glyoxal or maleimide.

24. The SERS marker of claim 1, further comprising a binding molecule bond to Y.

25. A method for the preparation of the SERS marker of claim 1, the method comprising the steps of:
(i) providing a suspension of metal particles;
(ii) providing a solution of compounds comprising the linear structure (III)

$$X'\text{\textasciitilde}Ra \qquad (III)$$

wherein
X' is a group which allows coupling of the compound comprising structure (III) to a metal particle, and Ra is a Raman-active reporter group, wherein X' can be comprised in Ra;
(iii) adding the solution obtained in step (ii) to the suspension obtained in step (i), to provide the self-assembled monolayer on the metal particle;
(iv) forming an encapsulant, whereby the encapsulant is covalently bound to a compound comprising the linear structure (III);
(v) providing a group Y which allows coupling of the SERS marker to a binding molecule.

26. The method of claim 25, wherein, in step (iii), an excess of the compound comprising the Raman-active reporter group is added to the suspension obtained in step (i), to provide the self-assembled monolayer on the metal particles.

27. A method for the preparation of the SERS marker of claim 6, the method comprising the steps of:
(i) providing a suspension of metal particles;
(ii) providing a solution of compounds comprising the linear structure (III)

$$X'\text{\textasciitilde}Ra \qquad (III)$$

wherein
X' is a group which allows coupling of the compound comprising structure (III) to a metal particle, and Ra is a Raman-active reporter group, wherein X' can be comprised in Ra;
(iii) adding the solution obtained in step (ii) to the suspension obtained in step (i), to provide a self-assembled monolayer on the metal particle;
(iv) adding a solution of a polymer to the suspension obtained in step (iii), whereby a polymer layer is formed on the outer surface of the particle obtained in the previous step;
(v) optionally repeating step (iv) one or more times; and
(vi) providing a group Y which allows coupling of the SERS marker to a binding molecule.

28. The method of claim 27, wherein, in step (iii), an excess of the compound comprising the Raman-active reporter group is added to the suspension obtained in step (i), to provide the self-assembled monolayer on the metal particles.

29. The method of claim 27, further comprising the step of forming an additional encapsulant layer comprising silica on the outer surface of the outermost polymer layer.

30. The method of claim 25, further comprising the step of bonding one terminal end of a spacer group $Sp^E$ comprising a linear chain of at least three atoms to the outer surface of the encapsulant, wherein the other terminal end of $Sp^E$ is bound to the group Y.

31. The method of claim 30, further comprising the step of bonding one terminal end of a spacer group $Sp^{E*}$ comprising a linear chain of atoms to the outer surface of the encapsulant, wherein the other terminal end of $Sp^{E*}$ may be bound to the group Y, provided that the linear chain of atoms in $Sp^E$ is at least three atoms longer than the linear chain of atoms in $Sp^{E*}$.

32. An in vitro method for analyzing a biological sample, the method comprising:
(a) contacting the biological sample with at least one SERS marker of claim 31;
(b) allowing binding of the binding molecule of the at least one SERS marker to at least one component of the biological sample;
(c) irradiating the at least one SERS marker bound to the at least one component so as to cause Raman scattering of the SERS marker; and
(d) detecting the Raman scattering.

33. The method of claim 32, wherein said biological sample is selected from the group consisting of (a) virus(es), (a) prokaryotic cell(s), (a) plant cell(s) or tissue, (an) animal cell(s) or tissue or a body fluid.

34. A diagnostic composition comprising the SERS marker according to claim 1 further comprising a binding molecule coupled to the SERS marker through Y.

35. A method of diagnosing disease in a subject comprising the steps of:
(a) administering at least one SERS marker to the subject;
(b) allowing binding of binding molecule of the at least one SERS marker to a part of the subject;
(c) irradiating the at least one SERS marker bound to the part of the subject so as to cause Raman scattering of the SERS marker; and
(d) detecting the Raman scattering
wherein the SERS) marker comprises
a metal particle;
a self-assembled monolayer on the metal particle, the self-assembled monolayer consisting essentially of moieties comprising a Raman-active reporter group Ra and a group X which couples the moiety to the metal particle, wherein X can be comprised in Ra;
an encapsulant surrounding the self-assembled monolayer, wherein the encapsulant is directly bound to the moieties comprising Ra; and
a group Y which allows coupling of the SERS marker to a binding molecule a binding molecule bound to Y;
wherein the self-assembled monolayer consisting essentially of moieties comprising a Raman-active reporter group Ra comprises at least 85% the number of Raman-active reporter groups Ra compared with a metal particle entirely covered with a self-assembled monolayer formed solely of said moieties comprising Ra.

36. The method of claim 35, wherein the diagnosis is employed to diagnose a disease selected from infectious disease, proliferative diseases, neurodegenerative diseases, cancers, psychological disorders, metabolic diseases, autoimmune diseases, sexually transmitted diseases, gastro-intestinal disorders, pulmonary disorders and cardiovascular disorders.

37. Method of diagnosing in a subject suspected of suffering from a disease selected from infectious disease, proliferative diseases, neurodegenerative diseases, cancers, psychological disorders, metabolic diseases, autoimmune diseases, sexually transmitted diseases, gastro-intestinal disorders, pulmonary disorders and cardiovascular disorders or suspected of being prone to suffering from said disease, comprising the steps of
(a) administering at least one SERS marker according to claim 31 to a subject;
(b) allowing binding of the binding molecule of the at least one SERS marker to a part of the subject;
(c) irradiating the at least one SERS marker bound to the part of the subject so as to cause Raman scattering of the SERS marker;
(d) detecting the Raman scattering of the at least one SERS marker; and
(e) comparing the Raman scattering of said at least one SERS marker detected in (d) with a reference Raman scattering of said at least one SERS marker detected in a control subject (healthy subject),
wherein said disease is diagnosed when said Raman scattering detected in (d) differs from said reference Raman scattering.

38. Method of diagnosing in a subject suspected of suffering from a disease selected from infectious disease, proliferative diseases, neurodegenerative diseases, cancers, psychological disorders, metabolic diseases, autoimmune diseases, sexually transmitted diseases, gastro-intestinal disorders, pulmonary disorders and cardiovascular disorders or suspected of being prone to suffering from said disease, comprising the steps of
(a) contacting at least one SERS marker according to claim 31 to a cell or tissue sample obtained from said subject;
(b) allowing binding of the binding molecule of the at least one SERS marker to at least one component of said cell or tissue sample;
(c) irradiating the at least one SERS marker bound to the at least one component of said cell or tissue sample so as to cause Raman scattering of the SERS marker;
(d) detecting the Raman scattering of the at least one SERS marker; and
(e) comparing the Raman scattering of said at least one SERS marker detected in (d) with a reference Raman scattering of said at least one SERS marker detected in a cell or tissue sample obtained from a control subject (healthy subject),
wherein said disease is diagnosed when said Raman scattering detected in (d) differs from said reference Raman scattering.

* * * * *